US010662422B2

(12) United States Patent
Smith et al.

(10) Patent No.: US 10,662,422 B2
(45) Date of Patent: *May 26, 2020

(54) METHOD FOR SELECTING POLYNUCLEOTIDES ENCODING ANTIGEN-SPECIFIC IMMUNOGLOBULIN SUBUNIT

(71) Applicant: Vaccinex, Inc., Rochester, NY (US)

(72) Inventors: Ernest S. Smith, W. Henrietta, NY (US); Tracy Pandina, Rochester, NY (US); Leslie A. Balch, Lakeville, NY (US); Mark Paris, Mendon, NY (US); Maurice Zauderer, Pittsford, NY (US); Angelica Cornelison, Pittsford, NY (US); Renee Kirk, Bloomfield, NY (US)

(73) Assignee: Vaccinex, Inc., Rochester, NY (US)

( * ) Notice: Subject to any disclaimer, the term of this patent is extended or adjusted under 35 U.S.C. 154(b) by 163 days.

This patent is subject to a terminal disclaimer.

(21) Appl. No.: 15/619,790

(22) Filed: Jun. 12, 2017

(65) Prior Publication Data

US 2017/0306318 A1  Oct. 26, 2017

Related U.S. Application Data

(60) Continuation of application No. 14/977,067, filed on Dec. 21, 2015, now Pat. No. 9,701,958, which is a (Continued)

(51) Int. Cl.
*C40B 40/08* (2006.01)
*C12N 15/10* (2006.01)
(Continued)

(52) U.S. Cl.
CPC ........ *C12N 15/1037* (2013.01); *C07K 14/005* (2013.01); *C07K 16/00* (2013.01);
(Continued)

(58) Field of Classification Search
None
See application file for complete search history.

(56) References Cited

U.S. PATENT DOCUMENTS 5,445,953 A   8/1995  Dorner
5,770,212 A   6/1998  Falkner
(Continued)

FOREIGN PATENT DOCUMENTS

EP   1516932 A1   3/2005
WO   2000/028016 A1   5/2000
(Continued)

OTHER PUBLICATIONS

Boesen, Non-Final Office Action issued in U.S. Appl. No. 13/844,388 dated Apr. 29, 2016, 8 pages.
(Continued)

*Primary Examiner* — Christian C Boesen

(57) ABSTRACT

The present invention relates to a high efficiency method of expressing immunoglobulin molecules in eukaryotic cells. The invention is further drawn to a method of producing immunoglobulin heavy and light chain libraries, particularly using the trimolecular recombination method, for expression in eukaryotic cells. The invention further provides methods of selecting and screening for antigen-specific immunoglobulin molecules, and antigen-specific fragments thereof. The invention also provides kits for producing, screening and selecting antigen-specific immunoglobulin molecules. Finally, the invention provides immunoglobulin molecules, and antigen-specific fragments thereof, produced by the methods provided herein.

4 Claims, 32 Drawing Sheets

Figure 2:
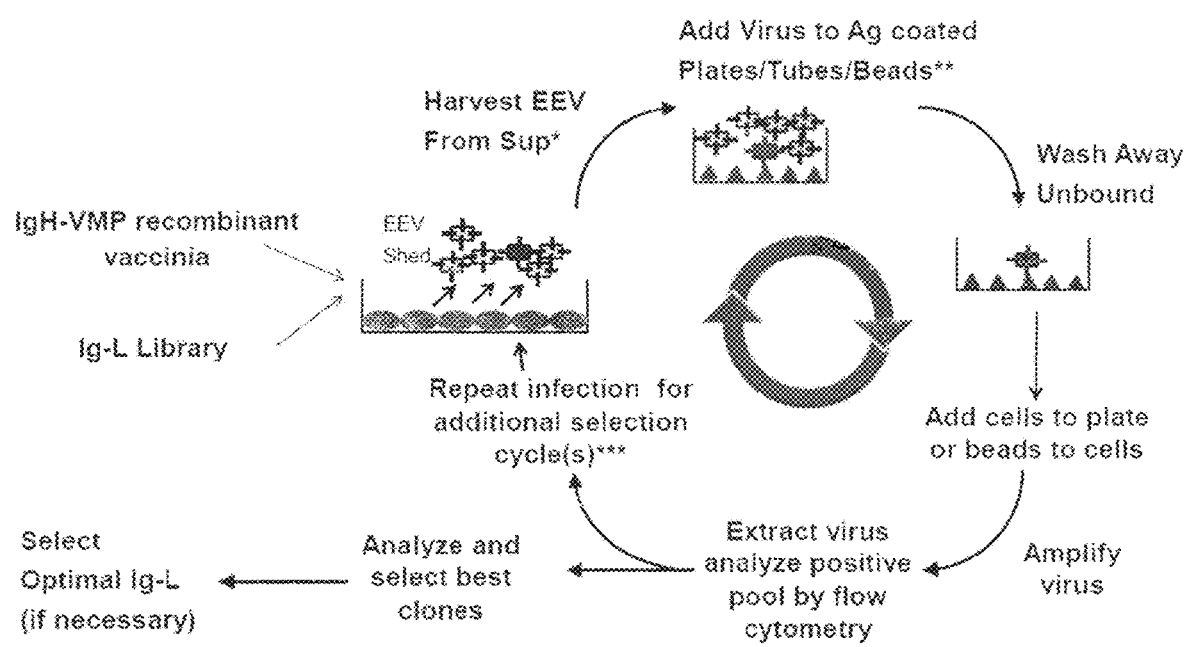

Specification includes a Sequence Listing.

Related U.S. Application Data division of application No. 13/844,388, filed on Mar. 15, 2013, now Pat. No. 9,708,601.

(60) Provisional application No. 61/639,046, filed on Apr. 26, 2012, provisional application No. 61/732,776, filed on Dec. 3, 2012.

(51) Int. Cl.

| | | |
|---|---|---|
| *C07K 16/00* | (2006.01) | |
| *C07K 14/005* | (2006.01) | |
| *C12N 15/86* | (2006.01) | |
| *C07K 16/28* | (2006.01) | |
| *C07K 16/32* | (2006.01) | |
| *C40B 30/04* | (2006.01) | |

(52) U.S. Cl.
CPC ........ *C07K 16/005* (2013.01); *C07K 16/2803* (2013.01); *C07K 16/32* (2013.01); *C12N 15/86* (2013.01); *C07K 2317/522* (2013.01); *C07K 2317/56* (2013.01); *C07K 2319/03* (2013.01); *C12N 2710/24122* (2013.01); *C12N 2710/24143* (2013.01); *C40B 30/04* (2013.01); *C40B 40/08* (2013.01)

(56) References Cited

U.S. PATENT DOCUMENTS

| | | | |
|---|---|---|---|
| 6,576,754 | B2 | 6/2003 | Hall |
| 6,706,477 | B2 | 3/2004 | Zauderer |
| 6,872,518 | B2 | 3/2005 | Zauderer |
| 7,700,102 | B2 | 4/2010 | Hall |
| 7,772,380 | B2 | 8/2010 | Porcelli |
| 7,858,559 | B2 | 12/2010 | Zauderer et al. |
| 7,858,599 | B2 | 12/2010 | Hander |
| 7,919,594 | B2 | 4/2011 | Smith |
| 8,022,043 | B2 | 9/2011 | Porcelli |
| 8,067,247 | B2 | 11/2011 | Belin |
| 8,496,938 | B2 | 7/2013 | Smith |
| 8,535,687 | B2 | 9/2013 | Draghia-Akli et al. |
| 8,637,026 | B2 | 1/2014 | Zauderer |
| 8,790,652 | B2 | 7/2014 | Basile |
| 8,816,058 | B2 | 8/2014 | Smith |
| 8,834,883 | B2 | 9/2014 | Croy |
| 9,090,709 | B2 | 7/2015 | Fisher |
| 9,139,809 | B2 | 9/2015 | Porcelli |
| 9,243,068 | B2 | 1/2016 | Evans |
| 9,249,227 | B2 | 2/2016 | Smith |
| 9,371,352 | B2 | 6/2016 | Porcelli |
| 9,382,327 | B2 | 7/2016 | Smith |
| 9,447,191 | B2 | 9/2016 | Takayanagi |
| 9,512,224 | B2 | 12/2016 | Zauderer |
| 9,598,495 | B2 | 3/2017 | Smith |
| 9,603,922 | B2 | 3/2017 | Donda |
| 9,605,055 | B2 | 3/2017 | Smith |
| 9,676,840 | B2 | 6/2017 | Smith |
| 9,701,958 | B2 | 7/2017 | Smith |
| 9,708,601 | B2 | 7/2017 | Smith |
| 9,790,271 | B2 | 10/2017 | Zauderer |
| 9,809,654 | B2 | 11/2017 | Robert |
| 9,828,435 | B2 | 11/2017 | Evans |
| 9,890,213 | B2 | 2/2018 | Smith |
| 9,963,504 | B2 | 5/2018 | Klimatcheva |
| 10,111,950 | B2 | 10/2018 | Porcelli |
| 10,301,393 | B2 | 5/2019 | Smith |
| 2003/0022157 | A1 | 1/2003 | Zauderer |
| 2005/0266425 | A1 | 12/2005 | Zauderer et al. |
| 2009/0304627 | A1 | 12/2009 | Draghia-Akli et al. |
| 2010/0081575 | A1 | 4/2010 | Williamson et al. |
| 2011/0008322 | A1 | 1/2011 | Zauderer |
| 2013/0095118 | A1 | 4/2013 | Smith |
| 2013/0164325 | A1 | 6/2013 | Porcelli |
| 2013/0288927 | A1 | 10/2013 | Smith et al. |
| 2013/0302320 | A1 | 11/2013 | Smith |
| 2014/0303358 | A1 | 10/2014 | Takayanagi |
| 2016/0152971 | A1 | 6/2016 | Smith et al. |
| 2019/0112388 | A1 | 4/2019 | Smith |

FOREIGN PATENT DOCUMENTS

| | | |
|---|---|---|
| WO | 20020062822 | 8/2002 |
| WO | 2004029206 | 4/2004 |
| WO | 2005055936 | 6/2005 |
| WO | 2011/110621 A1 | 9/2011 |
| WO | 2011/110642 A1 | 9/2011 |
| WO | 2011/140249 A2 | 11/2011 |
| WO | 2013/163602 A1 | 10/2013 |
| WO | 2017184951 | 10/2017 |
| WO | 2018026715 | 2/2018 |
| WO | 2018156509 | 8/2018 |
| WO | 2018175179 | 9/2018 |
| WO | 2018204895 | 11/2018 |

OTHER PUBLICATIONS

Chakrabarti et al., "Compact, Synthetic, Vaccinia Virus Early/Late Promoter for Protein Expression", BioTechniques, 1997, pp. 1094-1097, vol. 23 No. 6, Informa Healthcare USA, Inc., England.

Dehaven et al., "The Vaccinia Virus A56 Protein: A Multifunctional Transmembrane Glycoprotein that Anchors Two Secreted Viral Proteins", Journal of General Virology, 2011, pp. 1971-1980, vol. 92.

Furuyama et al., "Identification of a Novel Transmembrane Semaphorin Expressed on Lymphocytes", Journal of Biological Chemistry, Dec. 27, 1996, pp. 33376-33381, vol. 271 No. 52.

Galmiche et al., "Expression of a Functional Single Chain Antibody on the Surface of Extracellular Enveloped Vaccinia Virus as a Step Towards Selective Tumour Cell Targeting", Journal of General Virology, 1997, pp. 3019-3027, vol. 78, Great Britain.

GenBank Accession No. Q01218 retreived from http://ibis.internal.epo.org/exam/dbfetch.jsb?id=UNIPROT:Q01218 on Apr. 1, 1993.

GenBank Accession No. YP_233063.

Hammond et al., "A Synthetic Vaccinia Virus Promoter with Enhanced Early and Late Activity", Journal of Virological Methods, 1997, pp. 135-138, vol. 66 No. 1, Elsevier/North-Holland Biomedical Press, Netherlands.

Hebert et al., "The Molecular Dating Game: An Antibody Heavy Chain Hangs Loose with a Chaperone while Vaiting for Its Life Partner", Molecular Cell, 2009, pp. 635-636, vol. 34 No. 6, Cell Press, United States.

Ho et al., "Display and Selection of scFv antibodies on HEK-293T Cells", Methods of Molecular Biology, 2009, pp. 99-113, vol. 562.

International Preliminary Report on Patentability (Chapter I) for PCT/US2013/038497 dated Oct. 28, 2014.

International Search Report and Written Opinion for PCT/US2013/038497 dated Sep. 6, 2013.

Lorenzo et al., "Intracellular Localization of Vaccinia Virus Extracellular Enveloped Virus Envelope Proteins Individually Expressed Using a Semliki Forest Virus Replicon", Journal of Virology, 2000, pp. 10535-10550, vol. 74 No. 22, American Society for Microbiology, United States.

Office Action for U.S. Appl. No. 13/844,388 dated Jan. 13, 2015.

Office Action for U.S. Appl. No. 13/844,388 dated Sep. 25, 2015.

Roberts et al., "Vaccinia Virus Morphogenesis and Dissemination", Trends in Microbiology, 2008, pp. 472-479, vol. 16 No. 10, Elsevier Trends Journals, England.

Smith et al., "Nucleotide Sequence of 42 kbp of Vaccinia Virus Strain WR From Near the Right Inverted Terminal Repeat", Journal of General Virology, 1991, pp. 1349-1376, vol. 72, Great Britain.

Smith et al., "The Formation and Function of Extracellular Enveloped Vaccinia Virus", Journal of General Virology, 2002, pp. 2915-2931, vol. 83 Pt. 12, Society for General Microbiology, England.

USPTO, Applicant-Inititated Interview Summary issued in U.S. Appl. No. 14/977,067, dated Mar. 10, 2017, 3 pages.

USPTO, Final Office Action for U.S. Appl. No. 13/844,388 dated Feb. 9, 2017, 7 pages.

(56) References Cited

OTHER PUBLICATIONS

USPTO, Notice of Allowance issued in U.S. Appl. No. 14/977,067, dated Mar. 14, 2017, 10 pages.
Chou et al., "An Overview of the Vaccinia Virus Infectome: A Survey of the Proteins of the Poxvirus-Infected Cell", Journal of Virology, Feb. 2012, pp. 1487-1499, vol. 86, No. 3.
Chung et al., "Vaccinia Virus Proteome: Identification of Proteins in Vaccinia Virus Intracellular Mature Virion Particles", Journal of Virology, Mar. 2006, pp. 2127-2140, vol. 80, No. 5.
Carroll, M. et al., (1997), "Host Range and Cytopathogenicity of the Highly Attenuated MVA Strain of Vaccinia Virus: Propagation and Generation of Recombinant Viruses in a Nonhuman Mammalian Cell Line", Virology, 238: 198-211.
Colbére-Garapin, F., et al., (1981), "A new dominant hybrid selective marker for higher eukaryotic cells", Journal of Molecular Biology, vol. 150(1): 1-14.
Deng, L., et al., (2007), "Indentification of Novel Antipoxiral Agents: Mitoxantron Inhibits Vaccinia Virus Replication by Blocking Virion Assembly", Journal of Virology, vol. 81(24), pp. 13392-13402.
Earl, P., L., et al., (1990), "Removal of Cryptic Poxvirus Transcription Termination Signals from Human Immunodeficiency Virus Type 1 Envelope Gene Enhances Expression and Immunogenicity of a Recombinant Vaccinia Virus", Journal of Virology, vol. 64(5), 2448-2451.
Fenner, F. (1959), "Genetic studies with mammalian poxviruses: II. Recombination between two strains of vaccinia virus in single HeLa cells", Virology, vol. 8: 499-507.
Fenner, F., et al., (1958), "Genetic studies with mammalian poxviruses: I. Demonstration of recombination between two strains of vaccinia virus", Virology, vol. 5: 530-548.
International Search Report and Written Opinion dated Oct. 6, 2017 issued in PCT/US2017/044688.
Kotwal G., et al., (1988), "Analysis of a large cluster of nonessential genes deleted from a vaccinia virus terminal transposition mutant", Virology, vol. 167: 524-537.
Mayr, A., et al., (1975), "Abstammung, Eigenschaften und Verwendung des attenuierten Vaccinia-Stammes MVA", vol. 3(1), pp. 6-14—Available in German Only.
Merchlinsky, M., et al., (1997), "Construction and Characterization of Vaccinia Direct Ligation Vectors", Virology, 238: 444-451.
Moss, B., (1991), "Vaccinia virus: a tool for research and vaccine development", Science, vol. 252(5013), pp. 1662-1667.
Moss, B., et al., (1969), "Rifampicin: a Specific Inhibitor of Vaccinia Virus Assembly", Nature, vol. 224, pp. 1280-1284.
Mulligan, R. C. et al., (1981), "Selection for animal cells that express the *Escherichia coli* gene coding for xanthine-guanine phosphoribosyltransferase", Proc. Natl. Acad. Sci. USA vol. 78(4): 2072-2076.
O'Hare, K.., et al., (1981), "Transformation of mouse fibroblasts to methotrexate resistance by a recombinant plasmid expressing a prokaryotic dihydrofolate reductase", Proc. Natl. Acad. Sci. USA, vol. 78(3): 1527-1531.
Perkus, M., et al., (1986), "Insertion and deletion mutants of vaccinia virus", Virology, vol. 152(2): 285-297.
Santerre, R., et al., (1984), "Expression of prokaryotic genes for hygromycin B and G418 resistance as dominant-selection markers in mouse L cells", Gene, vol. 30: 147-156.
Scheiflinger, F., et al., (1992), "Construction of chimeric vaccinia viruses by molecular cloning and packaging",Proc. Natl. Acad. Sci. USA, Biochemistry, vol. 89, pp. 9977-9981.
Smith, E., et al., (2001), "Lethality-Based Selection of Recombinant Genes in Mammalian Cells: Application to Identifying Tumor Antigens" Nature Medicine, 7(8): 967-972.
Sodeik, B., et al., (1994), "Assembly of Vaccinia Virus: Effects of Rifampin on the Intracellular Distribution of Viral Protein p65", Journal of Virology, vol. 68(2), pp. 1103-1114.
Sutter, G., et al., (1992), "Nonreplicating vaccinia vector efficiently expresses recombinant genes", Proc. Natl. Acad. Sci. USA, vol. 89: 10847-10851.
Syzbalska, E., et al., (1962), "Genetics of Human Cell Lines, IV. DNA-Mediated Heritable Transformation of a Biochemical Trait", Proc. Natl. Acad. Sci. USA, vol. 48: 2026-2034.
Wigler M., et al., (1980), "Transformation of mammalian cells with an amplifiable dominant-acting gene", Proc. Natl. Acad. Sci. USA, vol. 77(6): 3567-3570.
Wigler, M. et al., (1977), "Transfer of purified herpes virus thymidine kinase gene to cultured mouse cells", Cell, vol. 11(1): 223-232.

"pJEM1"

AAAAAATGAAAATAAATACAAAGGTTCTTGAGGGTTGTGTTAAATTGAAAGCGAGAAATAATCATAAA
TTCCATGGGATGGAGCTGTATCATCCTCTTCTTGGTAGCAACAGCTACAG*GCGCGC*ACTCCGAGATCC
AGCTGGTGCAGAGCGGCCCTGAGCTGAAGCAGCCTGGCGAGACCGTGAGGATCAGCTGCAAGGCCAGC
GGCTACACCTTCACCAACTACGGCATGAACTGGGTGAAGCAGGCCCCTGGCAAGGGCCTGAAGTGGAT
GGGCTGGATCAACACCTACACCGGCGAGCCTACCTACGCCGCCGACTTCAAGAGGAGGTTCACCTTCA
GCCTGGAGACCAGCGCCAGCACCGCCTACCTGCAGATCAGCAACCTGAAGAACGACGACACCGCCACC
TACTTCTGCGCCAAGTACCCTCACTACTACGGCAGCAGCCACTGGTACTTCGACGTGTGGGGCGCCGG
CACCAC*GGTCACC*GTCTCCTCAGCCTCCACCAAGGGCCCATCGGTCTTCCCCCTGGCACCCTCCTCCA
AGAGCACCTCTGGGGGCACAGCGGCCCTGGGCTGCCTGGTCAAGGACTACTTCCCCGAACCGGTGACG
GTGTCGTGGAACTCAGGCGCCCTGACCAGCGGCGTGCACACCTTCCCGGCTGTCCTACAGTCCTCAGG
ACTCTACTCCCTCAGCAGCGTCGTGACCGTGCCCTCCAGCAGCTTGGGCACCCAGACCTACATCTGCA
ACGTGAATCACAAGCCCAGCAACACCAAGGTGGACAAGAAAGTTACATCAACTACAAATGACACTGAT
AAAGTAGATTATGAAGAATACTCCACAGAGTTGATTGTAAATACAGATAGTGAATCGACTATAGACAT
AATACTATCTGGATCTACACATTCACCGGAAACTAGTTCTAAGAAACCTGATTATATAGATAATTCTA
ATTGCTCGTCGGTATTCGAAATCGCGACTCCGGAACCAATTACTGATAATGTAGAAGATCATACAGAC
ACCGTCACATACACTAGTGATAGCATTAATACAGTAAGTGCATCATCTGGAGAATCCACAACAGACGA
GACTCCGGAACCAATTACTGATAAAGAAGATCATACAGTTACAGACACTGTCTCATACACTACAGTAA
GTACATCATCTGGAATTGTCACTACTAAATCAACCACCGATGATGCGGATCTTTATGATACGTACAAT
GATAATGATACAGTACCACCAACTACTGTAGGCGGTAGTACAACCTCTATTAGCAATTATAAAACCAA
GGACTTTGTAGAAATATTTGGTATTACCGCATTAATTATATTGTCGGCCGTGGCAATTTTCTGTATTA
CATATTATATATAATAAACGTTCACGTAAATACAAAACAGAGAACAAAGTCTAG
(SEQ ID NO: 1)

Double underline — H5 promoter
Single underline — Leader peptide
Squiggly underline — Representative Heavy Variable region
B A
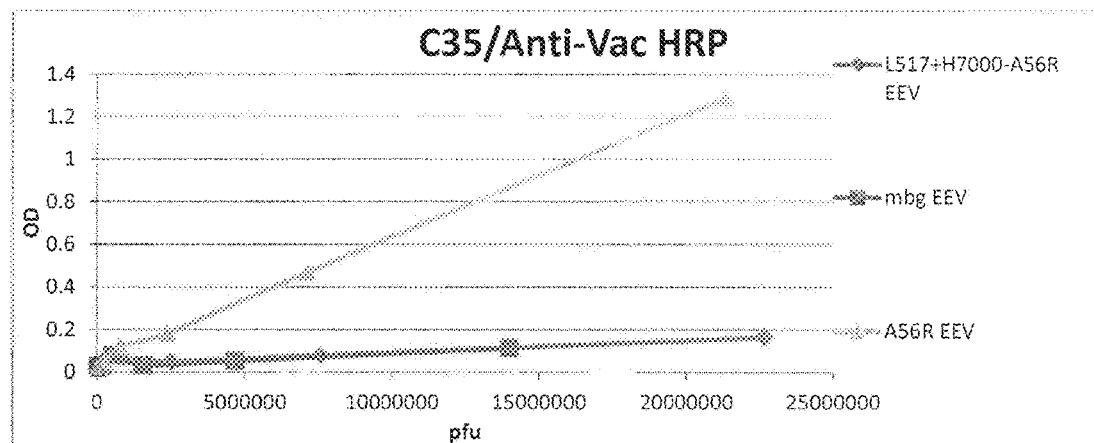
B
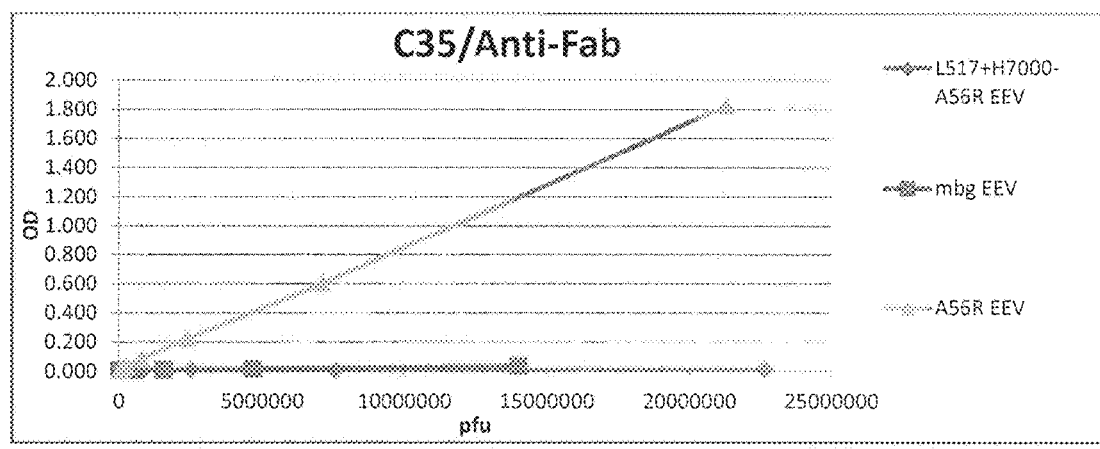
FIGURE 4

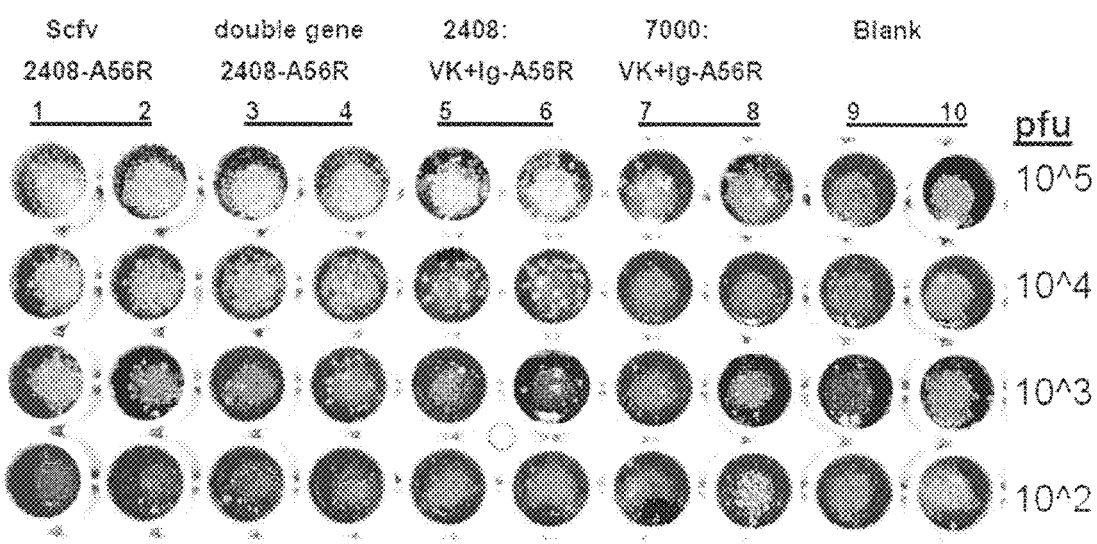
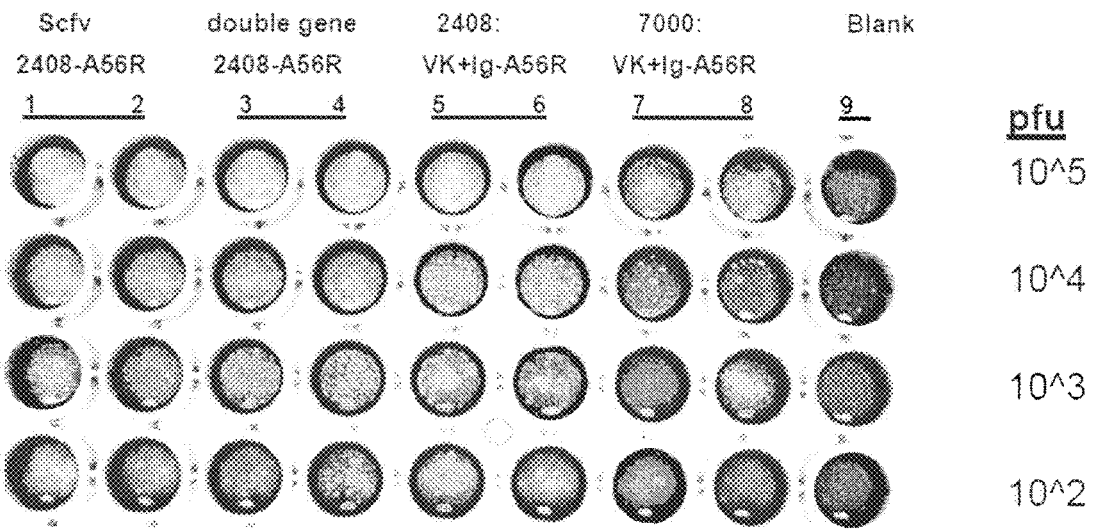
FIGURE 5A-B

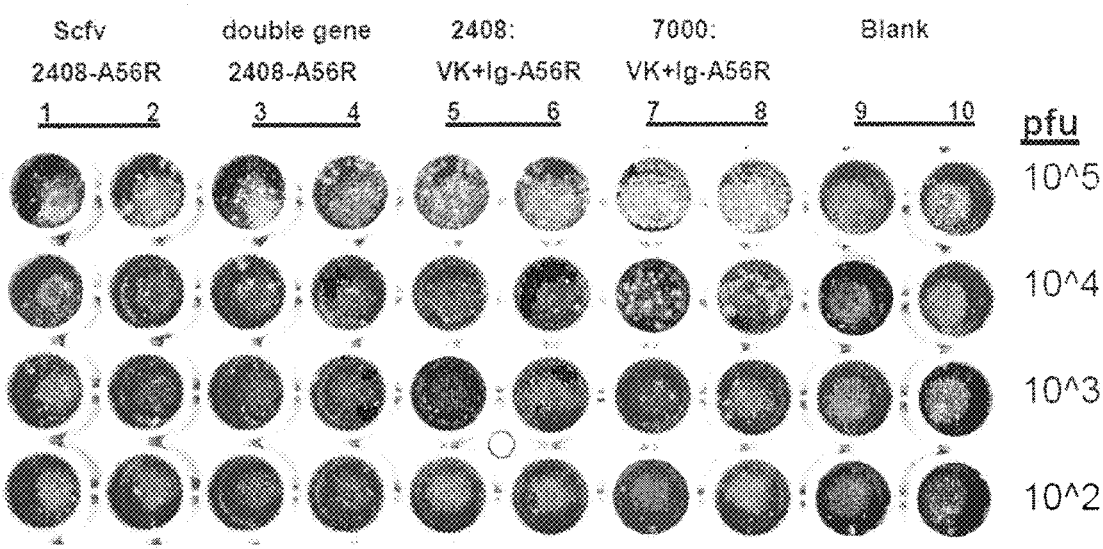
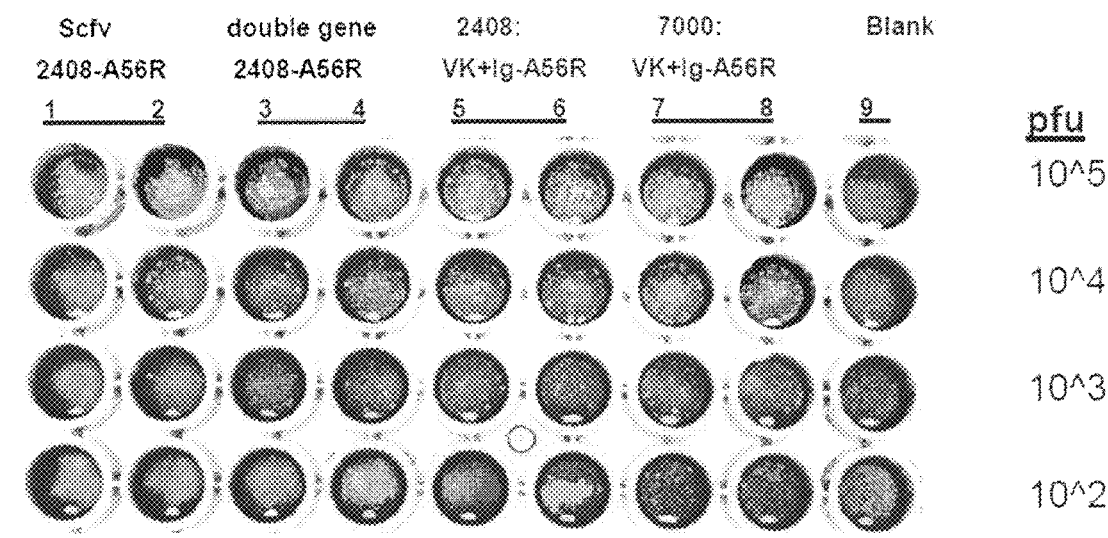
FIGURE 5C-D

Alignment:

>VH3-11

Identities = 81/98 (82%), Positives = 88/98 (89%)

```
C. 20:  1   EVQLVESGGGLVKPGGSLRLSCAASGFIFTDYYLSWIRQAPGKGPEWLSYISSYSRYINY  60
            +VQLVESGGGLVKPGGSLRLSCAASGF F+DYY+SWIRQAPGKG EW+SYISS      Y
VH311:  1   QVQLVESGGGLVKPGGSLRLSCAASGFTFSDYYMSWIRQAPGKGLEWVSYISSSGSTIYY  60

C. 20:  61  ADSVKGRFTISRDNTRNSIYLQMNNLRVEDTAVYYCAR  98    (SEQ ID NO: 33)
            ADSVKGRFTISRDN +NS+YLQMN+LR EDTAVYYCAR         (SEQ ID NO: 34)
VH311:  61  ADSVKGRFTISRDNAKNSLYLQMNSLRAEDTAVYYCAR  98    (SEQ ID NO: 35)
```

FIG. 7

Her2 B10 clone Sequence

EVQLLESGGGFVQPGGSLRLSCAASGFAFNNYALSWVRQAPGRGLKWVSAISPDGDYIYYAD
SVKGRFIFSRDNSRNMLSLQMTSLGAEDTALYYCARQNNVRDGAVAGPLDHWGQGTLVT (SEQ ID NO: 20)

```
>IGHV3-23*01

Identities = 77/98 (78%), Positives = 85/98 (86%)
B10    1   EVQLLESGGGFVQPGGSLRLSCAASGFAFNNYALSWVRQAPGRGLKWVSAISPDGDYIYY    60
           EVQLLESGGG VQPGGSLRLSCAASGF ++YA+SWVRQAPG+GL+WVSAIS  G    YY
VH323  1   EVQLLESGGGLVQPGGSLRLSCAASGFTFSSYAMSWVRQAPGKGLEWVSAISGSGGSTYY    60

B10   61   ADSVKGRFIFSRDNSRNMLSLQMTSLGAEDTALYYCAR    98  (SEQ ID NO: 36)
           ADSVKGRF  SRDNS+N L LQM SL AEDTA+YYCA+        (SEQ ID NO: 37)
VH323 61   ADSVKGRFTISRDNSKNTLYLQMNSLRAEDTAVYYCAK    98  (SEQ ID NO: 38)
```

FIG. 11

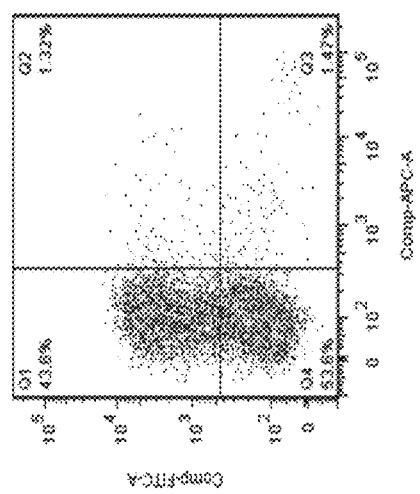 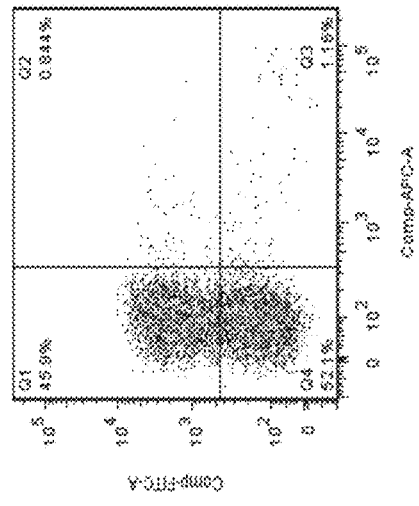
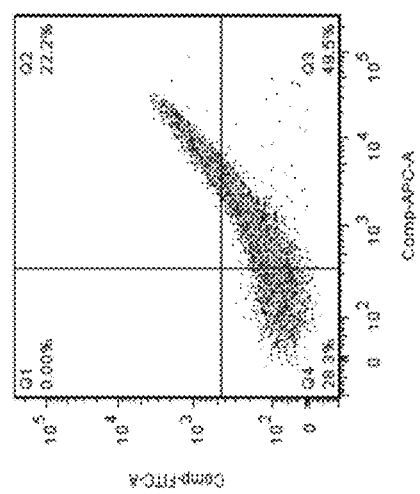 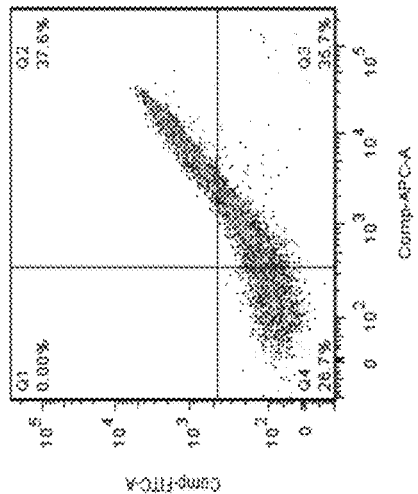
FIG. 14

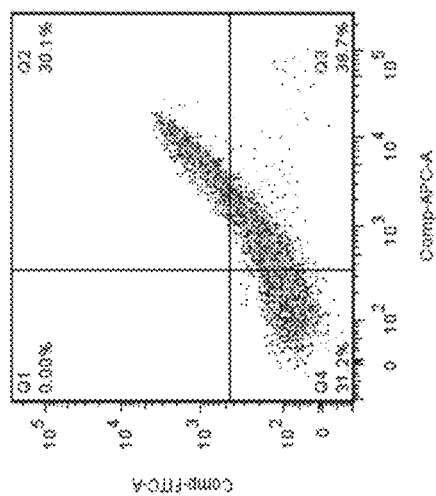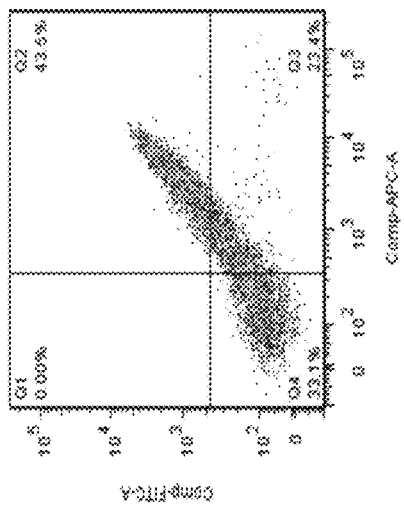
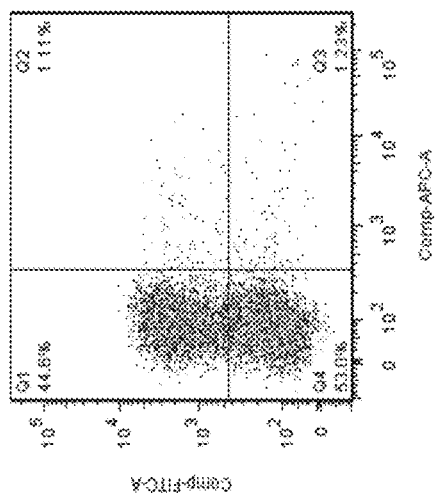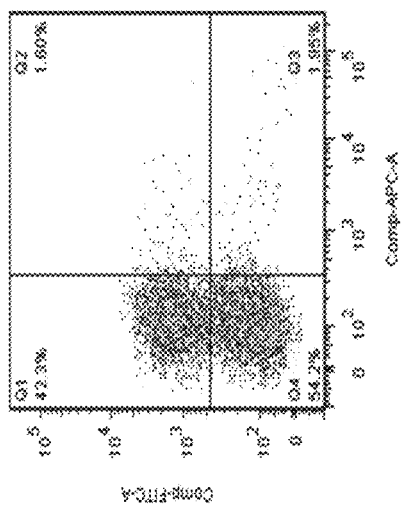
A. H2124-IgG L517
B. H2124-TR L517
FIG. 15

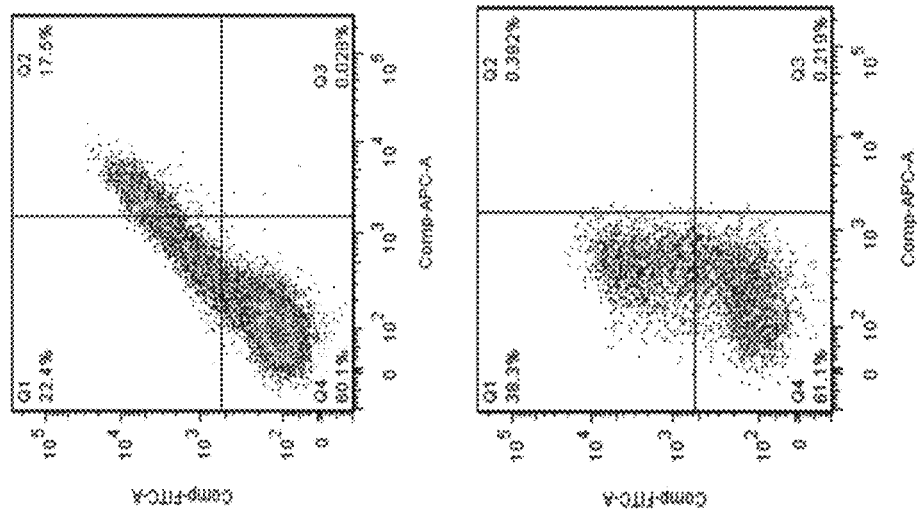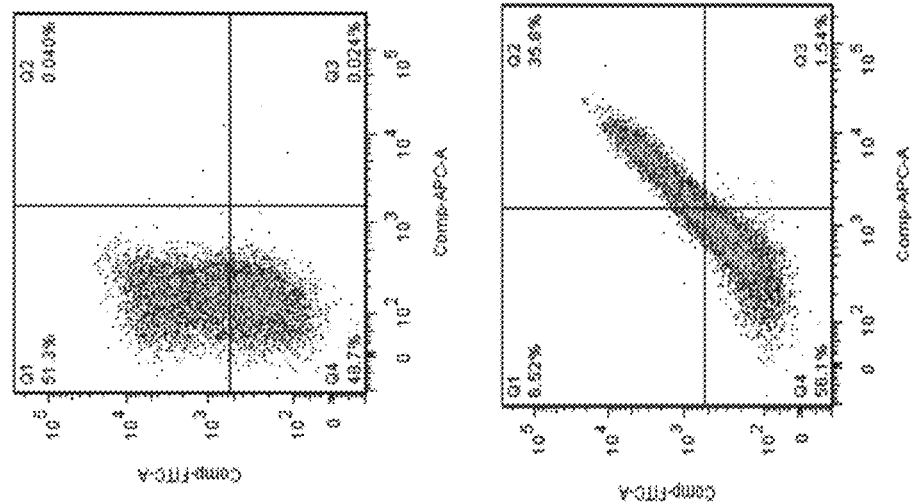
FIG. 16

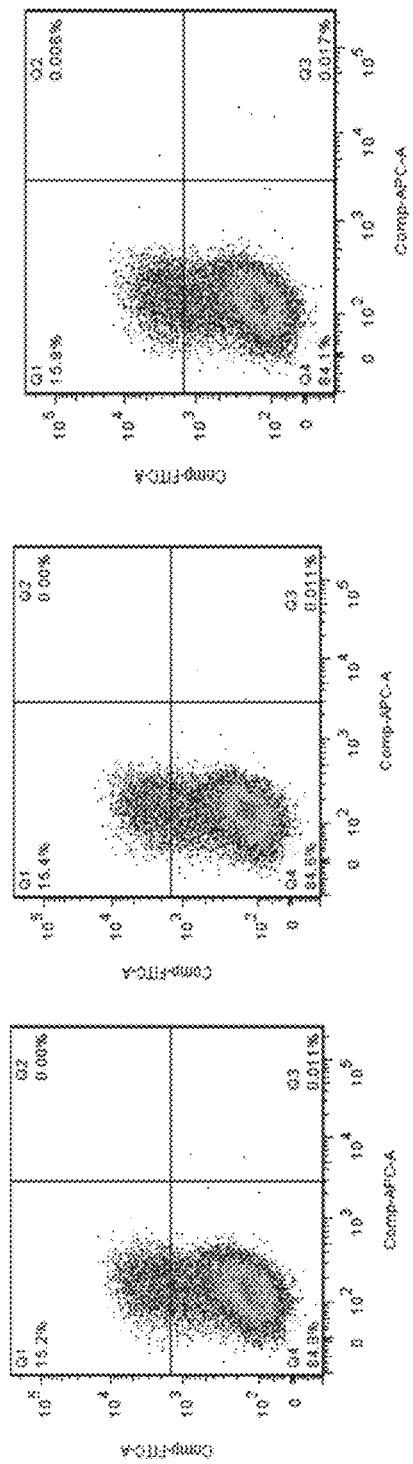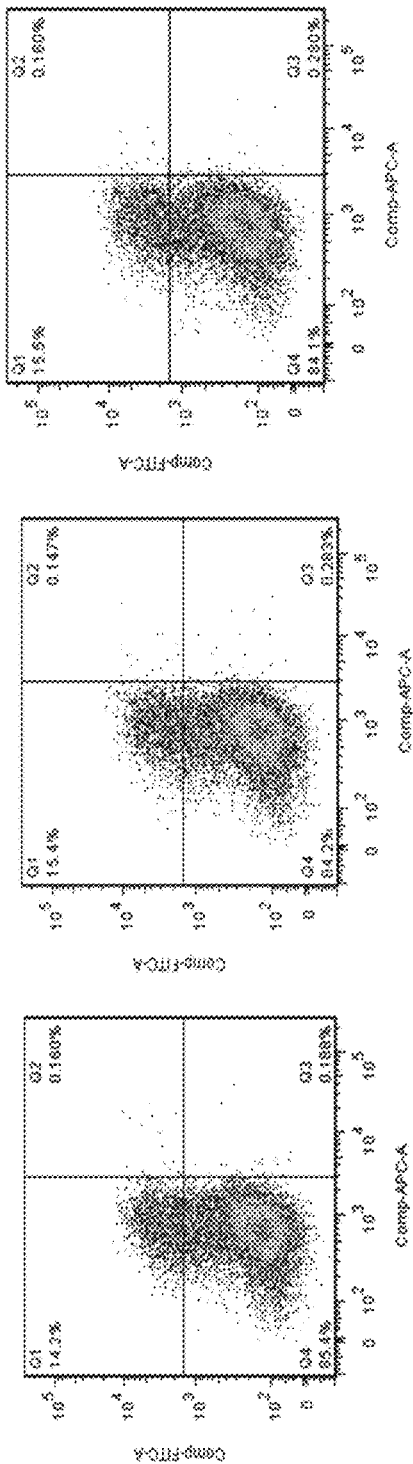
FIG. 17

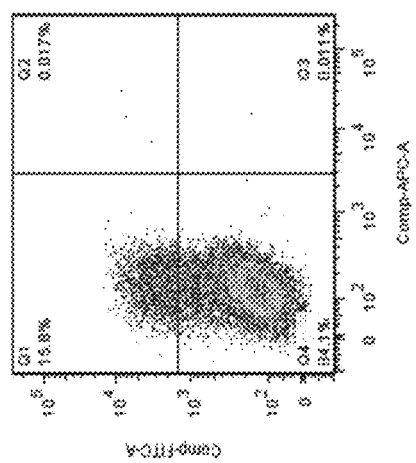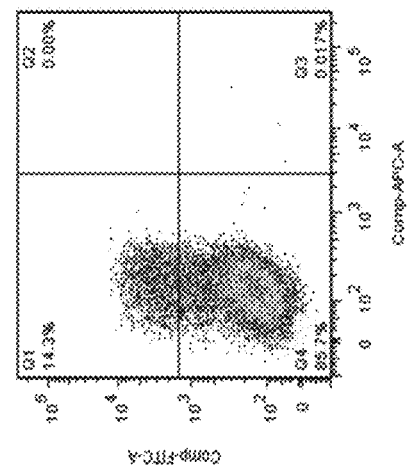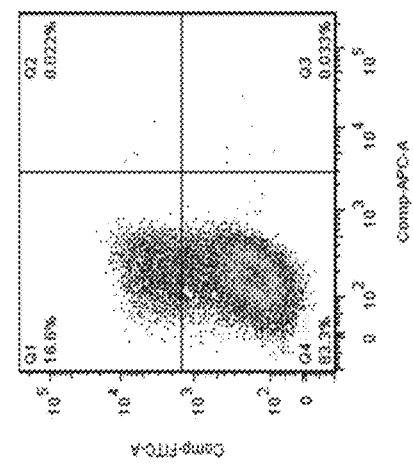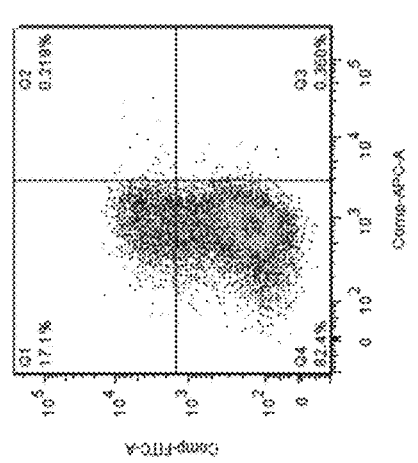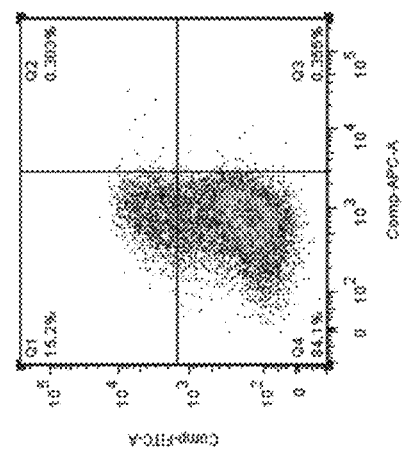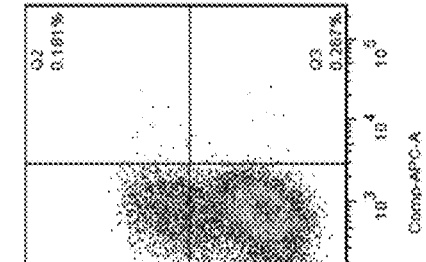
FIG. 18

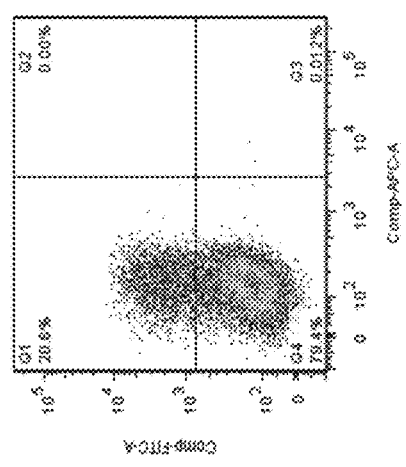 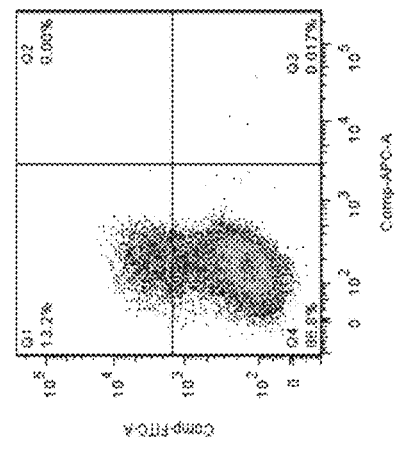 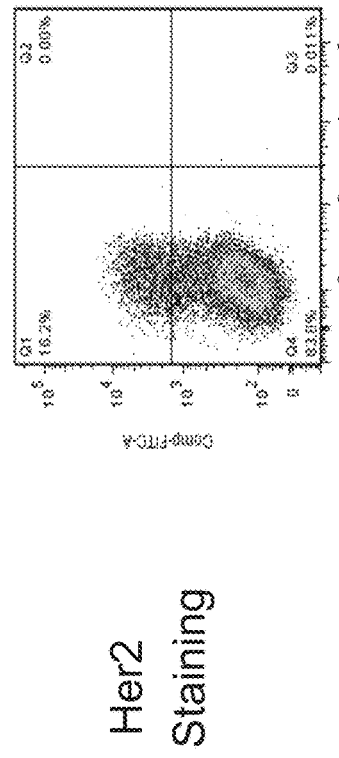
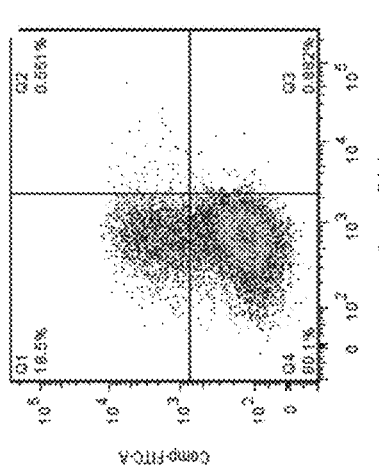 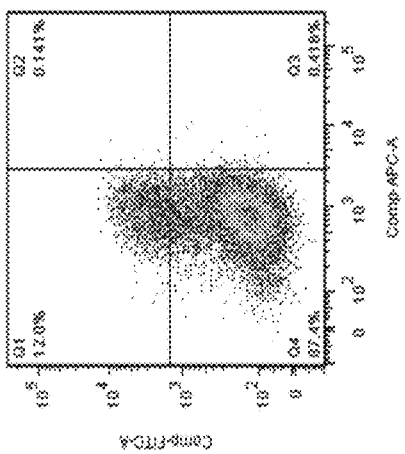 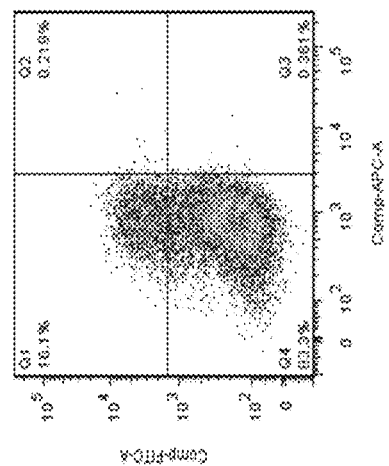
FIG. 19

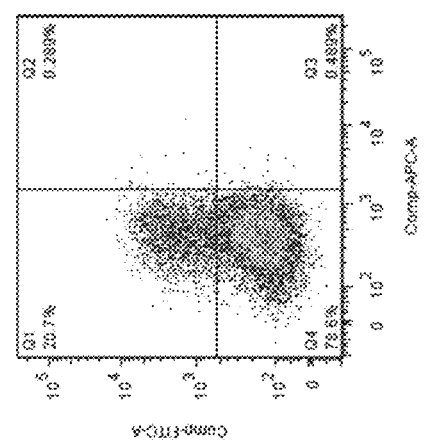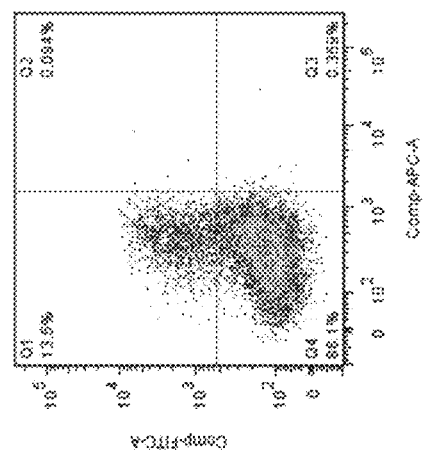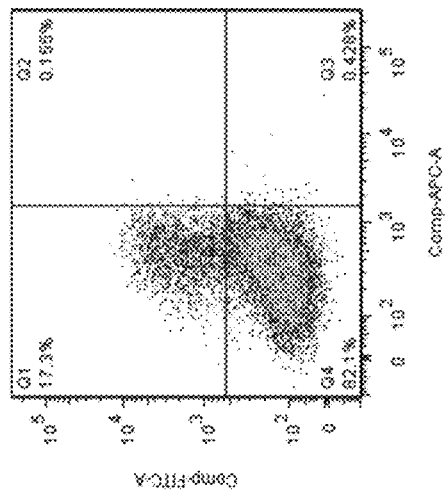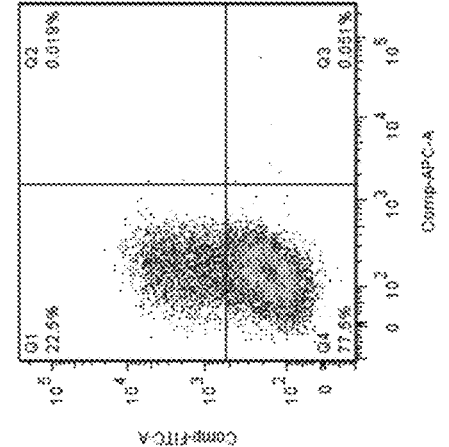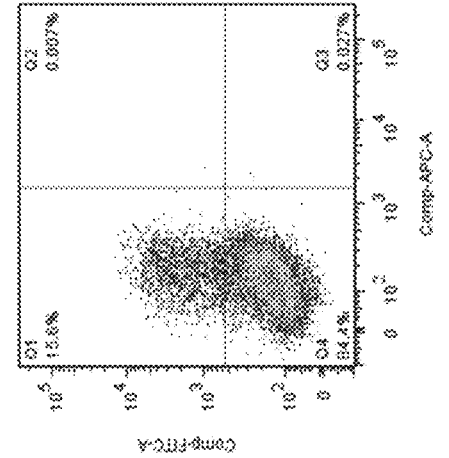
FIG. 21

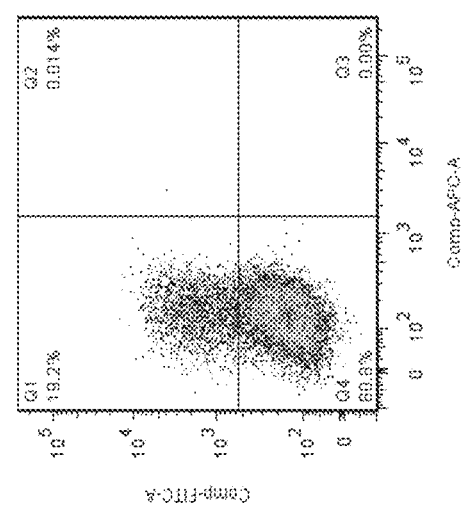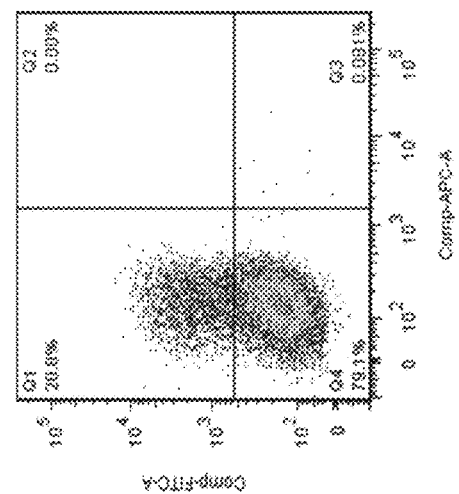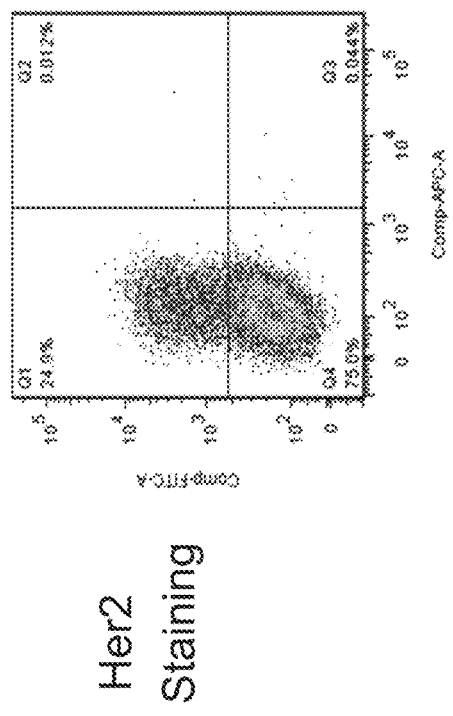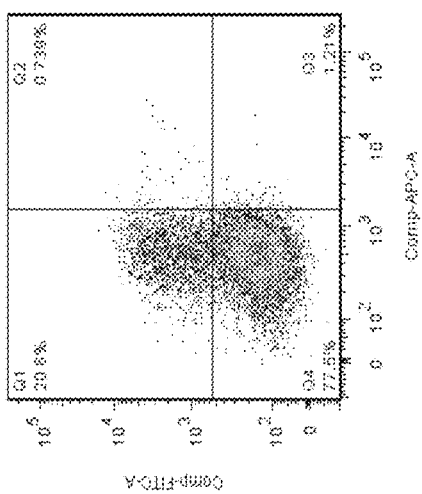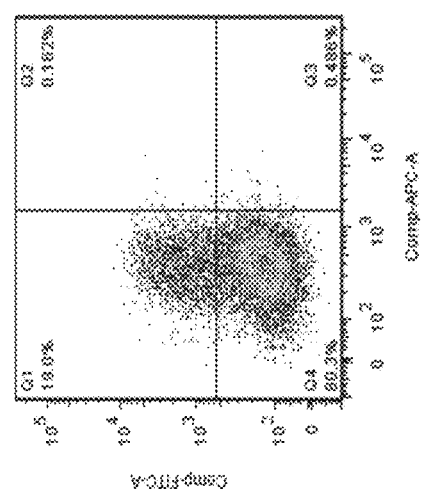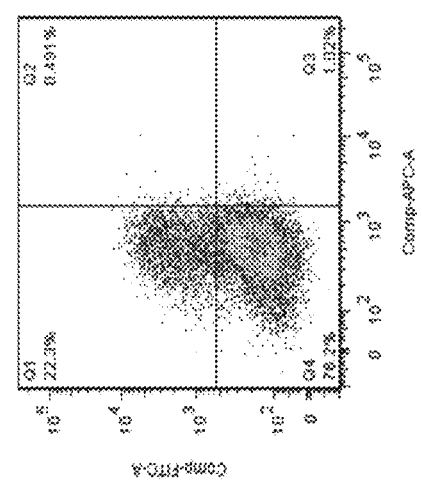
FIG. 22

- mAb 2050  VH5-51 synthetic
- mAb 2063  VH3-30 naïve
- mAb 2110  VH3-7 naïve
- Specific to native CD100 on Jurkat cells with low binding to background on BxPC3
A. mAb2050
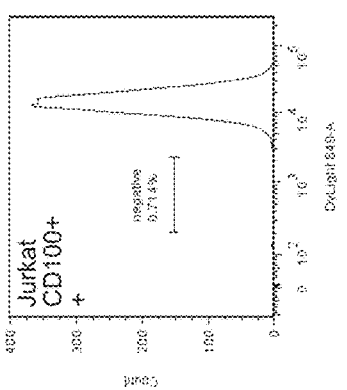
B. mAb2063
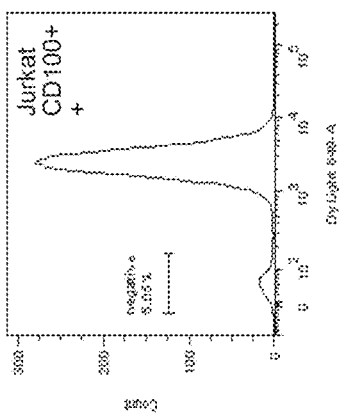
C. mAb2110
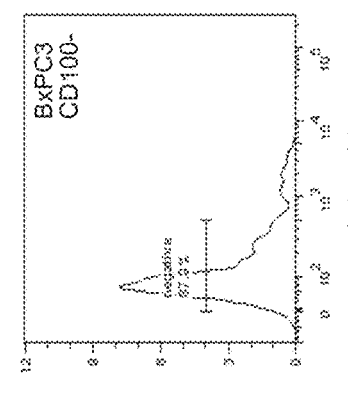
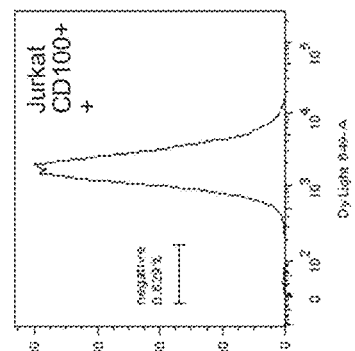
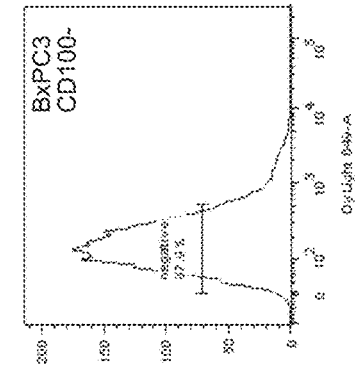
FIG. 26

SEQUENCE LISTING

```
<160> NUMBER OF SEQ ID NOS: 32

<210> SEQ ID NO 1
<211> LENGTH: 1416
<212> TYPE: DNA
<213> ORGANISM: Artificial sequence
<220> FEATURE:
<223> OTHER INFORMATION: pJEM1 transfer plasmid

<400> SEQUENCE: 1
aaaaaatgaa aataaataca aaggttcttg agggttgtgt taaattgaaa gcgagaaata      60
atcataaatt ccatgggatg gagctgtatc atcctcttct tggtagcaac agctacaggc     120
gcgcactccg agatccagct ggtgcagagc ggccctgagc tgaagcagcc tggcgagacc     180
```

```
gtgaggatca gctgcaaggc cagcggctac accttcacca actacggcat gaactgggtg    240
aagcaggccc ctggcaaggg cctgaagtgg atgggctgga tcaacaccta caccggcgag    300
cctacctacg ccgccgactt caagaggagg ttcaccttca gcctggagac cagcgccagc    360
accgcctacc tgcagatcag caacctgaag aacgacgaca ccgccaccta cttctgcgcc    420 aagtacccte actactacgg cagcagccac tggtacttcg acgtgtgggg cgccggcacc    480
acggtcaccg tctcctcagc ctccaccaag ggcccatcgg tcttccccct ggcaccctcc    540
tccaagagca cctctggggg cacagcggcc ctgggctgcc tggtcaagga ctacttcccc    600
gaaccggtga cggtgtcgtg gaactcaggc gccctgacca gcggcgtgca caccttcccg    660
gctgtcctac agtcctcagg actctactcc ctcagcagcg tcgtgaccgt gccctccagc    720
agcttgggca cccagaccta catctgcaac gtgaatcaca agcccagcaa caccaaggtg    780
gacaagaaag ttacatcaac tacaaatgac actgataaag tagattatga agaatactcc    840
acagagttga ttgtaaatac agatagtgaa tcgactatag acataatact atctggatct    900
acacattcac cggaaactag ttctaagaaa cctgattata tagataattc taattgctcg    960
tcggtattcg aaatcgcgac tccggaacca attactgata atgtagaaga tcatacagac   1020
accgtcacat acactagtga tagcattaat acagtaagtg catcatctgg agaatccaca   1080
acagacgaga ctccggaacc aattactgat aagaagatc atacagttac agacactgtc    1140
tcatacacta cagtaagtac atcatctgga attgtcacta ctaaatcaac caccgatgat   1200
gcggatcttt atgatacgta caatgataat gatacagtac caccaactac tgtaggcggt   1260
agtacaacct ctattagcaa ttataaaacc aaggactttg tagaaatatt tggtattacc   1320
gcattaatta tattgtcggc cgtggcaatt ttctgtatta catattatat atataataaa   1380
cgttcacgta aatacaaaac agagaacaaa gtctag                             1416

<210> SEQ ID NO 2
<211> LENGTH: 446
<212> TYPE: DNA
<213> ORGANISM: Artificial sequence
<220> FEATURE:
<223> OTHER INFORMATION: pVKE transfer plasmid

<400> SEQUENCE: 2
ggccaaaaat tgaaaaacta gatctattta ttgcacgcgg ccgcccatgg gatggagctg     60
tatcatcctc ttcttggtag caacagctac aggcgtgcac ttgactcgag atcaaacgaa    120
ctgtggctgc accatctgtc ttcatcttcc cgccatctga tgagcagttg aaatctggaa    180
ctgcctctgt tgtgtgcctg ctgaataact tctatcccag agaggccaaa gtacagtgga    240
aggtggataa cgccctccaa tcgggtaact cccaggagag tgtcacagag caggacagca    300
aggacagcac ctacagcctc agcagcaccc tgacgctgag caaagcagac tacgagaaac    360
acaaagtcta cgcctgcgaa gtcacccatc agggcctgag ctcgcccgtc acaaagagct    420
tcaacagggg agagtgttag gtcgac                                         446

<210> SEQ ID NO 3
<211> LENGTH: 455
<212> TYPE: DNA
<213> ORGANISM: Artificial sequence
<220> FEATURE:
<223> OTHER INFORMATION: pVLE transfer plasmid

<400> SEQUENCE: 3
```

-continued

```
ggccaaaaat tgaaaaacta gatctattta ttgcacgcgg ccgcccatgg gatggagctg      60
tatcatcctc ttcttggtag caacagctac aggcgtgcac ttgactcgag aagcttaccg     120
tcctacgaac tgtggctgca ccatctgtct tcatcttccc gccatctgat gagcagttga     180
aatctggaac tgcctctgtt gtgtgcctgc tgaataactt ctatcccaga gaggccaaag     240
tacagtggaa ggtggataac gccctccaat cgggtaactc ccaggagagt gtcacagagc     300
aggacagcaa ggacagcacc tacagcctca gcagcaccct gacgctgagc aaagcagact     360
acgagaaaca caaagtctac gcctgcgaag tcacccatca gggcctgagc tcgcccgtca     420
caaagagctt caacagggga gagtgttagg tcgac                                455
```

<210> SEQ ID NO 4
<211> LENGTH: 29
<212> TYPE: DNA
<213> ORGANISM: Artificial sequence
<220> FEATURE:
<223> OTHER INFORMATION: 5' primer huCgamma1-5B:

<400> SEQUENCE: 4

```
attaggatcc ggtcaccgtc tcctcagcc                                        29
```

<210> SEQ ID NO 5
<211> LENGTH: 33
<212> TYPE: DNA
<213> ORGANISM: Artificial sequence
<220> FEATURE:
<223> OTHER INFORMATION: 3' primer huCgamma1-3S:

<400> SEQUENCE: 5

```
attagtcgac tcatttaccg gagacaggga gag                                   33
```

<210> SEQ ID NO 6
<211> LENGTH: 33
<212> TYPE: DNA
<213> ORGANISM: Artificial sequence
<220> FEATURE:
<223> OTHER INFORMATION: CH1(F):

<400> SEQUENCE: 6

```
caagggaccc tggtcaccgt ctcctcagcc tcc                                   33
```

<210> SEQ ID NO 7
<211> LENGTH: 25
<212> TYPE: DNA
<213> ORGANISM: Artificial sequence
<220> FEATURE:
<223> OTHER INFORMATION: CH1(R):

<400> SEQUENCE: 7

```
aactttcttg tccaccttgg tgttg                                            25
```

<210> SEQ ID NO 8
<211> LENGTH: 51
<212> TYPE: DNA
<213> ORGANISM: Artificial sequence
<220> FEATURE:
<223> OTHER INFORMATION: A56R(F):

<400> SEQUENCE: 8

```
caacaccaag gtggacaaga aagttacatc aactacaaat gacactgata g              51
```

<210> SEQ ID NO 9
<211> LENGTH: 40

<210> SEQ ID NO 9
<211> LENGTH: 40
<212> TYPE: DNA
<213> ORGANISM: Artificial sequence
<220> FEATURE:
<223> OTHER INFORMATION: A56R(R):

<400> SEQUENCE: 9

```
tatagtcgac ctagactttg ttctctgttt tgtatttacg                              40
```

<210> SEQ ID NO 10
<211> LENGTH: 1266
<212> TYPE: DNA
<213> ORGANISM: Artificial sequence
<220> FEATURE:
<223> OTHER INFORMATION: VH (H2124)-CH1-A56R Fab Product Fusion Protein

<400> SEQUENCE: 10

```
caggtgcagc tgcagcagtg gggcgcagga ctgctgaagc ctagcgagac cctgtccctc        60
acctgcgctg tctatggcta ctccatcacc agcggctatt ctggaactg  atccgccag        120
cccccaggga aggggctgga gtggattggg tacatcagct acgacggcag cagcaactcc       180
aacccatctc tcaaaaatag ggtcacaatc agcagagaca cctccaagaa ccagttctcc       240
ctgaagctga gctctgtgac cgccgccgac accgctgtgt attactgtgc cagaggaact       300
accgggtttg cttactgggg ccaagggacc ctggtcaccg tctcctcagc ctccaccaag       360
ggcccatcgg tcttccccct ggcaccctcc tccaagagca cctctggggg cacagcggcc       420
ctgggctgcc tggtcaagga ctacttcccc gaaccggtga cggtgtcgtg gaactcaggc       480
gccctgacca gcggcgtgca caccttcccg gctgtcctac agtcctcagg actctactcc       540
ctcagcagcg tcgtgaccgt gccctccagc agcttgggca cccagaccta catctgcaac       600
gtgaatcaca gcccagcaa  caccaaggtg gacaagaaag ttacatcaac tacaaatgac       660
actgataaag tagattatga agaatactcc acagagttga ttgtaaatac agatagtgaa       720
tcgactatag acataatact atctggatct acacattcac cggaaactag ttctaagaaa       780
cctgattata tagataattc taattgctcg tcggtattcg aaatcgcgac tccggaacca       840
attactgata tgtagaaga  tcatacagac accgtcacat acactagtga tagcattaat       900
acagtaagtg catcatctgg agaatccaca acagacgaga ctccggaacc aattactgat       960
aaagaagatc atacagttac agacactgtc tcatacacta cagtaagtac atcatctgga      1020
attgtcacta ctaaatcaac caccgatgat gcggatcttt atgatacgta caatgataat      1080
gatacagtac caccaactac tgtaggcggt agtacaacct ctattagcaa ttataaaacc      1140
aaggactttg tagaaatatt tggtattacc gcattaatta tattgtcggc cgtggcaatt      1200
ttctgtatta catattatat atataataaa cgttcacgta aatacaaaac agagaacaaa      1260
gtctag                                                                 1266
```

<210> SEQ ID NO 11
<211> LENGTH: 421
<212> TYPE: PRT
<213> ORGANISM: Artificial sequence
<220> FEATURE:
<223> OTHER INFORMATION: VH (H2124)-CH1-A56R Fab Product Fusion Protein

<400> SEQUENCE: 11

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Ile Thr Ser Gly
            20                  25                  30
```

Tyr Phe Trp Asn Trp Ile Arg Gln Pro Pro Gly Lys Gly Leu Glu Trp
             35                  40                  45

Ile Gly Tyr Ile Ser Tyr Asp Gly Ser Ser Asn Ser Asn Pro Ser Leu
 50                  55                  60

Lys Asn Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Thr Thr Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Thr Ser Thr Asn Thr Asp Lys Val
210                 215                 220

Asp Tyr Glu Glu Tyr Ser Thr Glu Leu Ile Val Asn Thr Asp Ser Glu
225                 230                 235                 240

Ser Thr Ile Asp Ile Ile Leu Ser Gly Ser Thr His Ser Pro Glu Thr
                245                 250                 255

Ser Ser Lys Lys Pro Asp Tyr Ile Asp Asn Ser Asn Cys Ser Ser Val
            260                 265                 270

Phe Glu Ile Ala Thr Pro Glu Pro Ile Thr Asp Asn Val Glu Asp His
        275                 280                 285

Thr Asp Thr Val Thr Tyr Thr Ser Asp Ser Ile Asn Thr Val Ser Ala
290                 295                 300

Ser Ser Gly Glu Ser Thr Thr Asp Glu Thr Pro Glu Pro Ile Thr Asp
305                 310                 315                 320

Lys Glu Asp His Thr Val Thr Asp Thr Val Ser Tyr Thr Thr Val Ser
                325                 330                 335

Thr Ser Ser Gly Ile Val Thr Thr Lys Ser Thr Thr Asp Asp Ala Asp
            340                 345                 350

Leu Tyr Asp Thr Tyr Asn Asp Asn Asp Thr Val Pro Pro Thr Thr Val
        355                 360                 365

Gly Gly Ser Thr Thr Ser Ile Ser Asn Tyr Lys Thr Lys Asp Phe Val
370                 375                 380

Glu Ile Phe Gly Ile Thr Ala Leu Ile Ile Leu Ser Ala Val Ala Ile
385                 390                 395                 400

Phe Cys Ile Thr Tyr Tyr Ile Tyr Asn Lys Arg Ser Arg Lys Tyr Lys
                405                 410                 415

Thr Glu Asn Lys Val
            420

<210> SEQ ID NO 12
<211> LENGTH: 39
<212> TYPE: DNA

```
<213> ORGANISM: Artificial sequence
<220> FEATURE:
<223> OTHER INFORMATION: Sense VH 3 primer

<400> SEQUENCE: 12
aatatgcgcg cactccgagg tgcagctggt ggagtctgg                    39

<210> SEQ ID NO 13
<211> LENGTH: 39
<212> TYPE: DNA
<213> ORGANISM: Artificial sequence
<220> FEATURE:
<223> OTHER INFORMATION: Sense VH 3a primer

<400> SEQUENCE: 13
aatatgcgcg cactccgagg tgcagctgtt ggagtctgg                    39

<210> SEQ ID NO 14
<211> LENGTH: 29
<212> TYPE: DNA
<213> ORGANISM: Artificial sequence
<220> FEATURE:
<223> OTHER INFORMATION: Antisense JH 1 primer

<400> SEQUENCE: 14
gagacggtga ccagggtgcc ctggcccca                              29

<210> SEQ ID NO 15
<211> LENGTH: 29
<212> TYPE: DNA
<213> ORGANISM: Artificial sequence
<220> FEATURE:
<223> OTHER INFORMATION: Antisense JH 2 primer

<400> SEQUENCE: 15
gagacggtga ccagggtgcc acggcccca                              29

<210> SEQ ID NO 16
<211> LENGTH: 29
<212> TYPE: DNA
<213> ORGANISM: Artificial sequence
<220> FEATURE:
<223> OTHER INFORMATION: Antisense JH 3 primer

<400> SEQUENCE: 16
gagacggtga ccattgtccc ttggcccca                              29

<210> SEQ ID NO 17
<211> LENGTH: 29
<212> TYPE: DNA
<213> ORGANISM: Artificial sequence
<220> FEATURE:
<223> OTHER INFORMATION: Antisense JH 4/5 primer

<400> SEQUENCE: 17
gagacggtga ccagggttcc ctggcccca                              29

<210> SEQ ID NO 18
<211> LENGTH: 29
<212> TYPE: DNA
<213> ORGANISM: Artificial sequence
<220> FEATURE:
<223> OTHER INFORMATION: Antisense JH 6 primer

<400> SEQUENCE: 18
gagacggtga ccgtggtccc ttggcccca                              29
```

<210> SEQ ID NO 19
<211> LENGTH: 113
<212> TYPE: PRT
<213> ORGANISM: Artificial sequence
<220> FEATURE:
<223> OTHER INFORMATION: variable heavy chain

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Thr Asp Tyr
            20                  25                  30

Tyr Leu Ser Trp Ile Arg Gln Ala Pro Gly Lys Gly Pro Glu Trp Leu
        35                  40                  45

Ser Tyr Ile Ser Ser Tyr Ser Arg Tyr Thr Asn Tyr Ala Asp Ser Val
    50                  55                  60

Lys Gly Arg Phe Thr Ile Ser Arg Asp Asn Thr Arg Asn Ser Ile Tyr
65                  70                  75                  80

Leu Gln Met Asn Asn Leu Arg Val Glu Asp Thr Ala Val Tyr Tyr Cys
                85                  90                  95

Ala Arg Ala Gly Ser Tyr Tyr Gly Tyr Trp Gly Gln Gly Thr Leu Val
            100                 105                 110

Thr

<210> SEQ ID NO 20
<211> LENGTH: 121
<212> TYPE: PRT
<213> ORGANISM: Artificial sequence
<220> FEATURE:
<223> OTHER INFORMATION: Her2 B10 clone

<400> SEQUENCE: 20

Glu Val Gln Leu Leu Glu Ser Gly Gly Gly Phe Val Gln Pro Gly Gly
1               5                   10                  15

Ser Leu Arg Leu Ser Cys Ala Ala Ser Gly Phe Ala Phe Asn Asn Tyr
            20                  25                  30

Ala Leu Ser Trp Val Arg Gln Ala Pro Gly Arg Gly Leu Lys Trp Val
        35                  40                  45

Ser Ala Ile Ser Pro Asp Gly Asp Tyr Ile Tyr Tyr Ala Asp Ser Val
    50                  55                  60

Lys Gly Arg Phe Ile Phe Ser Arg Asp Asn Ser Arg Asn Met Leu Ser
65                  70                  75                  80

Leu Gln Met Thr Ser Leu Gly Ala Glu Asp Thr Ala Leu Tyr Tyr Cys
                85                  90                  95

Ala Arg Gln Asn Asn Val Arg Asp Gly Ala Val Ala Gly Pro Leu Asp
            100                 105                 110

His Trp Gly Gln Gly Thr Leu Val Thr
        115                 120

<210> SEQ ID NO 21
<211> LENGTH: 51
<212> TYPE: DNA
<213> ORGANISM: Artificial sequence
<220> FEATURE:
<223> OTHER INFORMATION: A56R(F2)

<400> SEQUENCE: 21
caacaccaag gtggacaaga aagttaccac cgatgatgcg gatctttatg a         51

<210> SEQ ID NO 22
<211> LENGTH: 50
<212> TYPE: DNA
<213> ORGANISM: Artificial sequence
<220> FEATURE:
<223> OTHER INFORMATION: CH1 (R2):

<400> SEQUENCE: 22
acaaaagtat tggtaatcgt gtcataactt tcttgtccac cttggtgttg            50

<210> SEQ ID NO 23
<211> LENGTH: 51
<212> TYPE: DNA
<213> ORGANISM: Artificial sequence
<220> FEATURE:
<223> OTHER INFORMATION: A56R(R2):

<400> SEQUENCE: 23
tcataaagat ccgcatcatc ggtggtttta cccggagaca gggagaggct c          51

<210> SEQ ID NO 24
<211> LENGTH: 51
<212> TYPE: DNA
<213> ORGANISM: Artificial sequence
<220> FEATURE:
<223> OTHER INFORMATION: A56R(F3):

<400> SEQUENCE: 24
gagcctctcc ctgtctccgg gtaaaaccac cgatgatgcg gatctttatg a          51

<210> SEQ ID NO 25
<211> LENGTH: 50
<212> TYPE: DNA
<213> ORGANISM: Artificial sequence
<220> FEATURE:
<223> OTHER INFORMATION: A56R(R3):

<400> SEQUENCE: 25
tatcagtgtc atttgtagtt gatgttttac ccggagacag ggagaggctc            50

<210> SEQ ID NO 26
<211> LENGTH: 50
<212> TYPE: DNA
<213> ORGANISM: Artificial sequence
<220> FEATURE:
<223> OTHER INFORMATION: A56R (F4):

<400> SEQUENCE: 26
gagcctctcc ctgtctccgg gtaaaacatc aactacaaat gacactgata            50

<210> SEQ ID NO 27
<211> LENGTH: 1566
<212> TYPE: DNA
<213> ORGANISM: Artificial sequence
<220> FEATURE:
<223> OTHER INFORMATION: VH (H2124)-IgG-A56R TR Construct

<400> SEQUENCE: 27
caggtgcagc tgcagcagtg gggcgcagga ctgctgaagc ctagcgagac cctgtccctc    60
acctgcgctg tctatggcta ctccatcacc agcggctatt tctggaactg gatccgccag   120
ccccagggga aggggctgga gtggattggg tacatcagct acgacggcag cagcaactcc   180
aacccatctc tcaaaaatag ggtcacaatc agcagagaca cctccaagaa ccagttctcc   240

```
ctgaagctga gctctgtgac cgccgccgac accgctgtgt attactgtgc cagaggaact    300
accgggtttg cttactgggg ccaagggacc ctggtcaccg tctcctcagc ctccaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tcgtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaaac caccgatgat gcggatcttt atgatacgta caatgataat   1380
gatacagtac caccaactac tgtaggcggt agtacaacct ctattagcaa ttataaaacc   1440
aaggactttg tagaaatatt tggtattacc gcattaatta tattgtcggc cgtggcaatt   1500
ttctgtatta catattatat atataataaa cgttcacgta aatacaaaac agagaacaaa   1560
gtctag                                                              1566
```

<210> SEQ ID NO 28
<211> LENGTH: 521
<212> TYPE: PRT
<213> ORGANISM: Artificial sequence
<220> FEATURE:
<223> OTHER INFORMATION: VH (H2124)-IgG-A56R TR Construct

<400> SEQUENCE: 28

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Ile Thr Ser Gly
            20                  25                  30

Tyr Phe Trp Asn Trp Ile Arg Gln Pro Pro Gly Lys Gly Leu Glu Trp
        35                  40                  45

Ile Gly Tyr Ile Ser Tyr Asp Gly Ser Ser Asn Ser Asn Pro Ser Leu
    50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Thr Thr Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

```
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys Thr Thr
        435                 440                 445
Asp Asp Ala Asp Leu Tyr Asp Thr Tyr Asn Asp Asn Asp Thr Val Pro
450                 455                 460
Pro Thr Thr Val Gly Gly Ser Thr Thr Ser Ile Ser Asn Tyr Lys Thr
465                 470                 475                 480
Lys Asp Phe Val Glu Ile Phe Gly Ile Thr Ala Leu Ile Ile Leu Ser
                485                 490                 495
Ala Val Ala Ile Phe Cys Ile Thr Tyr Tyr Ile Tyr Asn Lys Arg Ser
            500                 505                 510
Arg Lys Tyr Lys Thr Glu Asn Lys Val
        515                 520

<210> SEQ ID NO 29
<211> LENGTH: 1962
```

<212> TYPE: DNA
<213> ORGANISM: Artificial sequence
<220> FEATURE:
<223> OTHER INFORMATION: VH (H2124)-IgG-A56R FL Construct

<400> SEQUENCE: 29

```
caggtgcagc tgcagcagtg gggcgcagga ctgctgaagc ctagcgagac cctgtccctc      60
acctgcgctg tctatggcta ctccatcacc agcggctatt tctggaactg gatccgccag     120
cccccaggga aggggctgga gtggattggg tacatcagct acgacggcag cagcaactcc     180
aacccatctc tcaaaaatag ggtcacaatc agcagagaca cctccaagaa ccagttctcc     240
ctgaagctga gctctgtgac cgccgccgac accgctgtgt attactgtgc cagaggaact     300
accgggtttg cttactgggg ccaagggacc ctggtcaccg tctcctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tcgtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtacaccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaaac atcaactaca aatgacactg ataaagtaga ttatgaagaa    1380
tactccacag agttgattgt aaatacagat agtgaatcga ctatagacat aatactatct    1440
ggatctacac attcaccgga aactagttct aagaaacctg attatataga taattctaat    1500
tgctcgtcgg tattcgaaat cgcgactccg gaaccaatta ctgataatgt agaagatcat    1560
acagacaccg tcacatacac tagtgatagc attaatacag taagtgcatc atctggagaa    1620
tccacaacag acgagactcc ggaaccaatt actgataaag aagatcatac agttacagac    1680
actgtctcat acactacagt aagtacatca tctggaattg tcactactaa atcaaccacc    1740
gatgatgcgg atctttatga tacgtacaat gataatgata cagtaccacc aactactgta    1800
ggcggtagta caacctctat tagcaattat aaaaccaagg actttgtaga aatatttggt    1860
attaccgcat taattatatt gtcggccgtg gcaatttttct gtattacata ttatatatat    1920
aataaacgtt cacgtaaata caaaacagag aacaaagtct ag                        1962
```

<210> SEQ ID NO 30
<211> LENGTH: 653
<212> TYPE: PRT
<213> ORGANISM: Artificial sequence
<220> FEATURE:

<223> OTHER INFORMATION: VH (H2124)-IgG-A56R FL Construct

<400> SEQUENCE: 30

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Ile Thr Ser Gly
            20                  25                  30

Tyr Phe Trp Asn Trp Ile Arg Gln Pro Pro Gly Lys Gly Leu Glu Trp
        35                  40                  45

Ile Gly Tyr Ile Ser Tyr Asp Gly Ser Ser Asn Ser Asn Pro Ser Leu
    50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Thr Thr Gly Phe Ala Tyr Trp Gly Gln Gly Thr Leu Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400
```

-continued

Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys Thr Ser
        435                 440                 445
Thr Thr Asn Asp Thr Asp Lys Val Asp Tyr Glu Glu Tyr Ser Thr Glu
    450                 455                 460
Leu Ile Val Asn Thr Asp Ser Glu Ser Thr Ile Asp Ile Leu Ser
465                 470                 475                 480
Gly Ser Thr His Ser Pro Glu Thr Ser Ser Lys Lys Pro Asp Tyr Ile
                485                 490                 495
Asp Asn Ser Asn Cys Ser Ser Val Phe Glu Ile Ala Thr Pro Glu Pro
            500                 505                 510
Ile Thr Asp Asn Val Glu Asp His Thr Asp Thr Val Thr Tyr Thr Ser
        515                 520                 525
Asp Ser Ile Asn Thr Val Ser Ala Ser Ser Gly Glu Ser Thr Thr Asp
    530                 535                 540
Glu Thr Pro Glu Pro Ile Thr Asp Lys Glu Asp His Thr Val Thr Asp
545                 550                 555                 560
Thr Val Ser Tyr Thr Thr Val Ser Thr Ser Ser Gly Ile Val Thr Thr
                565                 570                 575
Lys Ser Thr Thr Asp Asp Ala Asp Leu Tyr Asp Thr Tyr Asn Asp Asn
            580                 585                 590
Asp Thr Val Pro Pro Thr Thr Val Gly Gly Ser Thr Thr Ser Ile Ser
        595                 600                 605
Asn Tyr Lys Thr Lys Asp Phe Val Glu Ile Phe Gly Ile Thr Ala Leu
    610                 615                 620
Ile Ile Leu Ser Ala Val Ala Ile Phe Cys Ile Thr Tyr Tyr Ile Tyr
625                 630                 635                 640
Asn Lys Arg Ser Arg Lys Tyr Lys Thr Glu Asn Lys Val
                645                 650

<210> SEQ ID NO 31
<211> LENGTH: 24
<212> TYPE: DNA
<213> ORGANISM: Artificial sequence
<220> FEATURE:
<223> OTHER INFORMATION: heavy chain specific primer 428

<400> SEQUENCE: 31
gatatattaa agtcgaataa agtg                                          24

<210> SEQ ID NO 32
<211> LENGTH: 21
<212> TYPE: DNA
<213> ORGANISM: Artificial sequence
<220> FEATURE:
<223> OTHER INFORMATION: heavy chain specific primer 430

<400> SEQUENCE: 32
gacatcacat agtttagttg c                                             21

METHOD FOR SELECTING POLYNUCLEOTIDES ENCODING ANTIGEN-SPECIFIC IMMUNOGLOBULIN SUBUNIT

CROSS-REFERENCE TO RELATED APPLICATIONS

This application is a continuation of currently pending U.S. application Ser. No. 14/977,067, filed Dec. 21, 2015, which is a divisional of U.S. Non-provisional application Ser. No. 13/844,388, filed on Mar. 15, 2013, which claims priority benefit to U.S. Provisional Appl. No. 61/639,046, filed on Apr. 26, 2012 and U.S. Provisional Appl. No. 61/732,776, filed on Dec. 3, 2012; the content of each are hereby incorporated by reference in their entireties.

REFERENCE TO SEQUENCE LISTING SUBMITTED ELECTRONICALLY

The content of the electronically submitted sequence listing in ASCII text file (Name: "165547_Sequence_Listing_ascii_25.txt"; Size: 30,967 bytes; and Date of Creation: Apr. 27, 2017) filed herewith is incorporated herein by reference in its entirety.

BACKGROUND

Field of the Invention

The present invention relates to a high efficiency method of expressing immunoglobulin molecules on vaccinia virus particles, e.g., EEV virions, and/or on host cells, a method of producing immunoglobulin heavy and light chain libraries for expression in vaccinia virus particles, e.g., EEV virions, and/or eukaryotic cells, methods of isolating immunoglobulins which bind specific antigens, and immunoglobulins produced by any of these methods. The invention also relates to fusion proteins used for expressing immunoglobulin molecules on vaccinia virus particles, e.g., EEV virions, or on host cells.

Related Art

Immunoglobulin Production

Antibodies of defined specificity are being employed in an increasing number of diverse therapeutic applications. A number of methods have been used to obtain useful antibodies for human therapeutic use. These include chimeric and humanized antibodies, and fully human antibodies selected from libraries, e.g., phage display libraries, or from transgenic animals. Immunoglobulin libraries constructed in bacteriophage can derive from antibody producing cells of naïve or specifically immunized individuals and could, in principle, include new and diverse pairings of human immunoglobulin heavy and light chains. Although this strategy does not suffer from an intrinsic repertoire limitation, it requires that complementarity determining regions (CDRs) of the expressed immunoglobulin fragment be synthesized and fold properly in bacterial cells. Many antigen binding regions, however, are difficult to assemble correctly as a fusion protein in bacterial cells. In addition, the protein will not undergo normal eukaryotic post-translational modifications. As a result, this method imposes a different selective filter on the antibody specificities that can be obtained. Alternatively, fully human antibodies can be isolated from libraries in eukaryotic systems, e.g., yeast display, retroviral display, or expression in DNA viruses such as poxviruses. See, e.g., U.S. Pat. No. 7,858,559, which is incorporated herein by reference in its entirety.

The present invention enables efficient expression of a library of fully human antibodies on the surface of vaccinia virus, an enveloped mammalian virus. Similar to phage display, conditions are utilized wherein each vaccinia virion expresses a single immunoglobulin, e.g., an antibody or scFV, on its surface.

However, in the current invention, various panning and magnetic bead based methods have been developed to screen libraries of vaccinia-MAb virions to select recombinant virus encoding specific antibodies. Upon infection of mammalian cells, the antibody is not only incorporated into newly produced virus, it is also displayed on the surface of the host cell. This enables efficient selection strategies that combine the benefits of selection of vaccinia-MAb virions in a cell free panning system, followed by cell based screening for high specificity and antibody optimization.

This is different from other technologies in the field which express a single scFV but do not express a library. Moreover, other technologies are designed to re-direct vaccinia infection through the scFV for gene therapy and are not used for antibody discovery. Additionally, the current technology differs from the previous technology by using EEV instead of the IMV, and also by using different fusion proteins (e.g., A56R).

SUMMARY

In certain aspects, the disclosure is directed to fusion protein comprising (a) a first polypeptide segment comprising a heavy chain CH1 domain and (b) a second polypeptide segment comprising the transmembrane domain of a vaccinia extracellular enveloped virus (EEV)-specific membrane protein.

In some embodiments, the fusion protein further comprising a third polypeptide segment comprising an immunoglobulin heavy chain variable region or fragment thereof. In another embodiment, the vaccinia EEV-specific membrane protein is A56R.

In certain aspects, the disclosure is directed to a polynucleotide encoding a fusion protein comprising (a) a first polypeptide segment comprising the human heavy chain CH1 domain and (b) a second polypeptide segment comprising the transmembrane domain of a vaccinia extracellular enveloped virus (EEV)-specific membrane protein. In certain embodiments, the polynucleotide comprises nucleotides of SEQ ID NO: 10 which encodes amino acids 108 to 314 of A56R from Western Reserve Vaccinia virus strain. In certain embodiments, the polynucleotide encodes amino acids 215 to 421 of SEQ ID NO:11. In certain embodiments, the polynucleotide comprises the nucleotides of SEQ ID NO: 10 which encode amino acids 215 to 421 of SEQ ID NO:11.

In certain aspects, the disclosure is directed to a vector comprising a polynucleotide encoding a fusion protein comprising (a) a first polypeptide segment comprising the human heavy chain CH1 domain and (b) a second polypeptide segment comprising the transmembrane domain of a vaccinia extracellular enveloped virus (EEV)-specific membrane protein.

In certain aspects, the disclosure is directed to a recombinant vaccinia virus comprising a polynucleotide encoding a fusion protein comprising (a) a first polypeptide segment comprising the human heavy chain CH1 domain and (b) a second polypeptide segment comprising the transmembrane domain of a vaccinia extracellular enveloped virus (EEV)-specific membrane protein. In another aspect, the disclosure is directed to a host cell infected with the recombinant vaccinia virus.

In another aspect, the disclosure is directed to recombinant vaccinia library comprising a first library of polynucleotides constructed in a vaccinia virus vector encoding a plurality of immunoglobulin fusion polypeptides, wherein the vaccinia virus vector comprises (a) a first polynucleotide encoding a first polypeptide segment comprising a heavy chain CH1 domain (b) a second polynucleotide encoding a second polypeptide segment comprising the transmembrane domain of a vaccinia virus EEV-specific membrane protein situated downstream of the CH1 domain, and (c) a third polynucleotide encoding an immunoglobulin heavy chain variable region or fragment thereof situated upstream of the CH1 domain. In one embodiment, the first library further comprises a signal peptide for facilitating expression of the fusion polypeptides on the surface of EEV. In another embodiment, the EEV-specific membrane protein is A56R. In another embodiment, the vaccinia EEV-specific membrane protein is A56R. In another embodiment, the second polypeptide segment further comprises the extracellular domain of the EEV-specific membrane protein, or a portion thereof. In another embodiment, the second polypeptide segment further comprises the intracellular domain of the EEV-specific membrane protein, or a portion thereof. In certain embodiments, the fusion protein comprises amino acids of SEQ ID NO: 11 which correspond to the polypeptide sequence amino acids 108 to 314 of A56R from Western Reserve Vaccinia virus strain. In certain embodiments, the fusion protein comprises amino acids 215 to 421 of SEQ ID NO: 11. In certain embodiments, the fusion protein comprises amino acids 215 to 421 of SEQ ID NO: 11, which is amino acids 108 to 314 of A56R from Western Reserve Vaccinia virus strain.

In another aspect, the disclosure is directed to methods for selecting polynucleotides which encode an antigen-specific immunoglobulin heavy chain variable region or antigen-binding fragment thereof, comprising: (a) introducing the first library of any one of claims 13 to 18 encoding immunoglobulin fusion proteins into a population of host cells permissive for vaccinia virus infectivity; (b) introducing one or more polynucleotides encoding an immunoglobulin light chain into the population of host cells, wherein an immunoglobulin fusion protein is capable of combining with an immunoglobulin light chain to form an antigen-binding domain of an immunoglobulin molecule; (c) permitting release of extracellular enveloped virus (EEV) from the host cells; (d) collecting the released EEV from the supernatant; (e) contacting the released EEV with an antigen; and (f) recovering the polynucleotides of the first library which encode the immunoglobulin fusion polypeptides expressed on the membrane surface of EEV and specific for the antigen.

In one embodiment, to methods for selecting polynucleotides which encode an antigen-specific immunoglobulin heavy chain variable region or antigen-binding fragment thereof further comprises: (g) introducing the polynucleotides recovered in (f) into a second population of host cells permissive for vaccinia virus infectivity; (h) introducing one or more polynucleotides encoding an immunoglobulin light chain into the population of host cells; (i) permitting release of extracellular enveloped virus (EEV) from the host cells; (j) collecting the released EEV from the supernatant; (k) contacting the released EEV with an antigen; and (l) recovering the polynucleotides of the first library which encode the immunoglobulin fusion polypeptides expressed on the membrane surface of EEV and specific for the antigen.

In certain embodiments steps (g)-(l) are repeated one or more times, thereby enriching for polynucleotides of the first library which encode immunoglobulin heavy chain variable regions or antigen-specific fragments thereof, as part of an immunoglobulin fusion polypeptide that specifically binds the antigen.

In certain embodiments, the polynucleotides recovered from the first library are isolated.

In another aspect, the disclosure is directed to a method for selecting polynucleotides which encode an antigen-specific immunoglobulin molecule or antigen-specific fragment thereof, comprising: (a) introducing the first library into a population of host cells permissive for vaccinia virus infectivity; (b) introducing a second library into the population of host cells, where in the second library comprises a plurality of polynucleotides encoding an immunoglobulin light chain, Wherein the immunoglobulin fusion polypeptide is capable of combining with the immunoglobulin light chain to form an immunoglobulin molecule or antigen-specific fragment thereof; (c) permitting expression of the immunoglobulin fusion polypeptide from the host cells; (d) collecting the immunoglobulin fusion polypeptide from the host cells; (e) contacting the collected immunoglobulin fusion polypeptide with an antigen; and (f) recovering the polynucleotides of the first library which encode the immunoglobulin fusion polypeptides that are specific for the antigen.

In one embodiment, the method for selecting polynucleotides which encode an antigen-specific immunoglobulin molecule or antigen-specific fragment thereof further comprises: (g) introducing the polynucleotides recovered in (f) into a second population of host cells permissive for vaccinia virus infectivity; (h) introducing into the second population of host cells the second library of polynucleotides; (i) permitting expression of the immunoglobulin fusion polypeptide from the host cells; (j) collecting the immunoglobulin fusion polypeptide from the host cells; (k) contacting the collected immunoglobulin fusion polypeptide with an antigen; and (l) recovering the polynucleotides of the first library which encode the immunoglobulin fusion polypeptides that are specific for the antigen.

In certain embodiments steps (g)-(l) are repeated one or more times, thereby enriching for polynucleotides of the first library which encode immunoglobulin heavy chain variable regions or antigen-specific fragments thereof, as part of an immunoglobulin fusion polypeptide that specifically binds the antigen.

In one embodiment, the a method for selecting polynucleotides which encode an antigen-specific immunoglobulin molecule or antigen-specific fragment thereof further comprises isolating the third polynucleotides recovered from the first library.

BRIEF DESCRIPTION OF THE DRAWINGS/FIGURES

FIG. 1. Shows the pJEM1 plasmid elements and their respective sequences (SEQ ID NO:1).

FIG. 2. Shows an illustration of the general strategy for library selection using recombinant vaccinia virus.

Figure 3:
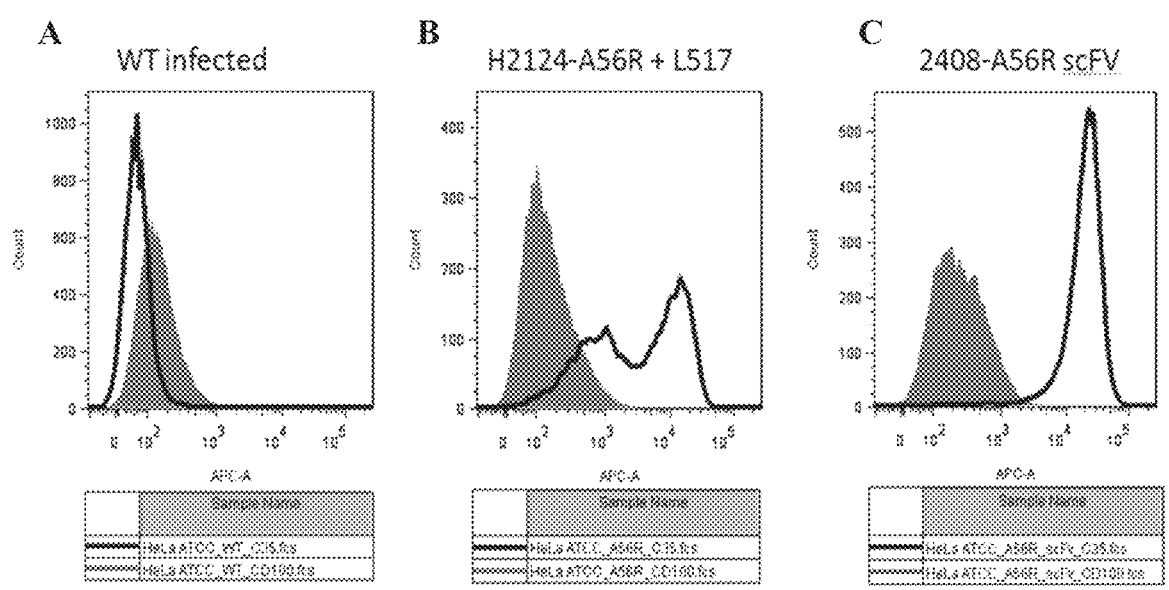

FIG. 3A-C. Show Fluorescence Activated Cell Sorting (FACS) analysis data for C35 staining and CD100 staining of HeLa cells infected with EEV recombinant vaccinia virus expressing H2124-A56R+L517 (B) or 2408-A56R-scFV (C) compared to wild-type (WT) infected cells (A).

FIG. 4A-B. Show ELISA binding results for EEV containing the C35 specific fusion protein (labeled "A56R EEV"), a control ("L517+G7000-A56R EEV"), and C35 specific antibody in standard membrane bound IgG1 format ("mbg EEV") with C35/Anti-Vac HRP (A) and C35/Anti-Fab (B).

FIG. 5A-D. Show plaque assay plate results for C35 binding after 2 hours (A) and overnight (B), and VEGF binding after 2 hours (C) and overnight (D).

Figure 6:
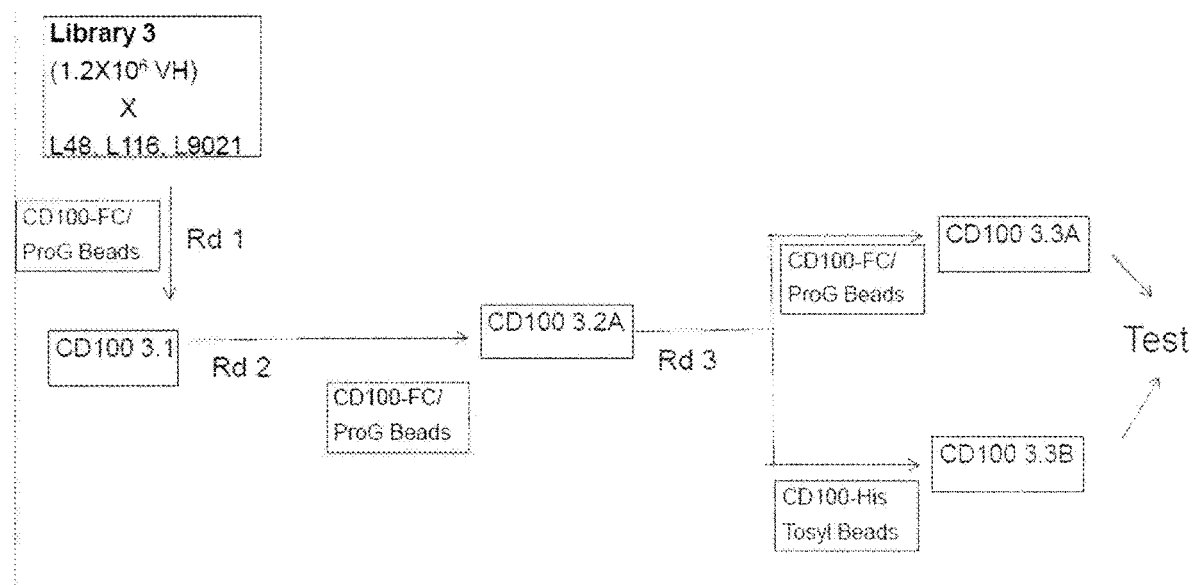

FIG. 6. Shows an illustration of the CD100 antibody selection strategy.

FIG. 7 shows an alignment of the VH sequence of CD100 clone C20 (SEQ ID NO:33) and an identical VH clone identified by the recombinant vaccinia library selection (SEQ ID NO:35). SEQ ID NO:34 comprises the consensus sequence.

Figure 8:
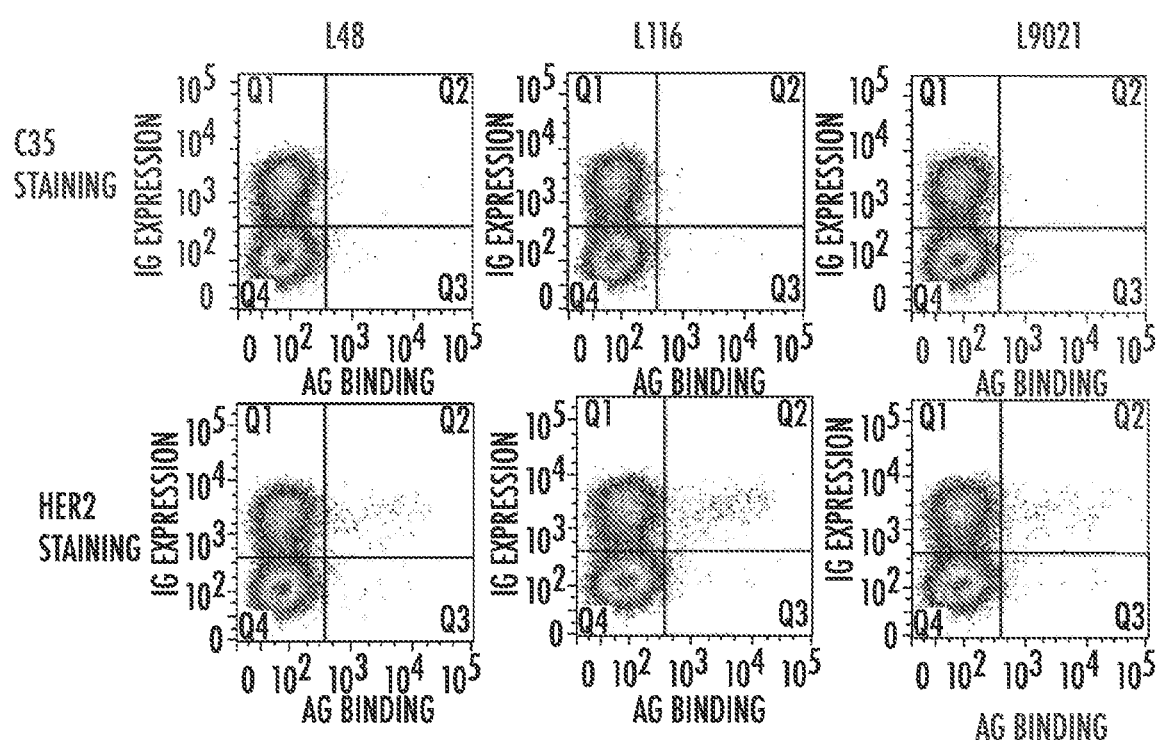

FIG. 8. Shows flow cytometry C35 and Her2 staining results for Her2.3.2 and Her2.3.3 selection with light chains L48, L116, and L9021.

Figure 9:
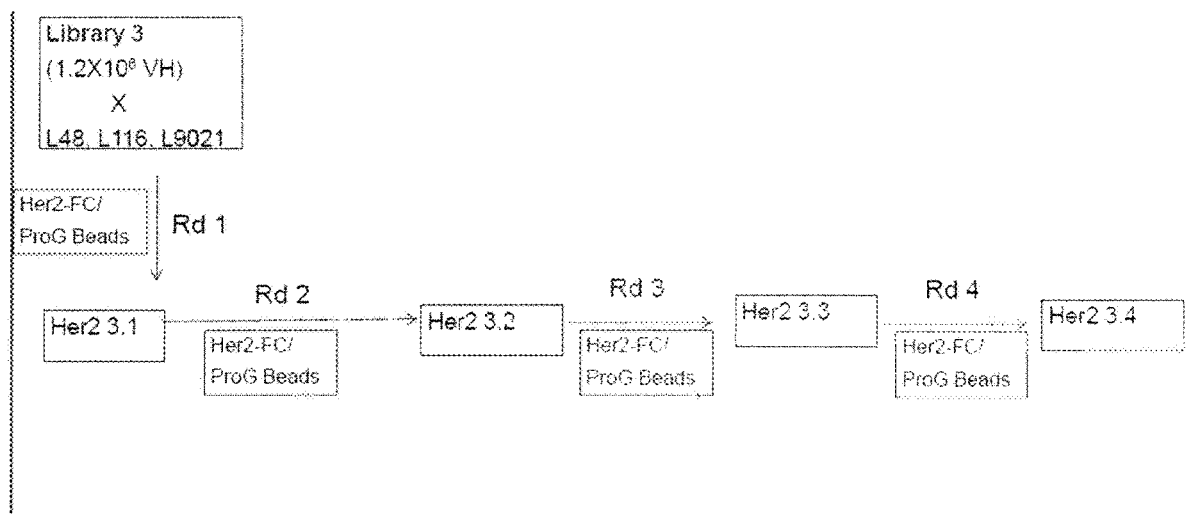

FIG. 9. Shows an illustration of the Her2 antibody selection strategy.

Figure 10:
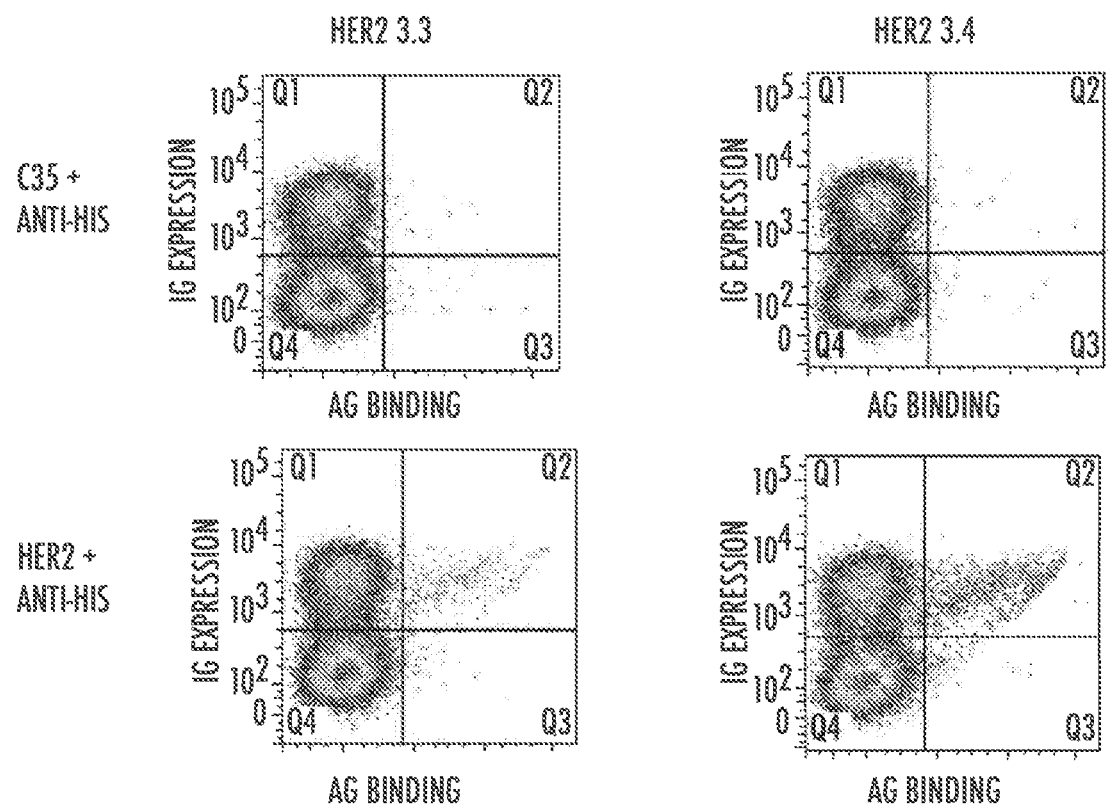

FIG. 10. Shows flow cytometry results for C35+anti-His and Her2+anti-His for Her2.3.2 and Her2.3.3 selection.

FIG. 11 shows the Her2 B10 clone sequence (SEQ ID NO:20) as well as an alignment of the VH sequence of Her2 clone B10 (SEQ ID NO:36) and an identical VH clone identified by the recombinant vaccinia library selection (SEQ ID NO:38). SEQ ID NO:37 comprises the consensus sequence.

Figure 12:
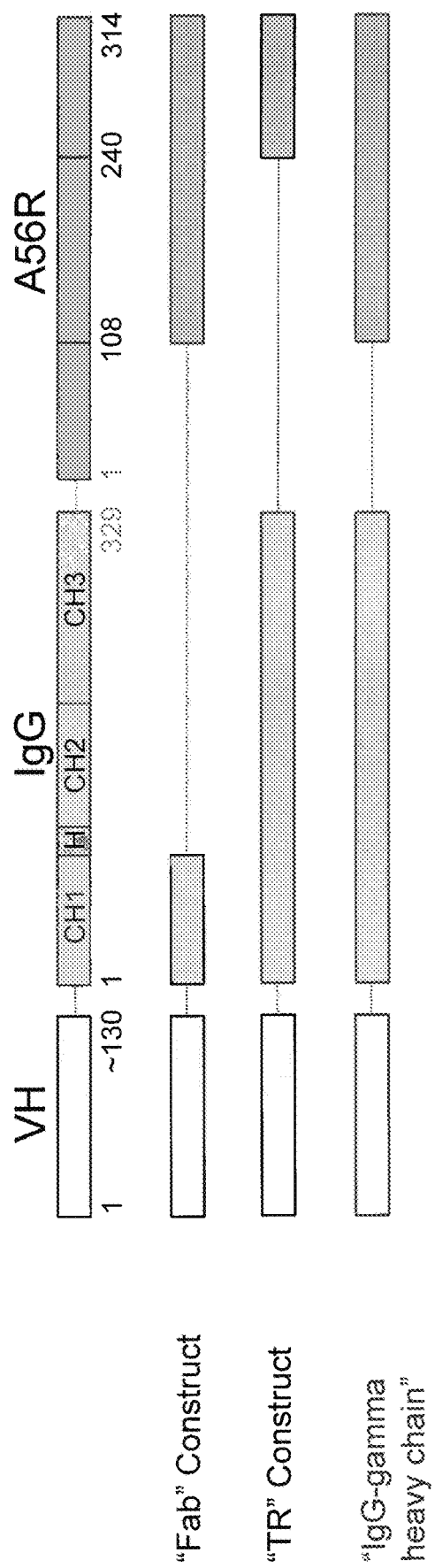

FIG. 12. Shows a diagram of "Fab", "TR", and "IgG-gamma heavy chain" constructs.

Figure 13:
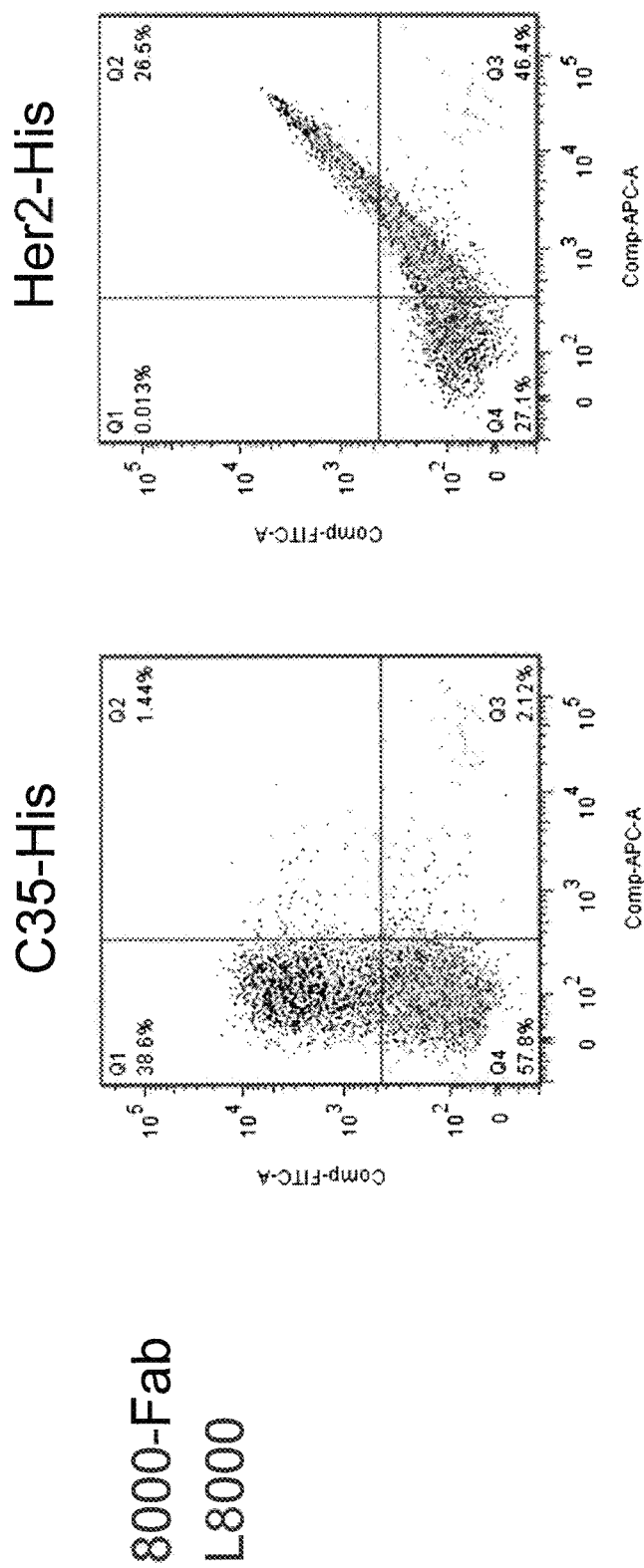

FIG. 13. Shows Fluorescence Activated Cell Sorting (FACS) analysis data for C35 staining and Her2 staining of HeLa cells infected with EEV recombinant vaccinia virus expressing 8000-Fab L8000.

FIG. 14. Shows Fluorescence Activated Cell Sorting (FACS) analysis data for C35 staining and Her2 staining of HeLa cells infected with EEV recombinant vaccinia virus expressing (A) 8000-IgG L8000 and (B) 8000-TR L8000.

FIG. 15. Shows Fluorescence Activated Cell Sorting (FACS) analysis data for C35 staining and Her2 staining of HeLa cells infected with EEV recombinant vaccinia virus expressing (A) H2124-IgG and (B) H2124-TR L517.

FIG. 16. Shows controls for CD100 Lib 10.3 FLOW analysis. Fluorescence Activated Cell Sorting (FACS) analysis data for Her2 staining and CD100 staining of HeLa cells infected with EEV recombinant vaccinia virus expressing (A) 2368 and (B) 8000.

FIG. 17. Shows results for Tosyl selected CD100 Lib 10.3 FLOW analysis. Fluorescence Activated Cell Sorting (FACS) analysis data for Her2 staining and CD100 staining of HeLa cells infected with EEV recombinant vaccinia virus expressing (A) L223, (B) L151, and (C) L9021.

FIG. 18. Shows results for Tosyl selected CD100 Lib 10.3 FLOW analysis. Fluorescence Activated Cell Sorting (FACS) analysis data for Her2 staining and CD100 staining of HeLa cells infected with EEV recombinant vaccinia virus expressing (A) L48, (B) L7110, and (C) L122.

FIG. 19. Shows results for Tosyl selected CD100 Lib 10.3 FLOW analysis. Fluorescence Activated Cell Sorting (FACS) analysis data for Her2 staining and CD100 staining of HeLa cells infected with EEV recombinant vaccinia virus expressing (A) L116, (B) L214, and (C) L3-1.

Figure 20:
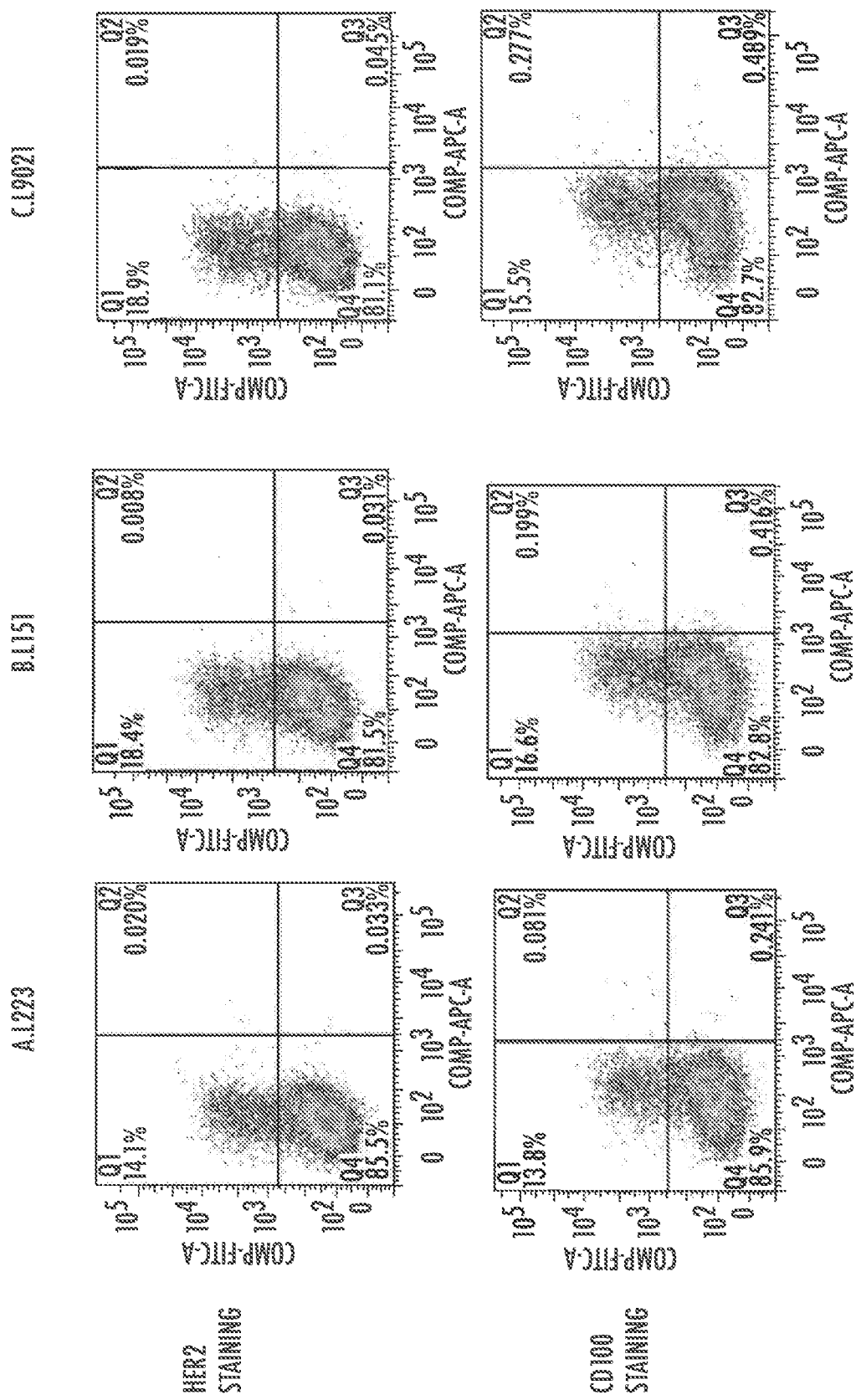

FIG. 20. Shows results for ProG selected CD100 Lib 10.3 FLOW analysis. Fluorescence Activated Cell Sorting (FACS) analysis data for Her2 staining and CD100 staining of HeLa cells infected with EEV recombinant vaccinia virus expressing (A) L223, (B) L151, and (C) L9021.

FIG. 21. Shows results for ProG selected CD100 Lib 10.3 FLOW analysis. Fluorescence Activated Cell Sorting (FACS) analysis data for Her2 staining and CD100 staining of HeLa cells infected with EEV recombinant vaccinia virus expressing (A) L48, (B) L7110, and (C) L122.

FIG. 22. Shows results for Protein G selected CD100 Lib 10.3 FLOW analysis. Fluorescence Activated Cell Sorting (FACS) analysis data for Her2 staining and CD100 staining of HeLa cells infected with EEV recombinant vaccinia virus expressing (A) L116, (B) L214, and (C) L3-1.

Figure 23:
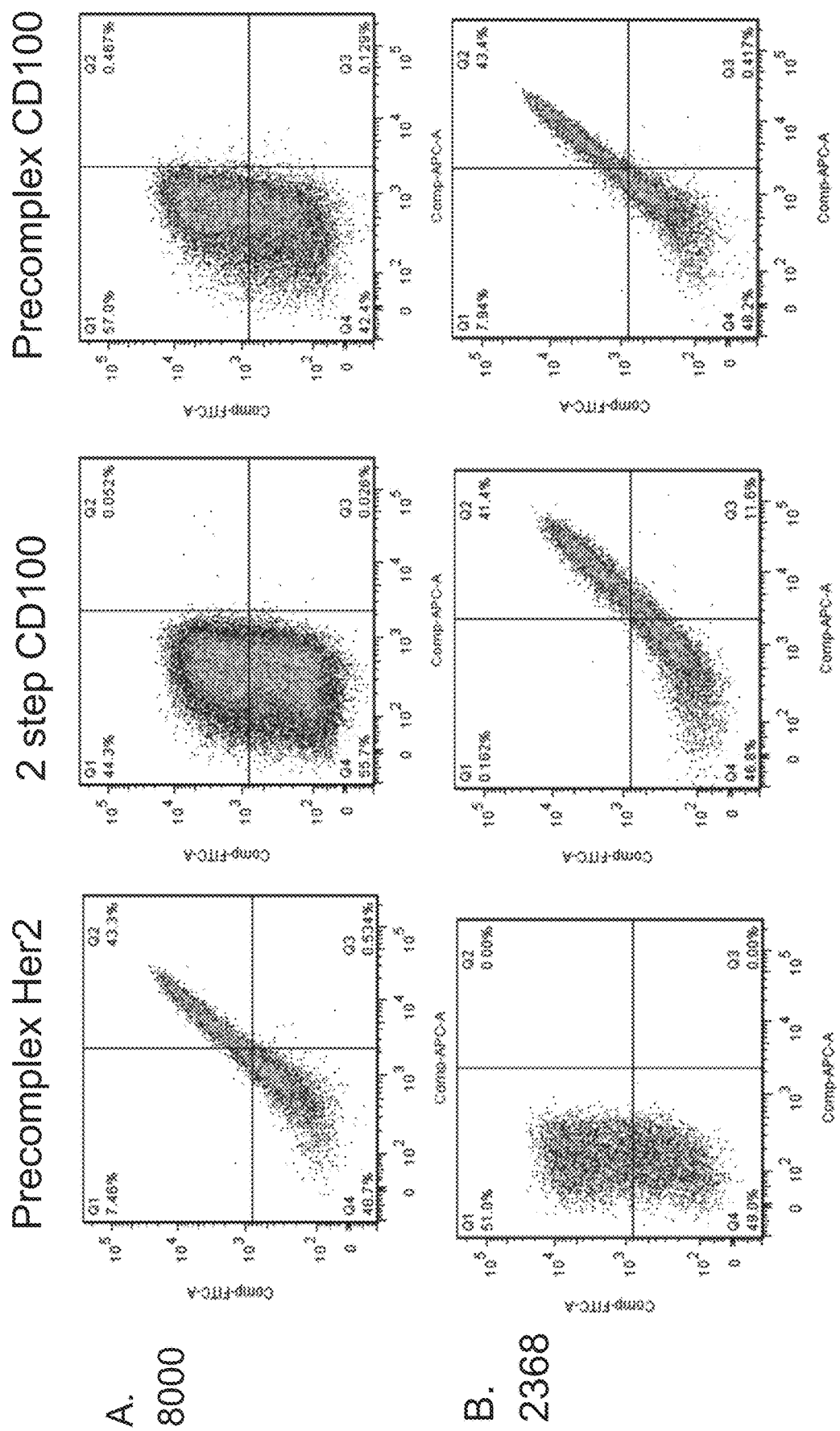

FIG. 23. Shows controls for CD100 Lib 10.3/L3-1 FLOW analysis. Fluorescence Activated Cell Sorting (FACS) analysis data for Precomplex Her2 staining, 2 steps CD100 staining, and Precomplex CD100 staining of HeLa cells infected with EEV recombinant vaccinia virus expressing (A) 8000 and (B) 2368.

Figure 24:
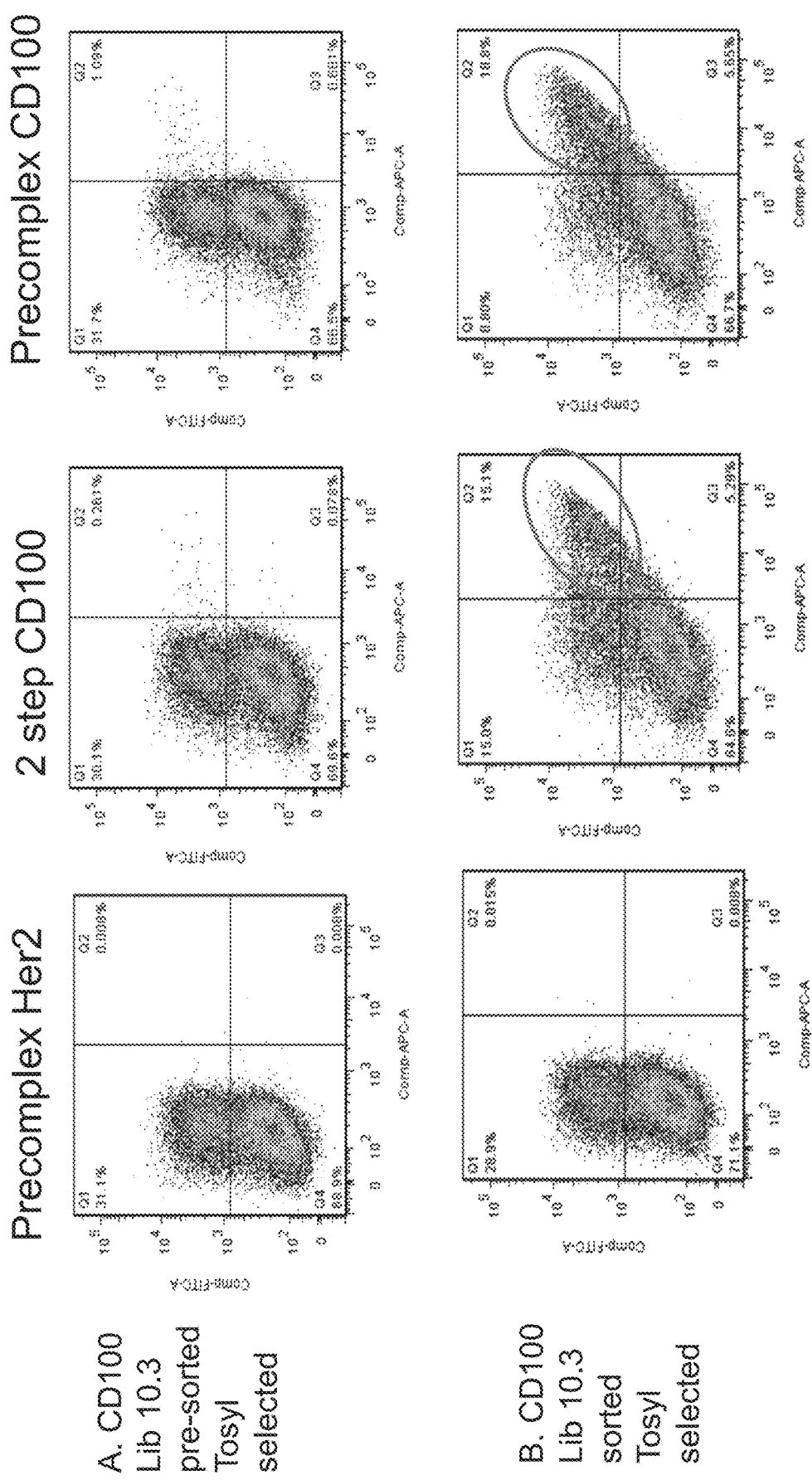

FIG. 24. Shows results for CD100 Lib 10.3Tosyl/L3-1 FLOW analysis. Fluorescence Activated Cell Sorting (FACS) analysis data for Precomplex Her2 staining, 2 steps CD100 staining, and Precomplex CD100 staining of HeLa cells infected with EEV recombinant vaccinia virus expressing (A) CD100 Lib 10.3 pre-sorted Tosyl selected and (B) CD100 Lib 10.3 sorted Tosyl selected.

Figure 25:
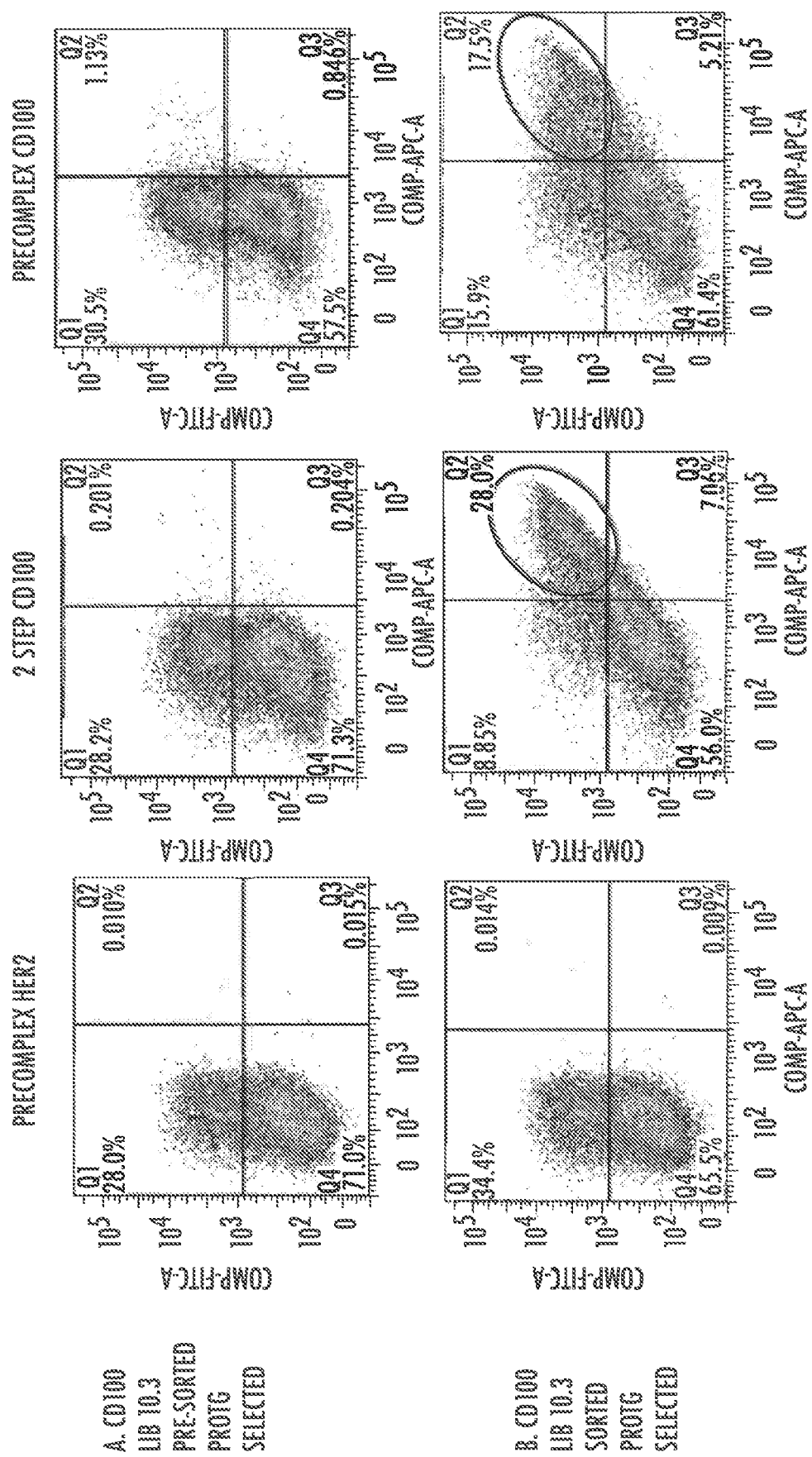

FIG. 25. Shows results for CD100 Lib 10.3ProtG/L3-1 FLOW analysis. Fluorescence Activated Cell Sorting (FACS) analysis data for Precomplex Her2 staining, 2 steps CD100 staining, and Precomplex CD100 staining of HeLa cells infected with EEV recombinant vaccinia virus expressing (A) CD100 Lib 10.3 pre-sorted Protein G selected and (B) CD100 Lib 10.3 sorted Protein G selected.

FIG. 26. Shows flow cytometry results showing specificity to CD100 on Jurkat cells (CD100+) and BxPC3 cells for mAbs 2050, 2063, and 2110.

Figure 27:
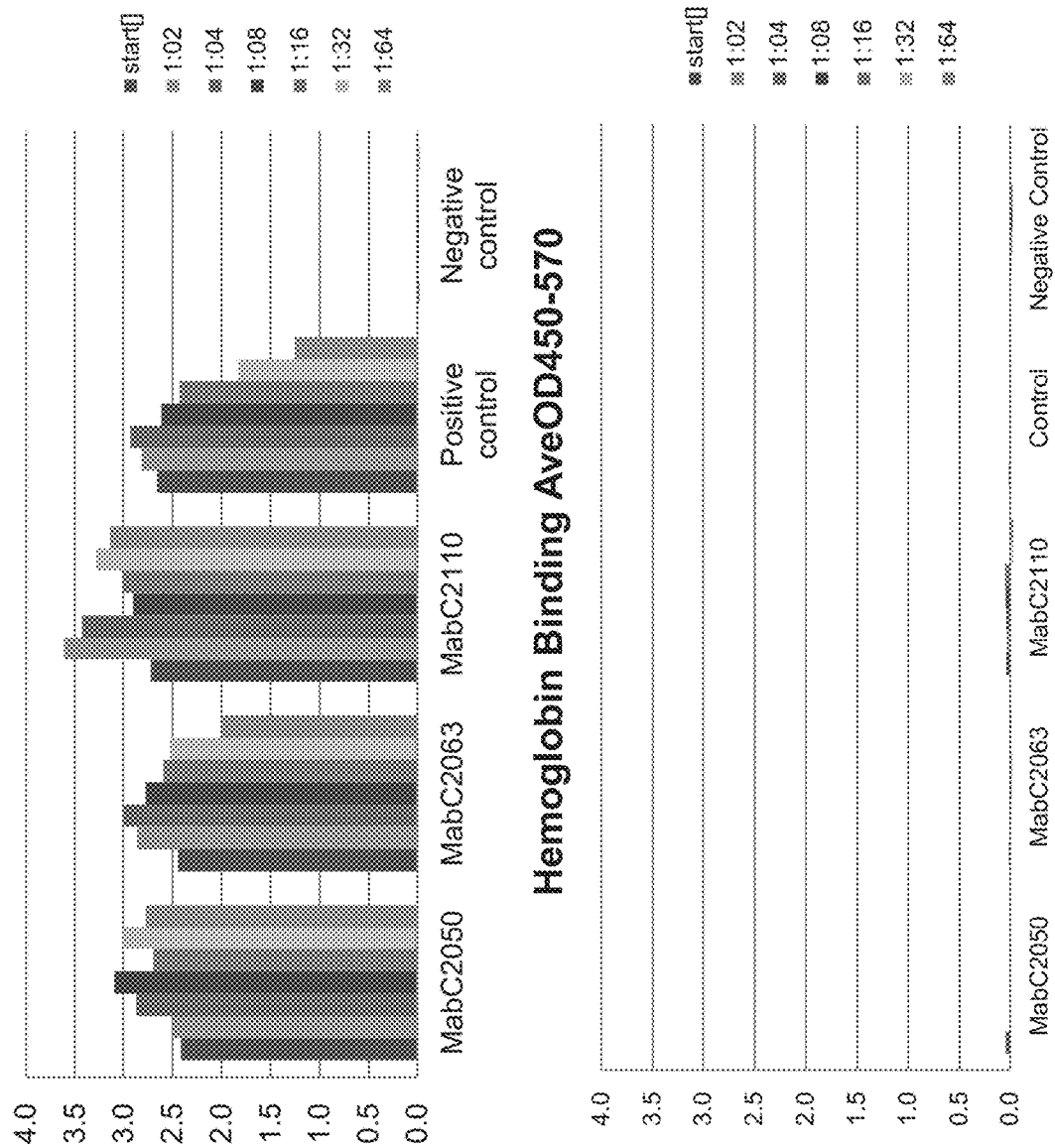

FIG. 27. Shows ELISA results on (A) huCD100-His coated and (B) Hemoglobin coated plates with three CD100 specific antibodies (Mab2050, MabC2063, and MabC2110) compared to positive and negative controls.

Figure 28:
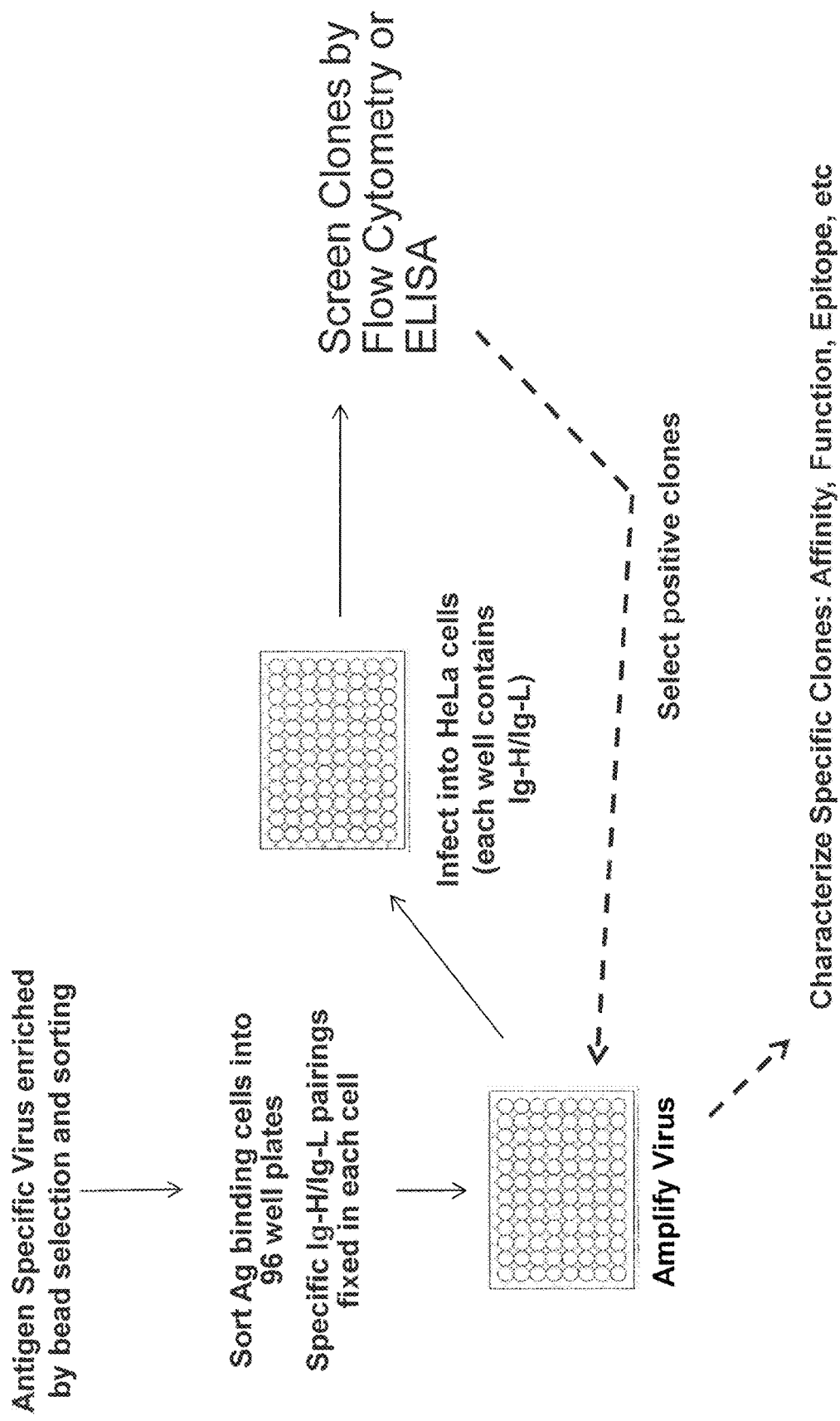

FIG. 28. Shows a schematic for identification of specific Ig-H/Ig-L following vaccinia display methods.

Figure 29:
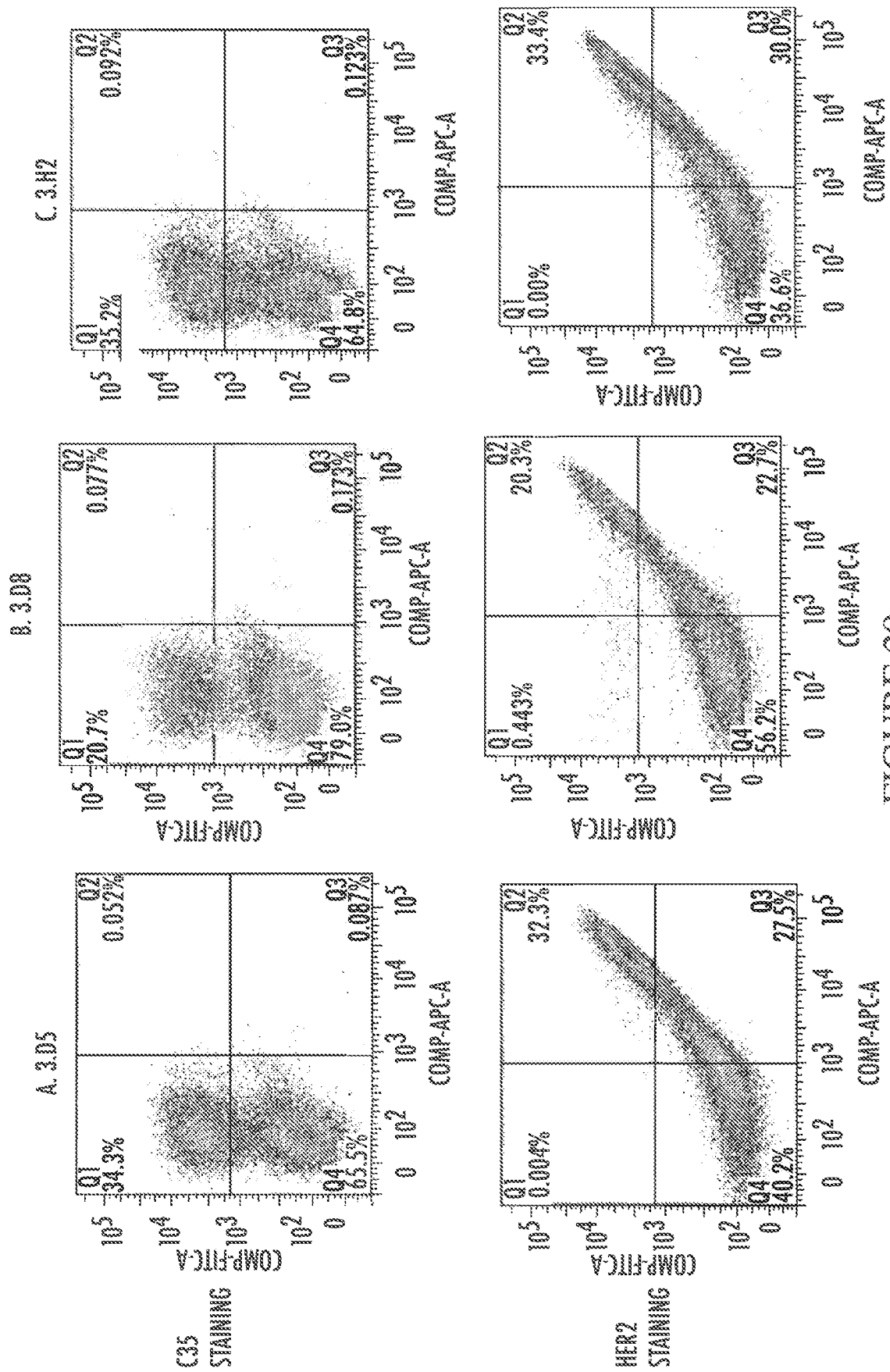

FIG. 29. Fluorescence Activated Cell Sorting (FACS) analysis data for C35 and Her2 staining of HeLa cells infected with EEV recombinant vaccinia virus expressing Her2 specific clones (A) D5, (B) D8, and (C) H2.

Figure 30:
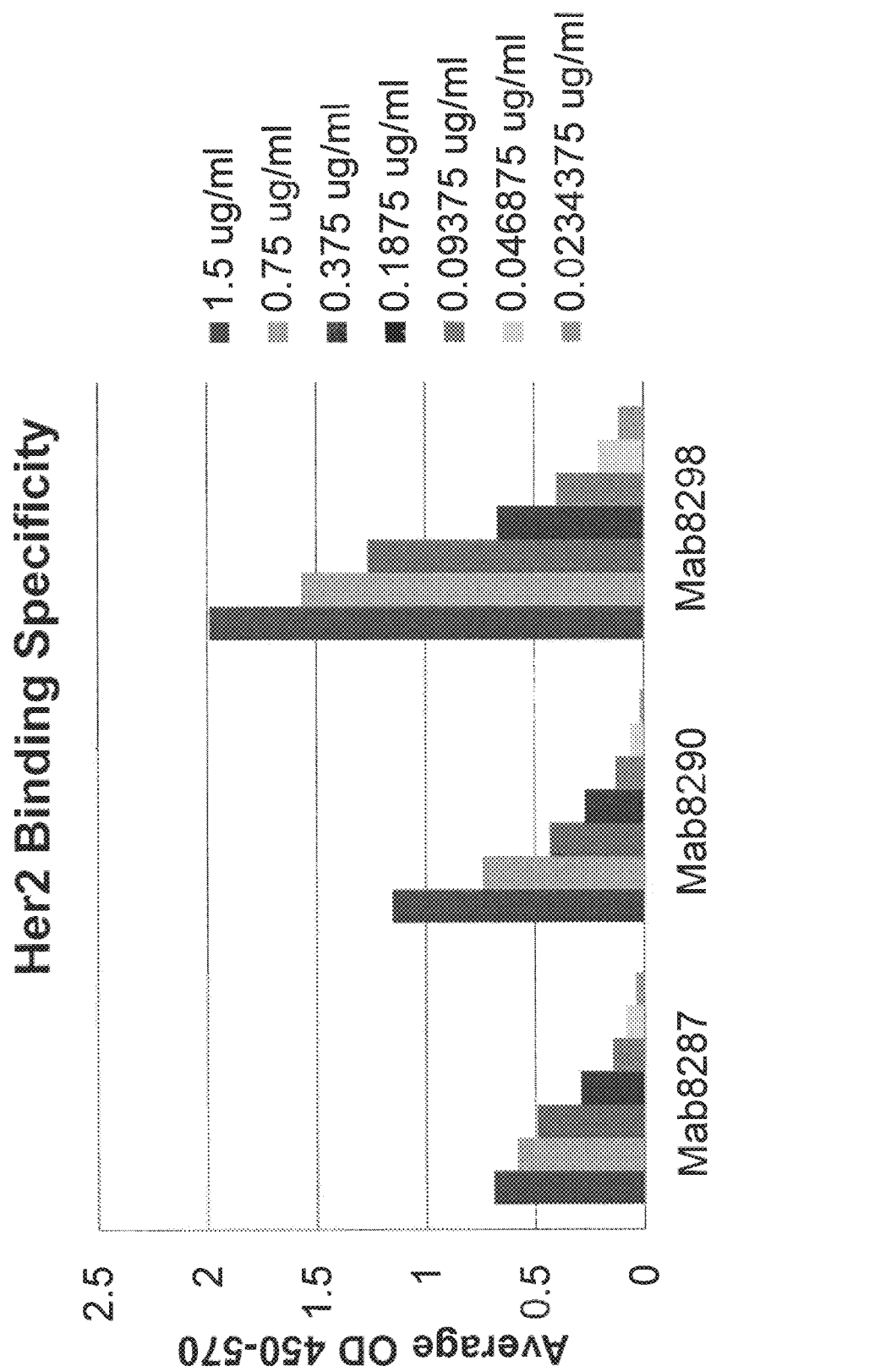

FIG. 30. Shows ELISA results for three Her2 specific antibodies (Mab8287, Mab8290, and Mab9298).

Figure 31:
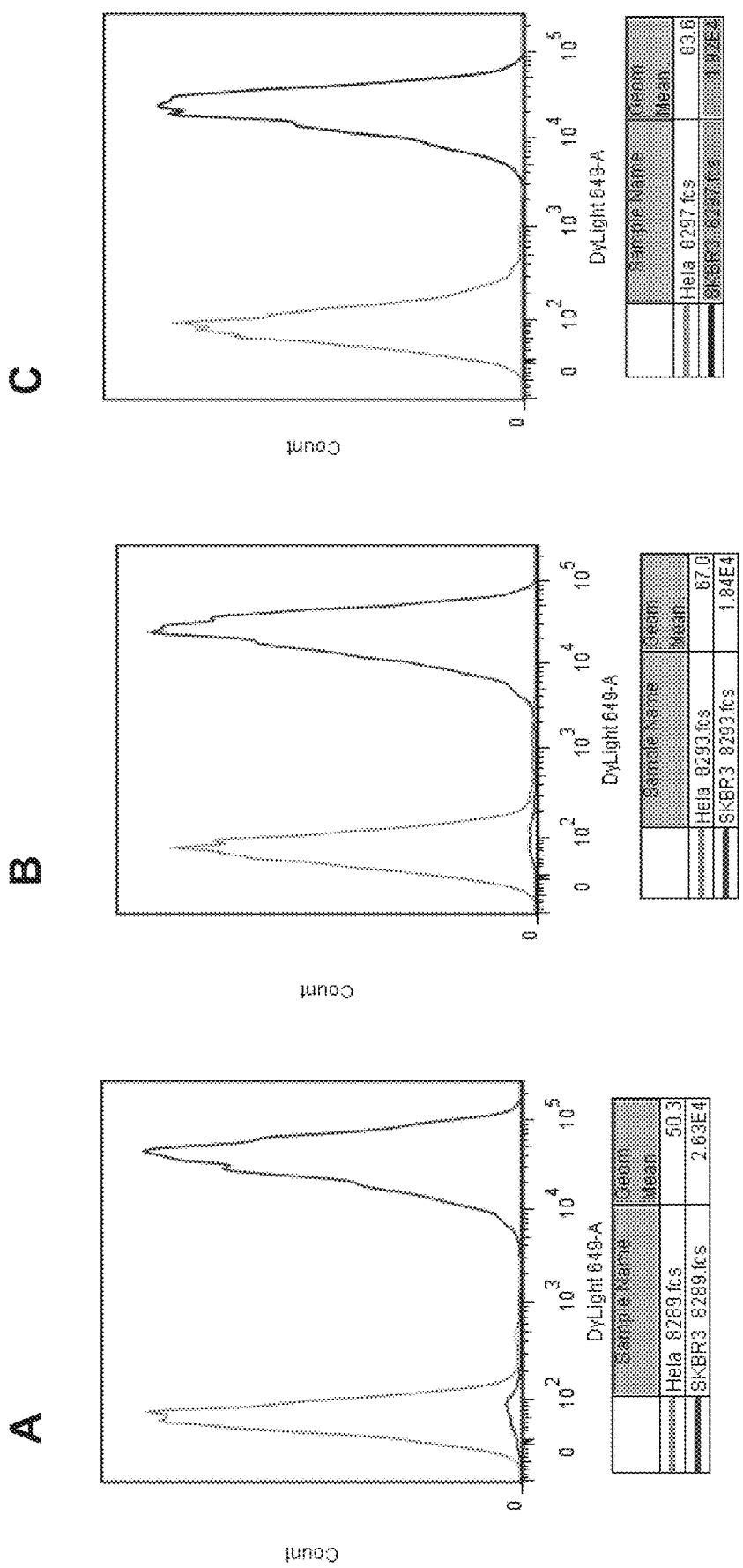

FIG. 31. Shows flow cytometry results showing specificity to Her2 on SKBR3 cells (Her2+++) for Mab8289, Mab8293, and Mab8297.

DETAILED DESCRIPTION

The present invention is broadly directed to methods of identifying and/or producing functional, antigen-specific immunoglobulin molecules, or antigen-specific fragments (i.e., antigen-binding fragments) thereof, in a eukaryotic system displayed on the surface of extracellular enveloped vaccinia virus (EEV), as a fusion with a polypeptide segment comprising the transmembrane domain of an EEV-specific membrane protein. In addition, the invention is directed to methods of identifying polynucleotides which encode an antigen-specific immunoglobulin molecule, or an antigen-specific fragment thereof, from complex expression libraries of polynucleotides encoding such immunoglobulin molecules or fragments, where the libraries are constructed and screened in a eukaryotic system displayed on the surface of extracellular enveloped vaccinia virus (EEV), as a fusion with a polypeptide segment comprising the transmembrane domain of an EEV-specific membrane protein. Further embodiments include a fusion protein comprising (a) a first polypeptide segment comprising the human heavy chain CH1 domain (b) a second polypeptide segment comprising the extracellular and transmembrane domains of a vaccinia extracellular enveloped virus (EEV)-specific membrane protein. In further embodiments a fusion protein as disclosed herein can include a binding molecule, e.g., an antigen-specific portion of an immunoglobulin or portion thereof, e.g., a heavy chain variable region, which, when paired with a suitable immunoglobulin light chain, binds to an antigen of interest.

One aspect of the present invention is the construction of complex immunoglobulin libraries in a eukaryotic system displayed on the surface of extracellular enveloped vaccinia virus (EEV), as a fusion with a polypeptide segment comprising the transmembrane domain of an EEV-specific membrane protein.

It is to be noted that the term "a" or "an" entity, refers to one or more of that entity; for example, "an immunoglobulin molecule," is understood to represent one or more immunoglobulin molecules. As such, the terms "a" (or "an"), "one or more," and "at least one" can be used interchangeably herein.

The term "eukaryote" or "eukaryotic organism" is intended to encompass all organisms in the animal, plant, and protist kingdoms, including protozoa, fungi, yeasts, green algae, single celled plants, multi celled plants, and all animals, both vertebrates and invertebrates. The term does not encompass bacteria or viruses. A "eukaryotic cell" is intended to encompass a singular "eukaryotic cell" as well as plural "eukaryotic cells," and comprises cells derived from a eukaryote.

The term "vertebrate" is intended to encompass a singular "vertebrate" as well as plural "vertebrates," and comprises mammals and birds, as well as fish, reptiles, and amphibians.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears. In certain embodiments, the mammal is a human subject.

The terms "tissue culture" or "cell culture" or "culture" or "culturing" refer to the maintenance or growth of plant or animal tissue or cells in vitro under conditions that allow preservation of cell architecture, preservation of cell function, further differentiation, or all three. "Primary tissue cells" are those taken directly from tissue, i.e., a population of cells of the same kind performing the same function in an organism. Treating such tissue cells with the proteolytic enzyme trypsin, for example, dissociates them into individual primary tissue cells that grow or maintain cell architecture when seeded onto culture plates.

The term "polynucleotide" refers to any one or more nucleic acid segments, or nucleic acid molecules, e.g., DNA or RNA fragments, present in a nucleic acid or construct. A "polynucleotide encoding an immunoglobulin subunit polypeptide" refers to a polynucleotide which comprises the coding region for such a polypeptide. In addition, a polynucleotide can encode a regulatory element such as a promoter or a transcription terminator, or can encode a specific element of a polypeptide or protein, such as a secretory signal peptide or a functional domain.

As used herein, the term "identify" refers to methods in which desired molecules, e.g., polynucleotides encoding immunoglobulin molecules with a desired specificity or function, are differentiated from a plurality or library of such molecules. Identification methods include "selection" and "screening." As used herein, "selection" methods are those in which the desired molecules can be directly separated from the library. For example, in one selection method described herein, host cells comprising the desired polynucleotides are directly separated from the host cells comprising the remainder of the library by undergoing a lytic event and thereby being released from the substrate to which the remainder of the host cells are attached. As used herein, "screening" methods are those in which pools comprising the desired molecules are subjected to an assay in which the desired molecule can be detected. Aliquots of the pools in which the molecule is detected are then divided into successively smaller pools which are likewise assayed, until a pool which is highly enriched from the desired molecule is achieved.

Immunoglobulins.

As used herein, an "immunoglobulin molecule" is defined as a complete, bi-molecular immunoglobulin, i.e., generally comprising four "subunit polypeptides," i.e., two identical heavy chains and two identical light chains. In some instances, e.g., immunoglobulin molecules derived from camelid species or engineered based on camelid immunoglobulins, a complete immunoglobulin molecule can consist of heavy chains only, with no light chains. See, e.g., Hamers-Casterman et al., *Nature* 363:446-448 (1993). Thus, by an "immunoglobulin subunit polypeptide" is meant a single heavy chain polypeptide or a single light chain polypeptide. Immunoglobulin molecules are also referred to as "antibodies," and the terms are used interchangeably herein. An "isolated immunoglobulin" refers to an immunoglobulin molecule, or two or more immunoglobulin molecules, which are substantially removed from the milieu of proteins and other substances, and which bind a specific antigen.

The heavy chain, which determines the "class" of the immunoglobulin molecule, is the larger of the two subunit polypeptides, and comprises a variable region and a constant region. By "heavy chain" is meant either a full-length secreted heavy chain form, i.e., one that is released from the cell, or a membrane bound heavy chain form, i.e., comprising a membrane spanning domain, e.g., fusions with a polypeptide segment comprising the transmembrane domain of an EEV-specific membrane protein. Immunoglobulin "classes" refer to the broad groups of immunoglobulins which serve different functions in the host. For example, human immunoglobulins are divided into five classes, i.e., IgG, comprising a γ heavy chain, IgM, comprising µ heavy chain, IgA, comprising an α heavy chain, IgE, comprising an ε heavy chain, and IgD, comprising a δ heavy chain.

By "light chain" is meant the smaller immunoglobulin subunit which associates with the amino terminal region of a heavy chain. As with a heavy chain, a light chain comprises a variable region and a constant region. There are two different kinds of light chains, κ and λ, and a pair of these can associate with a pair of any of the various heavy chains to form an immunoglobulin molecule.

Immunoglobulin subunit polypeptides typically comprise a constant region and a variable region. In most species, the heavy chain variable region, or $V_H$ domain, and the light chain variable region, or $V_L$ domain, combine to form a "complementarity determining region" or CDR, the portion of an immunoglobulin molecule which specifically recognizes an antigenic epitope. A large repertoire of variable regions associated with heavy and light chain constant regions are produced upon differentiation of antibody-producing cells in an animal through rearrangements of a series of germ line DNA segments which results in the formation of a gene which encodes a given variable region. Further variations of heavy and light chain variable regions take place through somatic mutations in differentiated cells. The structure and in vivo formation of immunoglobulin molecules is well understood by those of ordinary skill in the art of immunology. Concise reviews of the generation of immunoglobulin diversity can be found, e.g., in Harlow and Lane, *Antibodies, A Laboratory Manual* Cold Spring Harbor Laboratory, Cold Spring Harbor, N.Y. (1988) (hereinafter, "Harlow"); and Roitt, et al., *Immunology* Gower Medical Publishing, Ltd., London (1985) (hereinafter, "Roitt"). Harlow and Roitt are incorporated herein by reference in their entireties.

As used herein, an "antigen-specific fragment" of an immunoglobulin molecule is any fragment or variant of an immunoglobulin molecule which remains capable of binding an antigen. Antigen-specific fragments include, but are not limited to, Fab, Fab' and F(ab')$_2$, Fd, single-chain Fvs (scFv), single-chain immunoglobulins (e.g., wherein a heavy chain, or portion thereof, and light chain, or portion thereof, are fused), disulfide-linked Fvs (sdFv), diabodies, triabodies, tetrabodies, scFv minibodies, Fab minibodies, and dimeric scFv and any other fragments comprising a $V_L$ and a $V_H$ domain in a conformation such that a specific CDR is formed.

Antigen-specific immunoglobulin fragments can comprise the variable region(s) alone or in combination with the entire or partial constant region, e.g., a CH1, CH2, CH3 domain on the heavy chain, and a light chain constant domain, e.g., a $C_\kappa$ or $C_\lambda$ domain, or portion thereof on the light chain. In certain aspects a fusion protein as disclosed herein comprises a heavy chain variable domain fused to a CH1 constant domain fused to a polypeptide segment comprising the transmembrane domain of an EEV-specific membrane protein, e.g., A56R.

In certain embodiments, the present invention is drawn to methods to identify, i.e., select or alternatively screen for, polynucleotides which singly or collectively encode antigen-specific immunoglobulin molecules or antigen-specific fragments thereof. In certain embodiments a method of selecting an immunoglobulin molecule with an antigen specificity of interest is provided, where the immunoglobulin or antibody is displayed on the surface of an EEV, the EEV is isolated, and the polynucleotide encoding a portion of the immunoglobulin, e.g., the VH region, is isolated.

In certain aspects, a method for selecting polynucleotides which encode an antigen-specific immunoglobulin molecule is provided, where the method comprises: (1) introducing a first library of polynucleotides into a population of host cells permissive for vaccinia virus infectivity. The library can be constructed in a vaccinia virus vector, e.g., an EEV vector, encoding a plurality of immunoglobulin fusion polypeptides, where the vaccinia virus vector comprises (a) a first polynucleotide encoding a first polypeptide segment comprising the human heavy chain CH1 domain, e.g., a CH1-gamma domain, (b) a second polynucleotide encoding a second polypeptide segment comprising the extracellular and transmembrane domains of a vaccinia membrane protein, e.g., a polypeptide segment comprising the transmembrane domain of an EEV-specific membrane protein, e.g., A56R, and (c) a third polynucleotide encoding an immunoglobulin heavy chain variable region or fragment thereof. The method further comprises (2) introducing into the population of host cells a polynucleotide encoding a light chain, e.g., a known light chain or a second library comprising a plurality of polynucleotides each encoding an immunoglobulin light chain. Once introduced into the population of host cells, the immunoglobulin fusion polypeptide can combine with the immunoglobulin light chain to form an antigen-binding portion of an immunoglobulin molecule, where the molecule can be expressed or "displayed" on the surface of a selectable particle, e.g., an EEV virion produced and released by the host cells into the surrounding medium. The method further provides selecting EEV released from the host cells that bind to an antigen of interest, e.g., by antigen-specific attachment to a plate or to beads, e.g., protein G beads, streptavidin beads, or tosylated beads. EEV expressing the antigen-binding domain of interest can then be recovered, and used to reinfect new host cells, thereby enriching for EEV containing polynucleotides which encode the heavy chain of immunoglobulin binding to the antigen of interest. The polynucleotides can then be recovered. The method can be repeated thereby enriching for polynucleotides encoding heavy chain fusion proteins of interest.

Isolated polynucleotides encoding the immunoglobulin heavy chain polypeptide fusion proteins binding to an antigen of interest can then be transferred into and expressed in host cells (either as an EEV fusion protein or not) in which a library of polynucleotides encoding immunoglobulin light chain variable regions fused to a polypeptide segment comprising the transmembrane domain of an EEV-specific membrane protein, thereby allowing identification of a polynucleotide encoding a light chain variable region which, when combined with the heavy chain variable region identified in the first step, forms a functional immunoglobulin molecule, or fragment thereof, which recognizes a specific antigen.

As used herein, a "library" is a representative genus of polynucleotides, i.e., a group of polynucleotides related through, for example, their origin from a single animal species, tissue type, organ, or cell type, where the library collectively comprises at least two different species within a given genus of polynucleotides. A library of polynucleotides can comprise at least 10, 100, $10^3$, $10^4$, $10^5$, $10^6$, $10^7$, $10^8$, or $10^9$ different species within a given genus of polynucleotides. The genus can be related molecules, e.g., immunoglobulin variable regions, e.g., human immunoglobulin VH domains or VL domains. The VH and VL domains can represent an entire repertoire of variable domains, or can already be antigen-specific, e.g., specific for the same antigen. More specifically, a library can encode a plurality of a immunoglobulin subunit polypeptides, i.e., either heavy chain subunit polypeptides or light chain subunit polypeptides. In this context, a "library" can comprise polynucleotides of a common genus, the genus being polynucleotides encoding an immunoglobulin subunit polypeptide of a certain type and class e.g., a library might encode a human μ, γ1, γ-1, γ-2, γ-3, γ-4, α-1, α-2, ε, or δ heavy chain, or a human κ or λ light chain. Although each member of any one library can encode the same heavy or light chain constant region, the library can collectively comprise at least two, or at least 10, 100, $10^3$, $10^4$, $10^5$, $10^6$, $10^7$, $10^8$, or $10^9$ different variable regions i.e., a "plurality" of variable regions associated with the common constant region.

In other embodiments, the library can encode a plurality of immunoglobulin single-chain fragments which comprise a variable region, such as a light chain variable region or a heavy chain variable region, or can comprise both a light chain variable region and a heavy chain variable region.

In one aspect, provided herein is a method to produce libraries of polynucleotides encoding immunoglobulin subunit polypeptides. Further provided are libraries of immunoglobulin subunit polypeptides constructed as fusion proteins in eukaryotic expression vectors, e.g., EEV, where the immunoglobulin subunit polypeptide is fused to a polypeptide segment comprising the transmembrane domain of an EEV-specific membrane protein, e.g., A56R.

By "recipient cell" or "host cell" or "cell" is meant a cell or population of cells into which polynucleotide libraries as described herein are introduced. Suitable host cells for libraries described herein are eukaryotic cells permissive for vaccinia virus infection. Suitable cell lines can be vertebrate, mammalian, rodent, mouse, primate, or human cell or cell lines.

By "a population of host cells" is meant a group of cultured cells into which a "library" as provided herein can be introduced and expressed. Host cells for EEV libraries as described herein can be permissive for vaccinia virus infection. Host cells of the present invention can be adherent, i.e., host cells which grow attached to a solid substrate, or, alternatively, the host cells can be in suspension.

As noted above, certain methods to identify immunoglobulin molecules comprise the introduction of a "first" library of polynucleotides (encoding, e.g., a VH-CH1-A56R fusion protein) into a population of host cells, as well as a "second" library of polynucleotides (e.g., encoding a VL region) into the same population of host cells. The first and second libraries are complementary, i.e., if the "first" library encodes immunoglobulin heavy chain variable domains, the "second" library will encode immunoglobulin light chain variable domains, thereby allowing assembly of immunoglobulin molecules, or antigen-specific fragments thereof, in the population of host cells, such that the immunoglobulins are expressed, or displayed, on the surface of EEV.

Polynucleotides contained in libraries described herein can encode immunoglobulin subunit polypeptides through "operable association with a transcriptional control region." One or more nucleic acid molecules in a given polynucleotide are "operably associated" when they are placed into a functional relationship. This relationship can be between a coding region for a polypeptide and a regulatory sequence(s) which are connected in such a way as to permit expression of the coding region when the appropriate molecules (e.g., transcriptional activator proteins, polymerases, etc.) are bound to the regulatory sequences(s). "Transcriptional control regions" include, but are not limited to promoters, enhancers, operators, and transcription termination signals, and are included with the polynucleotide to direct its transcription. For example, a promoter would be operably associated with a nucleic acid molecule encoding an immunoglobulin subunit polypeptide if the promoter was capable of effecting transcription of that nucleic acid molecule. Generally, "operably associated" means that the DNA sequences are contiguous or closely connected in a polynucleotide. However, some transcription control regions, e.g., enhancers, do not have to be contiguous.

By "control sequences" or "control regions" is meant DNA sequences necessary for the expression of an operably associated coding sequence in a particular host organism. Eukaryotic cells are known to utilize promoters, polyadenylation signals, and/or enhancers.

A variety of transcriptional control regions are known to those skilled in the art. As will be discussed in more detail below, suitable transcriptional control regions include promoters capable of functioning in the cytoplasm of poxvirus-infected cells.

In certain embodiments, a fusion protein as described herein can comprise a linker, e.g., connecting the immunoglobulin variable domain to a constant domain, e.g., a CH1, C-kappa, or C-lambda domain, and/or connecting the constant domain to a polypeptide segment comprising the transmembrane domain of an EEV-specific membrane protein, e.g., A56R. A linker can comprise, e.g., at least about 5, at least about 10, or at least about 15 amino acids. Suitable linkers can be identified by a person of ordinary skill in the art.

Where a fusion protein described herein comprises a heavy chain constant region, e.g., a CH1 domain, any heavy chain constant region can be utilized, including, but not limited to immunoglobulin heavy chains from vertebrates such as birds, fish, or mammals, e.g., human immunoglobulin heavy chains. For example, a human immunoglobulin heavy chains or portion thereof, e.g., a CH1 domain can be µ heavy chain or fragment thereof, i.e., the heavy chain of an IgM immunoglobulin, a γ-1 heavy chain or fragment thereof, i.e., the heavy chain of an IgG1 immunoglobulin, a γ-2 heavy chain or fragment thereof, i.e., the heavy chain of an IgG2 immunoglobulin, a γ-3 heavy chain or fragment thereof, i.e., the heavy chain of an IgG3 immunoglobulin, a γ-4 heavy chain or fragment thereof, i.e., the heavy chain of an IgG4 immunoglobulin, an α-1 heavy chain or fragment thereof, i.e., the heavy chain of an IgA1 immunoglobulin, an α-2 heavy chain or fragment thereof, i.e., the heavy chain of an IgA2 immunoglobulin, an ε heavy chain or fragment thereof, i.e., the heavy chain of an IgE immunoglobulin, or a δ heavy chain or fragment thereof, i.e., the heavy chain of an IgD immunoglobulin.

Membrane bound fusion proteins as described herein can be anchored to the surface of a particle, e.g., a vaccinia virus particle (or virion), e.g., an EEV particle (or virion) by a transmembrane domain fused to the heavy chain polypeptide. In certain embodiments the transmembrane domain is part of a polypeptide segment comprising the transmembrane domain of an EEV-specific membrane protein, i.e., a protein which is expressed on the surface of an extracellular enveloped vaccinia virus, but NOT on intracellular vaccinia virus particles. In certain embodiments, the EEV-specific membrane protein, is A56R, the vaccinia HA protein. By "intracellular domain," "cytoplasmic domain," "cytosolic region," or related terms, which are used interchangeably herein, is meant the portion of the fusion polypeptide which is inside the cell.

In those embodiments where a fusion protein or other library protein comprises an immunoglobulin light chain or fragment thereof, any immunoglobulin light chain, from any animal species, can be used, e.g., immunoglobulin light chains from vertebrates such as birds, fish, or mammals e.g., human light chains, e.g., human κ and λ light chains. A light chain can associate with a heavy chain to produce an antigen-binding protein of an immunoglobulin molecule.

Each member of a library of polynucleotides encoding heavy chain fusion proteins as described herein can comprise (a) a first nucleic acid molecule encoding a first polypeptide segment comprising an immunoglobulin constant region common to all members of the library, e.g., a CH1 domain, e.g., a gamma or mu CH1 domain, (b) a second nucleic acid molecule encoding a second polypeptide segment comprising the extracellular and transmembrane domains of a vaccinia extracellular enveloped virus (EEV)-specific membrane protein (e.g., A56R), where the second nucleic acid molecule is directly downstream and in-frame with the first nucleic acid molecule (either directly fused or connected by a linker), and (c) an a third nucleic acid molecule encoding a third polypeptide segment comprising an immunoglobulin heavy chain variable region, where the third nucleic acid molecule is directly upstream of and in-frame with the first nucleic acid molecule (either directly fused or connected by a linker).

Each member of a library of polynucleotides encoding light chain fusion proteins as described herein can comprise (a) a first nucleic acid molecule encoding a first polypeptide segment comprising an immunoglobulin constant region common to all members of the library, e.g., a C-kappa or C-lambda domain, (b) a second nucleic acid molecule encoding a second polypeptide segment comprising the extracellular and transmembrane domains of a vaccinia extracellular enveloped virus (EEV)-specific membrane protein (e.g., A56R), where the second nucleic acid molecule is directly downstream and in-frame with the first nucleic acid molecule (either directly fused or connected by a linker), and (c) an a third nucleic acid molecule encoding a third polypeptide segment comprising an immunoglobulin light chain variable region, where the third nucleic acid molecule is directly upstream of and in-frame with the first nucleic acid molecule (either directly fused or connected by a linker).

Libraries of immunoglobulin heavy chains or light chains that are not fused to a polypeptide segment comprising the transmembrane domain of an EEV-specific membrane protein can be used to coinfect host cells to provide the "complementary" immunoglobulin chain to produce a functional antigen-binding immunoglobulin fragment. Such libraries are described in detail in, e.g., U.S. Pat. No. 7,858,559.

Libraries of polynucleotides encoding heavy or light chain variable regions can contain a plurality, i.e., at least two, or at least 10, 100, $10^3$, $10^4$, $10^5$, $10^6$, $10^7$, $10^8$, or $10^9$ different variable regions. As is well known by those of ordinary skill in the art, a light chain variable region is encoded by rearranged nucleic acid molecules, each comprising a light chain $V_L$ region, specifically a Vκ region or a Vλ region, and a light chain J region, specifically a Jκ region or a Jλ region. Similarly, a heavy chain variable region is encoded by rearranged nucleic acid molecules, each comprising a heavy chain $V_H$ region, a D region and J region. These rearrangements take place at the DNA level upon cellular differentiation. Nucleic acid molecules encoding heavy and light chain variable regions can be derived, for example, by PCR from mature B cells and plasma cells which have terminally differentiated to express an antibody with specificity for a particular epitope. Furthermore, if antibodies to a specific antigen are desired, variable regions can be isolated from mature B cells and plasma cells of an animal that has been immunized with that antigen, and has thereby produced an expanded repertoire of antibody variable regions which interact with the antigen. Alternatively, if a more diverse library is desired, variable regions can be isolated from precursor cells, e.g., pre-B cells and immature B cells, which have undergone rearrangement of the immunoglobulin genes, but have not been exposed to antigen, either self or non-self. For example, variable regions can be isolated by RT-PCR from normal human bone marrow pooled from multiple donors. Alternatively, variable regions can be synthetic, for example, made in the laboratory through generation of synthetic oligonucleotides, or can be derived through in vitro manipulations of germ line DNA resulting in rearrangements of the immunoglobulin genes.

In addition to first and second nucleic acid molecules encoding immunoglobulin constant regions and variable regions, respectively, each member of a library of polynucleotides of the present invention as described above can further comprise an additional nucleic acid molecule encoding a signal peptide directly upstream of and in frame with the nucleic acid molecule encoding the variable region.

By "signal peptide" is meant a polypeptide sequence which, for example, directs transport of nascent immunoglobulin polypeptide subunit to the surface of the host cells. Signal peptides are also referred to in the art as "signal sequences," "leader sequences," "secretory signal peptides," or "secretory signal sequences." Signal peptides are normally expressed as part of a complete or "immature" polypeptide, and are normally situated at the N-terminus.

All cells, including host cells of the present invention, possess a constitutive secretory pathway, where proteins, including secreted immunoglobulin subunit polypeptides destined for export, are secreted from the cell. These proteins pass through the ER-Golgi processing pathway where modifications can occur. If no further signals are detected on the protein it is directed to the cell's surface for secretion or insertion as an integral membrane component expressed on the surface of the host cell or virus particle, e.g., EEV virion. Membrane-bound forms of immunoglobulin subunit polypeptides initially follow the same pathway as the secreted forms, passing through to the ER lumen, except that they are retained in the ER membrane by the presence of stop-transfer signals, or "transmembrane domains." Transmembrane domains are hydrophobic stretches of about 20 amino acid residues that adopt an alpha-helical conformation as they transverse the membrane. Membrane embedded proteins are anchored in the phospholipid bilayer of the plasma membrane. As with secreted proteins, the N-terminal region of transmembrane proteins have a signal peptide that passes through the membrane and is cleaved upon exiting into the lumen of the ER.

Newly synthesized immunoglobulin heavy chains are held in residence in the ER by a chaperone protein called BiP (a member of the Hsp70 molecular chaperone family). Pairing of the heavy chain CH1 domain with the CL domain of its partner light chain induces dissociation of BiP, final folding and disulfide bond formation, and egress of the assembled antibody from the ER. The antibody then utilizes the normal secretion pathway of the cell, and traffics through the Golgi to the cell surface, where it is either secreted, or retained on the surface (if the antibody has a transmembrane domain). See Daniel et al., Molecular Cell 34:635-36 (2009).

Suitable signal peptides provided herein can be either a naturally-occurring immunoglobulin signal peptides, i.e., encoded by a sequence which is part of a naturally occurring heavy or light chain transcript, or a functional derivative of that sequence that retains the ability to direct the secretion of the immunoglobulin subunit polypeptide that is operably associated with it. Alternatively, a heterologous signal peptide, or a functional derivative thereof, can be used. In certain aspects, the signal peptide can be that of the vaccinia virus A56R protein, or a functional derivative thereof.

In other aspects, members of a library of polynucleotides as described herein can further comprise additional nucleic acid molecules encoding heterologous polypeptides. Such additional nucleic acid molecules encoding heterologous polypeptides can be upstream of or downstream from the nucleic acid molecules encoding an immunoglobulin variable or constant domain, or the EEV-specific membrane protein.

A heterologous polypeptide encoded by an additional nucleic acid molecule can be a rescue sequence. A rescue sequence is a sequence which can be used to purify or isolate either the immunoglobulin or fragment thereof or the polynucleotide encoding it. Thus, for example, peptide rescue sequences include purification sequences such as the 6-His tag for use with Ni affinity columns and epitope tags for detection, immunoprecipitation, or FACS (fluorescence-activated cell sorting). Suitable epitope tags include myc (for use with commercially available 9E10 antibody), the BSP biotinylation target sequence of the bacterial enzyme BirA, flu tags, LacZ, and GST. The additional nucleic acid molecule can also encode a peptide linker.

The polynucleotides comprised in various libraries described herein can be introduced into suitable host cells. Suitable host cells can be characterized by, e.g., being capable of expressing immunoglobulin molecules attached to their surface or by being permissive for vaccinia virus infectivity. Polynucleotides can be introduced into host cells by methods which are well known to those of ordinary skill in the art. Where the polynucleotide is part of a virus vector, e.g., a vaccinia virus, introduction into host cells is conveniently carried out by standard infection.

The first and second libraries of polynucleotides can be introduced into host cells in any order, or simultaneously. For example, if both the first and second libraries of polynucleotides are constructed in vaccinia virus vectors, whether infectious or inactivated, the vectors can be introduced by simultaneous infection as a mixture, or can be introduced in consecutive infections. If one library is constructed in a vaccinia virus vector, and the other is constructed in a plasmid vector, introduction can be carried out by introduction of one library before the other.

Following introduction into the host cells of the first and second libraries of polynucleotides, expression of immunoglobulin molecules, or antigen-specific fragments thereof on the surface of EEV, is permitted to occur. By "permitting expression" is meant allowing the vectors which have been introduced into the host cells to undergo transcription and translation of the immunoglobulin subunit polypeptides, allowing the host cells to transport fully assembled immunoglobulin molecules, or antigen-specific fragments thereof, to the membrane surface as a fusion with a polypeptide segment comprising the transmembrane domain of an EEV-specific membrane protein. Typically, permitting expression requires incubating the host cells into which the polynucleotides have been introduced under suitable conditions to allow expression. Those conditions, and the time required to allow expression will vary based on the choice of host cell and the choice of vectors, as is well known by those of ordinary skill in the art.

In certain embodiments, host cells and/or vaccinia virions which have been allowed to express immunoglobulin molecules on their surface, or soluble immunoglobulin molecules secreted into the cell medium are then contacted with an antigen. As used herein, an "antigen" is any molecule that can specifically bind to an antibody, immunoglobulin molecule, or antigen-specific fragment thereof. By "specifically bind" is meant that the antigen binds to the CDR of the antibody. The portion of the antigen which specifically interacts with the CDR is an "epitope," or an "antigenic determinant." An antigen can comprise a single epitope, but typically, an antigen comprises at least two epitopes, and can include any number of epitopes, depending on the size, conformation, and type of antigen.

Antigens are typically peptides or polypeptides, but can be any molecule or compound. For example, an organic compound, e.g., dinitrophenol or DNP, a nucleic acid, a carbohydrate, or a mixture of any of these compounds either with or without a peptide or polypeptide can be a suitable antigen. The minimum size of a peptide or polypeptide epitope is thought to be about four to five amino acids. Peptide or polypeptide epitopes can contain at least seven, at least nine, or between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, peptide or polypeptide antigens can contain a sequence of at least 4, at least 5, at least 6, at least 7, at least 8, at least 9, at least 10, at least 15, at least 20, at least 25, and between about 15 to about 30 amino acids. In certain embodiments, peptides or polypeptides comprising, or alternatively consisting of, antigenic epitopes are at least 10, 15, 20, 25, 30, 35, 40, 45, 50, 55, 60, 65, 70, 75, 80, 85, 90, 95, or 100 amino acid residues in length. The antigen can be in any form and can be free, for example dissolved in a solution, or can be attached to any substrate. Suitable substrates are disclosed herein. In certain embodiments, an antigen can be part of an antigen-expressing vaccinia virus, e.g., EEV virion as described in more detail below.

Immunoglobulin molecules specific for any antigen can be produced according to the methods disclosed herein. In certain embodiments, antigens are "self" antigens, i.e., antigens derived from the same species as the immunoglobulin molecules produced. As an example, it might be desired to produce human antibodies directed to human tumor antigens. Other desired "self" antigens include, but are not limited to, cytokines, receptors, ligands, glycoproteins, and hormones.

Antibodies directed to antigens on infectious agents can also be identified and selected by the disclosed methods. Examples of such antigens include, but are not limited to, bacterial antigens, viral antigens, parasite antigens, and fungal antigens.

In certain selection and screening schemes in which immunoglobulin molecules are expressed on the surface of EEV, the recombinant EEV virions produced as described are "contacted" with antigen by a method which will allow an antigen, which specifically recognizes a CDR of an immunoglobulin molecule expressed on the surface of the EEV, to bind to the CDR, thereby allowing recombinant EEV virions which specifically bind the antigen to be distinguished from those EEV virions which do not bind the antigen. Any method which allows recombinant EEV virions expressing an antigen-specific binding domain of an antibody to interact with the antigen is included. For example, if the EEV virions are in suspension, and the antigen is attached to a solid substrate, recombinant EEV virions which specifically bind to the antigen will be trapped on the solid substrate, allowing those virions which do not bind the antigen to be washed away, and the bound recombinant EEV virions to be subsequently recovered. Methods by which to allow recombinant EEV virions to contact antigen, are disclosed herein.

After recovery of recombinant EEV virions which specifically bind antigen, polynucleotides of the first library can be recovered from those EEV virions. By "recovery" is meant a crude separation of a desired component from those components which are not desired. For example, recombinant EEV virions which bind antigen can be "recovered" based on their attachment to antigen-coated solid substrates, e.g., magnetic beads, which can then be separated with a magnet.

Recovery of polynucleotides can be accomplished by any standard method known to those of ordinary skill in the art. In certain embodiments, the polynucleotides are recovered by harvesting infectious EEV virions which bound antigen.

As will be readily appreciated by those of ordinary skill in the art, identification of polynucleotides encoding immunoglobulin fusion polypeptides can require two or more rounds of selection as described above, and will necessarily require two or more rounds of screening as described above. A single round of selection may not necessarily result in isolation of a pure set of polynucleotides encoding the desired first immunoglobulin fusion polypeptides; the mixture obtained after a first round can be enriched for the desired polynucleotides but may also be contaminated with non-target insert sequences. Accordingly, the first selection step, as described, can, or must be repeated one or more times, thereby enriching for the polynucleotides encoding the desired immunoglobulin fusion polypeptides. In order to repeat the first step of this embodiment, EEV comprising those polynucleotides recovered as described above, can be introduced via infection into a population of host cells. The second library of polynucleotides are also introduced into these host cells, e.g, by infection with vaccinia virus capable of expressing the complementary immunoglobulin molecules (e.g., light chains) encoded by the polynucleotides in the library, and expression of immunoglobulin molecules, or antigen-specific fragments thereof, on the membrane surface of the recombinant EEV virions, is permitted. The recombinant EEV virions are similarly contacted with antigen, and polynucleotides of the first library are again recovered from EEV virions, which express an immunoglobulin molecule that specifically binds antigen. These steps can be repeated one or more times, resulting in enrichment for polynucleotides derived from the first library which encode an immunoglobulin fusion polypeptide which, as part of an immunoglobulin molecule, or antigen-specific fragment thereof, specifically binds the antigen and/or has a desired functional characteristic.

Following suitable enrichment for the desired polynucleotides from the first library as described above, those polynucleotides which have been recovered are "isolated," i.e., they are substantially removed from their native environment and are largely separated from polynucleotides in the library which do not encode antigen-specific immunoglobulin fusion polypeptides. For example, cloned polynucleotides contained in a vector are considered isolated. It is understood that two or more different immunoglobulin fusion polypeptides which, when combined with, e.g., a light chain, specifically bind the same antigen can be recovered by the methods described herein. Accordingly, a mixture of polynucleotides which encode polypeptides binding to the same antigen is also considered to be "isolated." Further examples of isolated polynucleotides include those maintained in heterologous host cells, in recombinant vaccinia, e.g., EEV virions, or purified (partially or substantially) DNA molecules in solution. However, a polynucleotide contained in a clone that is a member of a mixed library and that has not been isolated from other clones of the library, e.g., by virtue of encoding an antigen-specific immunoglobulin fusion polypeptide, is not "isolated" for the purposes of this invention. For example, a polynucleotide contained in a virus vector is "isolated" after it has been recovered, and optionally plaque purified.

Given that an antigen can comprise two or more epitopes, and several different immunoglobulin molecules can bind to any given epitope, it is contemplated that several suitable polynucleotides, e.g., two, three, four, five, ten, 100 or more polynucleotides, can be recovered from the first step of this embodiment, all of which can encode an immunoglobulin fusion polypeptide which, when combined with a suitable immunoglobulin subunit polypeptide encoded by a preselected polynucleotide or a polynucleotide of the second library, will form an immunoglobulin molecule, or antigen binding fragment thereof, capable of specifically binding the antigen of interest. It is contemplated that each different polynucleotide recovered from the first library would be separately isolated.

Once one or more suitable polynucleotides from the first library are isolated, in the second step of this embodiment, one or more polynucleotides are identified in the second library which encode immunoglobulin subunit polypeptides which are capable of associating with the immunoglobulin fusion polypeptide(s) encoded by the polynucleotides isolated from the first library to form an immunoglobulin molecule, or antigen-binding fragment thereof, which specifically binds an antigen of interest.

Provided herein are vaccinia virus vectors for expression of antigen-binding molecules, where the antigen binding molecule, e.g., an immunoglobulin heavy chain variable region and CH1, is expressed as a fusion with an EEV-specific membrane protein. In certain embodiments, heavy chains can be recovered as EEV fusion proteins, and libraries of light chains, or individual pre-selected light chains can be expressed as soluble proteins in vaccinia virus, or other vectors, e.g., plasmid vectors.

In certain aspects, inactivation of viruses expressing a soluble complementary chain, e.g., a light chain, can be carried out with 4'-aminomethyl-trioxsalen (psoralen) and then exposing the virus vector to ultraviolet (UV) light. Psoralen and UV inactivation of viruses is well known to those of ordinary skill in the art. See, e.g., Tsung, K., et al., *J. Virol.* 70:165-171 (1996), which is incorporated herein by reference in its entirety.

The ability to assemble and express immunoglobulin molecules or antigen-specific fragments thereof in eukaryotic cells from two libraries of polynucleotides encoding immunoglobulin subunit polypeptides, where one subunit is expressed as a fusion with an EEV-specific membrane protein provides a significant improvement over the methods of producing single-chain antibodies in bacterial systems, in that the two-step selection process can be the basis for selection of immunoglobulin molecules or antigen-specific fragments thereof with a variety of specificities.

Vaccinia EEV vectors. Poxviruses are unique among DNA viruses because they replicate only in the cytoplasm of the host cell, outside of the nucleus. During its replication cycle, vaccinia virus produces four infectious forms which differ in their outer membranes: intracellular mature virion (IMV), the intracellular enveloped virion (IEV), the cell-associated enveloped virion (CEV) and the extracellular enveloped virion (EEV). The prevailing view is that the IMV consists of a single lipoprotein membrane, while the CEV and EEV are both surrounded by two membrane layers and the IEV has three envelopes. EEV is shed from the plasma membrane of the host cell and the EEV membrane is derived from the trans-Golgi.

After infection, the virus loses its membrane(s) and the DNA/protein core is transported along microtubules into the cell. The proteins encoded by early vaccinia mRNAs ("early" is defined as pre-DNA replication) lead to uncoating of the vaccinia core and subsequent DNA replication. This replication occurs in what are termed "viral factories" which are located essentially on top of the ER. Within the viral factory, immature virions (IV) assemble and are processed to form IMV (Intracellular Mature Virus). IMVs contain a membrane that is derived from the ER. The majority of IMVs are released from the cell by cell lysis. Some IMVs are transported on microtubules to sites of wrapping by membranes of the trans-Golgi network or early endosomes. The wrapping of the IMV particles by a double membrane creates a form of vaccinia called IEVs (Intracellular Enveloped Virus). The IEVs are then transported to the cell surface on microtubules. The outer IEV membrane fuses with the plasma membrane to expose a CEV (Cell Associated Enveloped Virus) at the cell surface. Actin polymerization from the host cell can drive the CEV to infect neighboring cells, or the virus can be released as an EEV. See, e.g., Kim L. Roberts and Geoffrey L. Smith. Trends in Microbiology 16(10):472-479 (2008); Geoffrey L. Smith, et al., Journal of General Virology 83:2915-2931 (2002).

At least six virus-encoded proteins have been reported as components of the EEV envelope. Of these, four proteins (A33R, A34R, A56R, and B5R) are glycoproteins, one (A36R) is a nonglycosylated transmembrane protein, and one (F13L) is a palmitoylated peripheral membrane protein. See, e.g., Lorenzo et al., Journal of Virology 74(22):10535 (2000). During infection, these proteins localize to the Golgi complex, where they are incorporated into infectious virus that is then transported and released into the extracellular medium. As provided herein, immunoglobulin fusion polypeptides, e.g., variable heavy chains are bound to the EEV membrane, e.g., as a fusion protein with an EEV-specific membrane protein, e.g., A56R.

EEV fusion proteins as provided herein can be expressed in any suitable vaccinia virus. In certain embodiments, the DNA encoding an EEV fusion protein can be inserted into a region of the vaccinia virus genome which is non-essential for growth and replication of the vector so that infectious viruses are produced. Although a variety of non-essential regions of the vaccinia virus genome have been characterized, the most widely used locus for insertion of foreign genes is the thymidine kinase locus, located in the HindIII J fragment in the genome.

Libraries of polynucleotides encoding immunoglobulin fusion polypeptides are inserted into vaccinia virus vectors, under operable association with a transcriptional control region which functions in the cytoplasm of a poxvirus-infected cell.

Poxvirus transcriptional control regions comprise a promoter and a transcription termination signal. Gene expression in poxviruses is temporally regulated, and promoters for early, intermediate, and late genes possess varying structures. Certain poxvirus genes are expressed constitutively, and promoters for these "early-late" genes bear hybrid structures. Synthetic early-late promoters have also been developed. See Hammond J. M., et al., *J. Virol. Methods* 66:135-8 (1997); Chakrabarti S., et al., *Biotechniques* 23:1094-7 (1997). For embodiments disclosed herein, any poxvirus promoter can be used, but use of early, late, or constitutive promoters can be desirable based on the host cell and/or selection scheme chosen. In certain embodiments, a constitutive promoters is used. A suitable promoter for use in the methods described herein is the early/late 7.5-kD promoter, or the early/late H5 promoter (or variants thereof).

The Tri-Molecular Recombination Method. Traditionally, poxvirus vectors such as vaccinia virus have not been used to identify previously unknown genes of interest from a complex libraries because a high efficiency, high titer-producing method of constructing and screening libraries did not exist for vaccinia. The standard methods of heterologous protein expression in vaccinia virus involve in vivo homologous recombination and in vitro direct ligation. Using homologous recombination, the efficiency of recombinant virus production is in the range of approximately 0.1% or less. Although efficiency of recombinant virus production using direct ligation is higher, the resulting titer is relatively low. Thus, the use of vaccinia virus vector has been limited to the cloning of previously isolated DNA for the purposes of protein expression and vaccine development.

Tri-molecular recombination, as disclosed in Zauderer, PCT Publication No. WO 00/028016 and in U.S. Pat. No. 7,858,559, is a high efficiency, high titer-producing method for producing libraries in vaccinia virus. Using the tri-molecular recombination method, the present inventor has achieved generation of recombinant viruses at efficiencies of at least 90%, and titers at least at least 2 orders of magnitude higher than those obtained by direct ligation.

In certain embodiments, libraries of polynucleotides capable of expressing immunoglobulin fusion polypeptides as described herein can be constructed in poxvirus vectors, e.g., vaccinia virus vectors, by tri-molecular recombination.

In certain embodiments, a transfer plasmid for producing libraries of fusion polypeptides is provided, which comprises a polynucleotide encoding an immunoglobulin heavy chain CH1 and at least the transmembrane portion of a vaccinia virus A56R protein through operable association with a vaccinia virus H5 promoter. An exemplary vector is promoter is pJEM1, which comprises the sequence:

AAAAAATGAAAATAAATACAAAGGTTCTTGAGGGTTGTGTTAAATTGAAAGCGAGAAATAATCATAAAT

TCCATGGGATGGAGCTGTATCATCCTCTTCTTGGTAGCAACAGCTACAG*GCGCGC*ACTCCGAGATCCAG

CTGGTGCAGAGCGGCCCTGAGCTGAAGCAGCCTGGCGAGACCGTGAGGATCAGCTGCAAGGCCAGCGGC

TACACCTTCACCAACTACGGCATGAACTGGGTGAAGCAGGCCCCTGGCAAGGGCCTGAAGTGGATGGGC

TGGATCAACACCTACACCGGCGAGCCTACCTACGCCGCCGACTTCAAGAGGAGGTTCACCTTCAGCCTG

GAGACCAGCGCCAGCACCGCCTACCTGCAGATCAGCAACCTGAAGAACGACGACACCGCCACCTACTTC

TGCGCCAAGTACCCTCACTACTACGGCAGCAGCCACTGGTACTTCGACGTGTGGGGCGCCGGCACCAC*G*

*GTCACC*GTCTCCTCAGCCTCCACCAAGGGCCCATCGGTCTTCCCCCTGGCACCCTCCTCCAAGAGCACC

-continued

TCTGGGGGCACAGCGGCCCTGGGCTGCCTGGTCAAGGACTACTTCCCCGAACCGGTGACGGTGTCGTGG

AACTCAGGCGCCCTGACCAGCGGCGTGCACACCTTCCCGGCTGTCCTACAGTCCTCAGGACTCTACTCC

CTCAGCAGCGTCGTGACCGTGCCCTCCAGCAGCTTGGGCACCCAGACCTACATCTGCAACGTGAATCAC

AAGCCCAGCAACACCAAGGTGGACAAGAAAGTTACATCAACTACAAATGACACTGATAAAGTAGATTAT

GAAGAATACTCCACAGAGTTGATTGTAAATACAGATAGTGAATCGACTATAGACATAATACTATCTGGA

TCTACACATTCACCGGAAACTAGTTCTAAGAAACCTGATTATATAGATAATTCTAATTGCTCGTCGGTA

TTCGAAATCGCGACTCCGGAACCAATTACTGATAATGTAGAAGATCATACAGACACCGTCACATACACT

AGTGATAGCATTAATACAGTAAGTGCATCATCTGGAGAATCCACAACAGACGAGACTCCGGAACCAATT

ACTGATAAAGAAGATCATACAGTTACAGACACTGTCTCATACACTACAGTAAGTACATCATCTGGAATT

GTCACTACTAAATCAACCACCGATGATGCGGATCTTTATGATACGTACAATGATAATGATACAGTACCA

CCAACTACTGTAGGCGGTAGTACAACCTCTATTAGCAATTATAAAACCAAGGACTTTGTAGAAATATTT

GGTATTACCGCATTAATTATATTGTCGGCCGTGGCAATTTTCTGTATTACATATTATATATATAATAAA

CGTTCACGTAAATACAAAACAGAGAACAAAGTCTAG

Double underline - H5 promoter
Single underline - Leader peptide
Squiggly underline - Representative Heavy Variable region
Bold underline - IgG CH1 domain
No underline - Vaccinia A56R
Bold italics - BssHII and BstEII variable gene cloning site designated herein as SEQ ID NO:1. Various different PCR-amplified heavy chain variable regions can be inserted in-frame into unique BssHII and BstEII sites, which are indicated above in bold italics.

Plasmid pJEM1 is a derivative of p7.5/tk described in U.S. Pat. No. 7,858,559. pJEM1 retains the flanking regions of homology to the vaccinia genome which enables recombination as is described in U.S. Pat. No. 7,858,559. However, in place of the expression cassette in p7.5/tk (promoter and expressed sequences), pJEM1 contains the following elements:

Vaccinia Virus H5 Promoter
Leader Peptide
5' BssHII Cloning site for cloning variable heavy chains
Heavy Variable region
3' BstEII Cloning site for cloning variable heavy chains
IgG CH1 domain
vaccinia A56R These elements are listed in FIG. 1 and SEQ ID NO: 1. This cassette can be created synthetically.

In another embodiment, the transfer plasmid of the present invention which comprises a polynucleotide encoding an immunoglobulin kappa light chain polypeptide through operable association with a vaccinia virus p7.5 promoter is pVKE, which comprises the sequence:

GGCCAAAAATTGAAAAACTAGATCTATTTATTGCACGCGGCCGCCCATGG

GATGGAGCTGTATCATCCTCTTCTTGGTAGCAACAGCTACAGGC*GTGCAC*T

TG*ACTCGAG*ATCAAACGAACTGTGGCTGCACCATCTGTCTTCATCTTCCCG

CCATCTGATGAGCAGTTGAAATCTGGAACTGCCTCTGTTGTGTGCCTGCT

GAATAACTTCTATCCCAGAGAGGCCAAAGTACAGTGGAAGGTGGATAACG

CCCTCCAATCGGGTAACTCCCAGGAGAGTGTCACAGAGCAGGACAGCAAG

GACAGCACCTACAGCCTCAGCAGCACCCTGACGCTGAGCAAAGCAGACTA

CGAGAAACACAAAGTCTACGCCTGCGAAGTCACCCATCAGGGCCTGAGCT

CGCCCGTCACAAAGAGCTTCAACAGGGGAGAGTGTTAGGTCGAC designated herein as SEQ ID NO:2. PCR-amplified kappa light chain variable regions can be inserted in-frame into unique ApaLI), and XhoI sites, which are indicated above in bold.

Furthermore, pVKE can be used in those embodiments where it is desired to have polynucleotides of the second library in a plasmid vector during the selection of polynucleotides of the first library as described above.

In another embodiment, the transfer plasmid of the present invention which comprises a polynucleotide encoding an immunoglobulin lambda light chain polypeptide through operable association with a vaccinia virus p7.5 promoter is pVLE, which comprises the sequence:

GGCCAAAAATTGAAAAACTAGATCTATTTATTGCACGCGGCCGCCCATGG

GATGGAGCTGTATCATCCTCTTCTTGGTAGCAACAGCTACAGGCGTGCAC

TTGACTCGAGAAGCTTACCGTCCTACGAACTGTGGCTGCACCATCTGTCT

TCATCTTCCCGCCATCTGATGAGCAGTTGAAATCTGGAACTGCCTCTGTT

GTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGC

AGGACAGCAAGGACAGCACCTACAGCCTCAGCAGCACCCTGACGCTGAGC

AAAGCAGACTACGAGAAACACAAAGTCTACGCCTGCGAAGTCACCCATCA

GGGCCTGAGCTCGCCCGTCACAAAGAGCTTCAACAGGGGAGAGTGTTAGG

TCGAC designated herein as SEQ ID NO:3. PCR-amplified lambda light chain variable regions can be inserted in-frame into unique ApaLI and HindIII sites, which are indicated above in bold.

Furthermore, pVLE can be used in those embodiments where it is desired to have polynucleotides of the second library in a plasmid vector during the selection of polynucleotides of the first library as described above.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986); and in Ausubel et al., *Current Protocols in Molecular Biology*, John Wiley and Sons, Baltimore, Md. (1989).

General principles of antibody engineering are set forth in *Antibody Engineering*, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, Mass. (1984); and Steward, M. W., Antibodies, Their Structure and Function, Chapman and Hall, New York, N.Y. (1984). Additionally, standard methods in immunology known in the art and not specifically described are generally followed as in *Current Protocols in Immunology*, John Wiley & Sons, New York; Stites et al. (eds), *Basic and Clinical-Immunology* (8th ed.), Appleton & Lange, Norwalk, Conn. (1994) and Mishell and Shiigi (eds), *Selected Methods in Cellular Immunology*, W. H. Freeman and Co., New York (1980).

Standard reference works setting forth general principles of immunology include *Current Protocols in Immunology*, John Wiley & Sons, New York; Klein, J., *Immunology: The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, Elsevier, Amsterdam (1984).

EXAMPLES

Example 1: Preparation of CH1-A56R Fusion Protein

Heavy Chain fusion proteins were constructed to facilitate selection of specific immunoglobulin segments expressed on the cell surface of recombinant vaccinia virus.

An expression vector encoding a fusion protein including the human heavy chain CH1 domain of C gamma fused to the extracellular and transmembrane domains of A56R from Western Reserve Vaccinia virus, designated herein as CH1-A56R, as well as a C35-specific VH (H2124) was constructed by the following method.

pJEM1. An expression vector comprising a polynucleotide sequence encoding the human gamma immunoglobulin constant region (CH1), a fragment of vaccinia A56R, and a cassette for insertion of a human heavy chain variable region (e.g., H2124), designated herein as "pJEM1" was constructed. In short, p7.5/tk, produced as described in PCT Publication No. WO 00/028016, incorporated herein by reference in its entirety, was converted into pJEM1 by the following method.

IgG CH1. A cDNA coding for the human IgG heavy chain was isolated from bone marrow RNA using SMART™ RACE cDNA Amplification Kit available from Clontech, Palo Alto, Calif. The PCR was carried out using the 5' primer huCγ1-5B: 5' ATTAGGATCC GGTCACCGTC TCCTCA-GCC 3' (SEQ ID NO:4), and 3' primer huCγ1-3S: 5' ATT-AGTCGAC TCATTTACCC GGAGACAGGG AGAG 3' (SEQ ID NO:5). The PCR product comprised the following elements: BamHI-BstEII-(nucleotides encoding amino acids 111-113 of VH)-(nucleotides encoding amino acids 114-478 of Cγ1)-TGA-SalI. This product was subcloned into pBluescriptII/KS at BamHI and SalI sites, and a second BstEII site corresponding to amino acids 191 and 192 within the CH1 domain of Cγ1 was removed by site-directed mutagenesis without change to the amino acid sequence. Plasmid pBluescriptII/KS was digested with BstEII and SalI and the smaller DNA fragment of about 1 Kb was gel purified. This smaller fragment was then used as a template in a PCR reaction using forward primer CH1(F)-5'-CAAGGGACCC T<u>GGTCACC</u>GT CTCCTCAGCC TCC-3' (SEQ ID NO:6) (BstEII restriction site in italics and underlined) and reverse primer CH1(R) 5'-AACTTTCTTG TCCACCTTGG TGTTG-3' (SEQ ID NO:7). The resulting PCR product of about 320 base pairs was gel purified.

Full Length IgG. A cDNA coding for the human IgG heavy chain was isolated from bone marrow RNA using SMART™ RACE cDNA Amplification Kit available from Clontech, Palo Alto, Calif. The PCR was carried out using the 5' primer huCγ1-5B: (SEQ ID NO:4), and 3' primer huCγ1-3S: (SEQ ID NO:5). The PCR product comprised the following elements: BamHI-BstEII-(nucleotides encoding amino acids 111-113 of VH)-(nucleotides encoding amino acids 114-478 of Cγ1)-TGA-SalI. This product was subcloned into pBluescriptII/KS at BamHI and SalI sites, and a second BstEII site corresponding to amino acids 191 and 192 within the CH1 domain of Cγ1 was removed by site-directed mutagenesis without change to the amino acid sequence. Plasmid pBluescriptII/KS was digested with BstEII and SalI and the 993 base pair DNA fragment corresponding to full length IgG1 was gel purified.

A56R (longer form). A DNA fragment encoding amino acids 108 to 314 of the A56R hemagglutinin protein from vaccinia virus (Western Reserve), which comprises the stalk, transmembrane, and intracellular domains (GenBank accession No. YP_233063) was amplified from isolated Western Reserve Vaccinia Virus DNA with forward primer A56R(F) 5'-CAACACCAAG GTGGACAAGA AAGTTACATC AACTACAAAT GACACTGATA G-3' (SEQ ID NO:8) and reverse primer A56R(R) 5'-TATA<u>GTCGAC</u> CTAGACTTTG TTCTCTGTTT TGTATTTACG-3' (SEQ ID NO:9) (SalI restriction site in italics and underlined). The resulting PCR product of about 660 base pairs was gel purified.

A56R (shorter form). A DNA fragment encoding amino acids 240 to 314 of the A56R hemagglutinin protein from vaccinia virus (Western Reserve), which comprises the stalk, transmembrane, and intracellular domains (GenBank accession No. YP_233063) was amplified from isolated Western Reserve Vaccinia Virus DNA with forward primer A56R (F2): 5'-CAACACCAAG GTGGACAAGA AAGTTACCAC CGATGATGCG GATCTTTATG A-3' (SEQ ID NO:21) and reverse primer A56R(R): (SEQ ID NO:9) The resulting PCR product of about 263 base pairs was gel purified.

The Fab construct (IgG CH1 with A56R longer form). The 320 and 660-base pair fragments were then combined by SOE PCR using forward primer CH1(F) (SEQ ID NO:6) and reverse primer CH1 (R2): 5'-ACAAAAGTAT TGGTAATCGT GTCATAACT TTCTTGTCCA CCTTGGTGTT G-3' (SEQ ID NO:22) for the 5' product and A56R (F) (SEQ ID NO:8) in combination with A56R(R) (SEQ ID NO:9) for the 3' product. These two products were then combined to produce a fusion fragment of about 980 base pairs. This fragment was digested with BstEII and SalI, and the resulting 934-base pair fragment was gel purified.

The TR construct (Full Length IgG1 with A56R shorter form). The 993 and 263-base pair fragments were combined by SOE PCR using forward primer CH1(F): (SEQ ID NO:6) and reverse primer A56R(R2): 5'-TCATAAAGAT CCGCATCATC GGTGGTTTTA CCCGGAGACA GGGAGAGGCT C-3' (SEQ ID NO:23) for the 5' product and A56R(F3): 5'-GAGCCTCTCC CTGTCTCCGG GTAAAACCAC CGATGATGCG GATCTTTATG A-3' (SEQ ID NO:24) in combination with A56R(R): (SEQ ID NO:9) for the 3' product. These two products were then combined to produce a fusion fragment of about 1256 base pairs. This fragment was digested with BstEII and SalI, and the resulting 1235-base pair fragment was gel purified.

The FL construct (Full Length IgG1 with A56R longer form). The 993 and 660-base pair fragments were combined by SOE PCR using forward primer CH1(F): (SEQ ID NO:6) and reverse primer A56R(R3): 5'-TATCAGTGTC ATTTGTAGTT GATGTTTTAC CCGGAGACA GGGAGAGGCT C-3' (SEQ ID NO:25) for the 5' product and A56R (F4): 5'-GAGCCTCTCC CTGTCTCCGG GTAAAACATC AACTACAAAT GACACTGATA-3' (SEQ ID NO:26) in combination with A56R(R) (SEQ ID NO:9) for the 3' product. These two products were then combined to produce a fusion fragment of about 1653-base pairs. This fragment was digested with BstEII and SalI, and the resulting 1632-base pair fragment was gel purified.

Plasmid p7.5/tk was also digested with BstEII and SalI, and the larger resulting fragment of about 5.7 Kb was gel purified. These two BstEII/SalI fragments were then ligated to produce the pJEM1 plasmid.

pJEM1 retains the flanking regions of homology to the vaccinia genome which enables recombination. However, in place of the expression cassette in p7.5/tk (promoter and expressed sequences), pJEM1 contains the following elements: Vaccinia Virus H5 promoter; Leader peptide; 5' BssHII Cloning site for cloning variable heavy chains; Heavy Variable region; 3' BstEII Cloning site for cloning variable heavy chains; IgG CH1 domain; and Vaccinia A56R, the sequence for these elements of pJEM1 are shown in FIG. 1 and SEQ ID NO:1.

The heavy chain variable region (H2124), specific for C35, was inserted into the BssHII and BstEII sites of pJEM1 producing a VH (H2124)-CH1-A56R fusion construct. The nucleotide and amino acid sequences for the VH (H2124)-CH1-A56R fusion construct prepared in pJEM1 are shown below, respectively.

Polynucleotide Sequence Encoding VH (H2124)-CH1-A56R Fab Product Fusion Protein (SEQ ID NO:10):

CAGGTGCAGCTGCAGCAGTGGGGCGCAGGACTGCTGAAGCCTAGCGAGAC

CCTGTCCCTCACCTGCGCTGTCTATGGCTACTCCATCACCAGCGGCTATT

TCTGGAACTGGATCCGCCAGCCCCCAGGGAAGGGGCTGGAGTGGATTGGG

TACATCAGCTACGACGGCAGCAGCAACTCCAACCCATCTCTCAAAAATAG

GGTCACAATCAGCAGAGACACCTCCAAGAACCAGTTCTCCCTGAAGCTGA

GCTCTGTGACCGCCGCCGACACCGCTGTGTATTACTGTGCCAGAGGAACT

ACCGGGTTTGCTTACTGGGGCCAAGGGACCCTGGTCACCGTCTCCTCAGC

CTCCACCAAGGGCCCATCGGTCTTCCCCCTGGCACCCTCCTCCAAGAGCA

CCTCTGGGGGCACAGCGGCCCTGGGCTGCCTGGTCAAGGACTACTTCCCC

GAACCGGTGACGGTGTCGTGGAACTCAGGCGCCCTGACCAGCGGCGTGCA

CACCTTCCCGGCTGTCCTACAGTCCTCAGGACTCTACTCCCTCAGCAGCG

TCGTGACCGTGCCCTCCAGCAGCTTGGGCACCCAGACCTACATCTGCAAC

GTGAATCACAAGCCCAGCAACACCAAGGTGGACAAGAAAGTT<u>ACATCAAC</u>

<u>TACAAATGACACTGATAAAGTAGATTATGAAGAATACTCCACAGAGTTGA</u>

<u>TTGTAAATACAGATAGTGAATCGACTATAGACATAATACTATCTGGATCT</u>

<u>ACACATTCACCGGAAACTAGTTCTAAGAAACCTGATTATATAGATAATTC</u>

<u>TAATTGCTCGTCGGTATTCGAAATCGCGACTCCGGAACCAATTACTGATA</u>

<u>ATGTAGAAGATCATACAGACACCGTCACATACACTAGTGATAGCATTAAT</u>

<u>ACAGTAAGTGCATCATCTGGAGAATCCACAACAGACGAGACTCCGGAACC</u>

<u>AATTACTGATAAAGAAGATCATACAGTTACAGACACTGTCTCATACACTA</u>

<u>CAGTAAGTACATCATCTGGAATTGTCACTACTAAATCAACCACCGATGAT</u>

<u>GCGGATCTTTATGATACGTACAATGATAATGATACAGTACCACCAACTAC</u>

<u>TGTAGGCGGTAGTACAACCTCTATTAGCAATTATAAAACCAAGGACTTTG</u>

<u>TAGAAATATTTGGTATTACCGCATTAATTATATTGTCGGCCGTGGCAATT</u>

<u>TTCTGTATTACATATTATATATATAATAAACGTTCACGTAAATACAAAAC</u>

<u>AGAGAACAAAGTCTAG</u>

The nucleotide sequence encoding the VH (H2124) and CH1 domain is underlined, and the nucleotide sequence encoding the A56R domain is double underlined.

Amino Acid Sequence of VH (H2124)-CH1-A56R Fab Product Fusion Protein (SEQ ID NO:11):

QVQLQQWGAGLLKPSETLSLTCAVYGYSITSGYFWNWIRQPPGKGLEWIG
YISYDGSSNSNPSLKNRVTISRDTSKNQFSLKLSSVTAADTAVYYCARGT
TGFAYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKV<u>TSTTNDTDKVDYEEYSTELIVNTDSESTIDIILSGS
THSPETSSKKPDYIDNSNCSSVFEIATPEPITDNVEDHTDTVTYTSDSIN
TVSASSGESTTDETPEPITDKEDHTVTDTVSYTTVSTSSGIVTTKSTTDD
ADLYDTYNDNDTVPPTTVGGSTTSISNYKTKDFVEIFGITALIILSAVAI
FCITYYIYNKRSRKYKTENKV</u>.

The amino acid sequence for the VH (H2124) and CH1 domain is underlined, and the amino acid sequence for the A56R domain is double underlined.

Polynucleotide Sequence Encoding VH (H2124)-IgG-A56R TR Construct Fusion Protein (SEQ ID NO:27):

CAGGTGCAGCTGCAGCAGTGGGGCGCAGGACTGCTGAAGCCTAGCGAGAC
CCTGTCCCTCACCTGCGCTGTCTATGGCTACTCCATCACCAGCGGCTATT
TCTGGAACTGGATCCGCCAGCCCCCAGGGAAGGGGCTGGAGTGGATTGGG
TACATCAGCTACGACGGCAGCAGCAACTCCAACCCATCTCTCAAAAATAG
GGTCACAATCAGCAGAGACACCTCCAAGAACCAGTTCTCCCTGAAGCTGA
GCTCTGTGACCGCCGCCGACACCGCTGTGTATTACTGTGCCAGAGGAACT
ACCGGGTTTGCTTACTGGGGCCAAGGGACCCTGGTCACCGTCTCCTCAGC
CTCCACCAAGGGCCCATCGGTCTTCCCCCTGGCACCCTCCTCCAAGAGCA
CCTCTGGGGGCACAGCGGCCCTGGGCTGCCTGGTCAAGGACTACTTCCCC
GAACCGGTGACGGTGTCGTGGAACTCAGGCGCCCTGACCAGCGGCGTGCA
CACCTTCCCGGCTGTCCTACAGTCCTCAGGACTCTACTCCCTCAGCAGCG
TCGTGACCGTGCCCTCCAGCAGCTTGGGCACCCAGACCTACATCTGCAAC
GTGAATCACAAGCCCAGCAACACCAAGGTGGACAAGAAAGTTGAGCCCAA
ATCTTGTGACAAAACTCACACATGCCCACCGTGCCCAGCACCTGAACTCC
TGGGGGGACCGTCAGTCTTCCTCTTCCCCCCAAAACCCAAGGACACCCTC
ATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGC
ATAATGCCAAGACAAAGCCGCGGGAGGAGCAGTACAACAGCACGTACCGT
GTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAA
CCATCTCCAAAGCCAAAGGGCAGCCCCGAGAACCACAGGTGTACACCCTG
CCCCCATCCCGGGATGAGCTGACCAAGAACCAGGTCAGCCTGACCTGCCT
GGTCAAAGGCTTCTATCCCAGCGACATCGCCGTGGAGTGGGAGAGCAATG
GGCAGCCGGAGAACAACTACAAGACCACGCCTCCCGTGCTGGACTCCGAC
GGCTCCTTCTTCCTCTACAGCAAGCTCACCGTGGACAAGAGCAGGTGGCA
GCAGGGGAACGTCTTCTCATGCTCCGTGATGCATGAGGCTCTGCACAACC

ACTACACGCAGAAGAGCCTCTCCCTGTCTCCGGGTAAA<u>ACCACCGATGAT
GCGGATCTTTATGATACGTACAATGATAATGATACAGTACCACCAACTAC
TGTAGGCGGTAGTACAACCTCTATTAGCAATTATAAAACCAAGGACTTTG
TAGAAATATTTGGTATTACCGCATTAATTATATTGTCGGCCGTGGCAATT
TTCTGTATTACATATTATATATATAATAAACGTTCACGTAAATACAAAAC
AGAGAACAAAGTCTAG</u>

The nucleotide sequence encoding the VH (H2124) and full length Ig domain is underlined, and the nucleotide sequence encoding the shorter form A56R domain is double underlined.

Amino Acid Sequence of VH (H2124)-IgG-A56R TR Construct Fusion Protein (SEQ ID NO:28):

<u>QVQLQQWGAGLLKPSETLSLTCAVYGYSITSGYFWNWIRQPPGKGLEWIG
YISYDGSSNSNPSLKNRVTISRDTSKNQFSLKLSSVTAADTAVYYCARGT
TGFAYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK</u><u>TTDD
ADLYDTYNDNDTVPPTTVGGSTTSISNYKTKDFVEIFGITALIILSAVAI
FCITYYIYNKRSRKYKTENKV</u>.

The amino acid sequence for the VH (H2124) and full length Ig domain is underlined, and the amino acid sequence for the shorter form A56R domain is double underlined.

Polynucleotide Sequence Encoding VH (H2124)-IgG-A56R FL Construct Fusion Protein (SEQ ID NO:29):

CAGGTGCAGCTGCAGCAGTGGGGCGCAGGACTGCTGAAGCCTAGCGAGAC
CCTGTCCCTCACCTGCGCTGTCTATGGCTACTCCATCACCAGCGGCTATT
TCTGGAACTGGATCCGCCAGCCCCCAGGGAAGGGGCTGGAGTGGATTGGG
TACATCAGCTACGACGGCAGCAGCAACTCCAACCCATCTCTCAAAAATAG
GGTCACAATCAGCAGAGACACCTCCAAGAACCAGTTCTCCCTGAAGCTGA
GCTCTGTGACCGCCGCCGACACCGCTGTGTATTACTGTGCCAGAGGAACT
ACCGGGTTTGCTTACTGGGGCCAAGGGACCCTGGTCACCGTCTCCTCAGC
CTCCACCAAGGGCCCATCGGTCTTCCCCCTGGCACCCTCCTCCAAGAGCA
CCTCTGGGGGCACAGCGGCCCTGGGCTGCCTGGTCAAGGACTACTTCCCC
GAACCGGTGACGGTGTCGTGGAACTCAGGCGCCCTGACCAGCGGCGTGCA
CACCTTCCCGGCTGTCCTACAGTCCTCAGGACTCTACTCCCTCAGCAGCG
TCGTGACCGTGCCCTCCAGCAGCTTGGGCACCCAGACCTACATCTGCAAC
GTGAATCACAAGCCCAGCAACACCAAGGTGGACAAGAAAGTTGAGCCCAA
ATCTTGTGACAAAACTCACACATGCCCACCGTGCCCAGCACCTGAACTCC

-continued
```
TGGGGGGACCGTCAGTCTTCCTCTTCCCCCCAAAACCCAAGGACACCCTC

ATGATCTCCCGGACCCCTGAGGTCACATGCGTGGTGGTGGACGTGAGCCA

CGAAGACCCTGAGGTCAAGTTCAACTGGTACGTGGACGGCGTGGAGGTGC

ATAATGCCAAGACAAAGCCGCGGGAGGAGCAGTACAACAGCACGTACCGT

GTGGTCAGCGTCCTCACCGTCCTGCACCAGGACTGGCTGAATGGCAAGGA

GTACAAGTGCAAGGTCTCCAACAAAGCCCTCCCAGCCCCCATCGAGAAAA

CCATCTCCAAAGCCAAAGGGCAGCCCCGAGAACCACAGGTGTACACCCTG

CCCCCATCCCGGGATGAGCTGACCAAGAACCAGGTCAGCCTGACCTGCCT

GGTCAAAGGCTTCTATCCCAGCGACATCGCCGTGGAGTGGGAGAGCAATG

GGCAGCCGGAGAACAACTACAAGACCACGCCTCCCGTGCTGGACTCCGAC

GGCTCCTTCTTCCTCTACAGCAAGCTCACCGTGGACAAGAGCAGGTGGCA

GCAGGGGAACGTCTTCTCATGCTCCGTGATGCATGAGGCTCTGCACAACC

ACTACACGCAGAAGAGCCTCTCCCTGTCTCCGGGTAAAACATCAACTACA

AATGACACTGATAAAGTAGATTATGAAGAATACTCCACAGAGTTGATTGT

AAATACAGATAGTGAATCGACTATAGACATAATACTATCTGGATCTACAC

ATTCACCGGAAACTAGTTCTAAGAAACCTGATTATATAGATAATTCTAAT

TGCTCGTCGGTATTCGAAATCGCGACTCCGGAACCAATTACTGATAATGT

AGAAGATCATACAGACACCGTCACATACACTAGTGATAGCATTAATACAG

TAAGTGCATCATCTGGAGAATCCACAACAGACGAGACTCCGGAACCAATT

ACTGATAAAGAAGATCATACAGTTACAGACACTGTCTCATACACTACAGT

AAGTACATCATCTGGAATTGTCACTACTAAATCAACCACCGATGATGCGG

ATCTTTATGATACGTACAATGATAATGATACAGTACCACCAACTACTGTA

GGCGGTAGTACAACCTCTATTAGCAATTATAAAACCAAGGACTTTGTAGA

AATATTTGGTATTACCGCATTAATTATATTGTCGGCCGTGGCAATTTTCT

GTATTACATATTATATATATAATAAACGTTCACGTAAATACAAAACAGAG

AACAAAGTCTAG.
```

The nucleotide sequence encoding the VH (H2124) and full length Ig domain is underlined, and the nucleotide sequence encoding the longer form A56R domain is double underlined.

Amino Acid Sequence of VH (H2124)-IgG-A56R FL Construct Fusion Protein (SEQ ID NO:30):

```
QVQLQQWGAGLLKPSETLSLTCAVYGYSITSGYFWNWIRQPPGKGLEWIG

YISYDGSSNSNPSLKNRVTISRDTSKNQFSLKLSSVTAADTAVYYCARGT

TGFAYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGKTSTT

NDTDKVDYEEYSTELIVNTDSESTIDIILSGSTHSPETSSKKPDYIDNSN

CSSVFEIATPEPITDNVEDHTDTVTYTSDSINTVSASSGESTTDETPEPI

TDKEDHTVTDTVSYTTVSTSSGIVTTKSTTDDADLYDTYNDNDTVPPTTV

GGSTTSISNYKTKDFVEIFGITALIILSAVAIFCITYYIYNKRSRKYKTE

NKV
```

The amino acid sequence for the VH (H2124) and full length Ig domain is underlined, and the amino acid sequence for the longer form A56R domain is double underlined.

Example 2: Expression of A56R Fusion Protein on Surface of Hela Cells

HeLa cells were infected or co-infected with recombinant EEV vaccinia virus expressing immunoglobulin fusion constructs, Variable Heavy (H2124) CH1-A56R (described in the Example above) and Ig-K ("A56R H+L") or scFv-A56R ("A56R scFv"). An illustration of the general strategy for infection of cells with recombinant EEV vaccinia virus and the subsequent library selection steps is shown in FIG. 2. In the current example, instead of using libraries, the HeLa cells were co-infected with recombinant vaccinia virus expressing the VH (H2124) CH1-A56R Fusion and recombinant vaccinia virus expressing the Ig-K (A56R H+L) or infected with recombinant vaccinia virus expressing scFv-A56R. Fluorescence Activated Cell Sorting (FACS) analysis for C35 staining and CD100 staining of cells infected with EEV recombinant vaccinia virus was performed. Briefly, 1 µg/ml CD100-His or 1 µg/ml C35-His were added to the samples and incubated for 30 minutes on ice. The cells were then washed and anti-his APC was added and the samples were incubated for 30 minutes on ice, and then the samples were washed, fixed and analyzed. The FACS data is shown in FIG. 3A-C. These results show that the A56R fusion proteins, were expressed on the cell surface.

The clones in EEV format were also tested by ELISA. Purified C35 protein was coated on a 96-well ELISA plate (Nunc-MaxiSorp 96 well flat bottom immune plate Cat #439454) at 1 µg/mL in carbonate buffer. The plate was washed and then blocked with 1×PBS, 10% FBS. Psoralen-inactivated EEV was then added to the plate, diluted in 1×PBS/10% FBS/0.05% Tween-20, into designated wells and allowed to bind. Viral particles were detected using Rabbit anti-Vaccinia-HRP conjugated antibody (AbCam Catalog #28250), the antibody was diluted 1:2000 in 1×PBS/10% FBS/0.05% Tween-20. TMB substrate (to detect horseradish peroxidase (HRP) activity) was then added to the plate; color was allowed to develop and then the reaction was terminated with an equal volume of 2N $H_2SO_4$. The plate was read on an ELISA plate reader and the results are shown in FIG. 4A. A second ELISA was used to confirm binding by detecting FAb, using the same conditions as above, except the secondary antibody was Goat anti-human IgG F(ab')$_2$-HRP conjugated (Jackson ImmunoResearch catalog #109-036-097) used at a 1:10,000 dilution of the stock antibody, with 1×PBS/10% FBS/0.05% Tween-20 as dilution buffer. Results are shown in FIG. 4B. Wells that were positive on both plates showed that the antibody construct was expressed in the presence of the vaccinia viral virion. As shown in FIG. 3A-B, EEV containing the C35 specific fusion protein (labeled "A56R EEV") bound to C35, while a control ("L517+G7000-A56R EEV"), non-C35 binding EEV, did not bind, and C35 specific antibody in standard membrane bound IgG1 format ("mbg EEV") also did not bind. The data demonstrated antigen specific binding of EEV when the antibody was expressed with A56R.

Example 3: Plate Based and Solution Based Fusion Protein Selection

Recombinant vaccinia virus expressing A56R fusions with known C35 and VEGF binding molecules were tested for binding to target molecules using a panning based assay. Recombinant EEV expressing immunoglobulin molecules known to be specific for C35 (scFv2408-A56R, H2124-L517-A56R double gene, and L517+H2124-A56R co-infection) or VEGF (L7000+H7000-A56R) were produced in BSC1 cells (for about 24 hours). H2124-L517-A56R double gene produced the same antibody as L517+H2124-A56R, except the Ig-H and Ig-K genes were encoded by the same virus from the double gene and the Ig-H and Ig-K genes were encoded by separate viruses used for the H2124-A56R co-infection.

The clones in EEV format were tested by plaque assay. Sterile 96-well ELISA plates were coated with 1 µg/ml C35 or 1 µg/ml VEGF). EEV containing supernatant "Neat" (undiluted) was diluted by serial dilution generating 1:10 to 1:$10^6$ dilutions. 100 µl of the various virus constructs was added to designated wells and binding was allowed to proceed for 2 hours or overnight at room temperature. The cells were washed 10 times with PBS to remove unbound EEV and then approximately 25,000 BSC1 cells were added to each well, and the plates were incubated at 37° C. overnight. Plaque formation was detected by staining the wells with crystal violet. FIGS. 5A-D show the plaque assay plate results for C35 binding after 2 hours and overnight, and VEGF binding after 2 hours and overnight, respectively. These results showed that the A56R fusion proteins were expressed at the surface of the vaccinia virions. Furthermore, the results showed that known binding segments produced using A56R fusions expressed on EEV were able to bind to their specific targets.

Next, bead-based selection was performed using Streptavidin beads, Protein G beads or tosyl activated beads.

Streptavidin (SAV) Bead Selection.

Magnetic bead-based selection was tested using recombinant EEV expressing MAb 2408 (H2124-A56R+L517 (C35-specific)) or MAb 7000 (H7000-A56R+L7000 (VEGF-specific)). Hela cells were infected with the various virus constructs in two T175 flasks for 2 days, supernatant was collected, and cells were pelleted. The EEV was pelleted by spinning for 1 hour in a SA-600 rotor at 15,000 RPM. The EEV pellet was resuspended in 1 ml DMEM supplemented with 10% FBS. For each recombinant virus, 500 µl supernatant (~$10^7$ pfu) was used. Next, 500 µl DMEM containing 1 µg biotin-C35 was added to each sample (resulting in a solution of 1 ml volume at 1 µg/ml concentration). The solution was incubated in a cold room on a rotator for 2 hours. 200 µl M280 Streptavidin (SAV) magnetic beads were added to the EEV/C35 solution (the SAV bead concentration was high enough to bind all of the biotin-C35 so no washing step was required). The solution was rotated at room temp for 20 minutes to allow the beads to bind to the biotin-C35. Virus constructs prepared as described above were added to the beads. The beads were collected using a magnet, and the unbound virus was collected separately. The beads were washed 5× with 1 ml PBS. All of the washes with the unbound virus were pooled ("Unbound"). The beads were removed from the magnet. 1 ml of DMEM supplemented with 2.5% FBS was added and the solution was transferred to a fresh tube ("Bound").

"Unbound" and "Bound" were titered. The results are shown in Table 1. These results show that EEV expressing the 2408 antibody, C35-specific, bound to the beads while the EEV expressing the 7000 antibody, VEGF-specific, did not bind.

TABLE 1

Selection of C35-specific mAb using Biotin-C35 and SAV magnetic beads

| Virus | Titer | % Bound |
|---|---|---|
| MAb 7000 Unbound | 1.45 × $10^7$ | |
| MAb 7000 Bound | 1.2 × $10^4$ | 0.1% |
| MAb 2408 Unbound | 7.6 × $10^6$ | |
| MAb 2408 Bound | 7.7 × $10^6$ | 50% |

Spiking experiments were performed where EEV expressing L517 was set at moi=1, and co-infected into Hela with a mix where EEV expressing H2124-A56R was diluted to 1:$10^4$ and 1:$10^5$ with H7000-A56R (one T175 Hela per spiking condition). In short, EEV was harvested, and 500 µl EEV containing supernatant (5×$10^6$ pfu) was used for each spike. 500 µl DMEM containing 1 µg Biotin-hC35 was added to each sample (1 ml volume @ 1 ug/ml concentration). The Bound and Unbound solutions were collected using the SAV-bead (M280) selection method described above. Bound virus was amplified on BSC1 in T75 flasks.

The collected Bound and Unbound samples for each spiking experiment were tested for enrichment by flow cytometry. The results from the spiking experiments showed a clear enrichment with beads $10^{-4}$ and $10^{-5}$ and that bead selection was more efficient than the plate selection method (data not shown).

Different beads were also tested, Protein G beads (Dynal) and tosylactivated beads (Dynal) using methods similar to those described above for SAV beads. The following previously identified antibodies were used during the selection assays: MAb 2408 (C35-specific antibody, a humanized 1F2 antibody comprising H2124+L517), MAb 2368 (CD100-specific antibody, disclosed in U.S. Appl. No. 2010/0285036), mAb 7000 (VEGF-specific parent antibody of bevacizumab), and mAb 8000 (Her2-specific parent antibody of trastuzumab).

Protein G Bead Selection.

EEV produced in small scale infections of Hela cells in 6 well plates (titer ~5×$10^5$/ml) were used. Protein G bead selection was tested using EEV expressing 2368-A56R (H2090-A56R+L512, both VH and VL expressed in vaccinia): 1 ml virus (~5×$10^5$ pfu) and EEV expressing 2408-A56R (H2124-A56R+L517, both VH and VL expressed in vaccinia): 1 ml virus (5×$10^5$ pfu)). CD100 bound to Protein G beads was prepared as follows: 300 µl magnetic Protein G beads (2× standard amount/sample) were used and pull down was performed with a magnet. 600 µl PBS+18 µl CD100-Fc (=36 µg) was added to the beads, which were incubated at room temp for 20 minutes (on rotator) to allow CD100-Fc to bind to Protein G beads. Beads were pulled down with a magnet and washed 1× with 1 ml PBS. Next, the beads were resuspended in 300 µl DMEM supplemented with 10%. 100 µl CD100-Fc/Pro G beads were added to each virus sample (~2× the standard amount of Pro-G beads), which was about 12 µg/ml CD100-Fc. The solution was incubated for 2 hours at room temperature. 550 µl (about 50%) of the beads were removed and unbound was collected following standard 5×1 ml PBS washes. Beads were removed from the magnet, 1 ml DMEM supplemented with 2.5% was added, and the solution was transferred to a fresh tube ("Bound"). "Unbound" and "Bound" were titered. The remaining 550 µl was allowed to continue incubating at room temp for another 1.5 hours (3.5 hours total) and then for 18 hours at 4 degrees before being harvested as described above.

Tosylactivated Bead Selection.

EEV expressing the same 2408 (C35-specific) and 2368 (CD100-specific) antibodies used in the Protein G bead selection experiments above were used for the tosylactivated magnetic bead selection. 100 µg C35-His was conjugated to tosylactivated magnetic beads in PBS or ELISA coating buffer (CB). The solution was incubated at 37 degrees overnight, and blocked for 1 hour at 37 with PBS, 10% FBS, 0.5% BSA. The beads were washed 1×, resuspended in 160 µl DMEM supplemented with 10%. 50 µl of each bead sample was added to each virus sample and incubated at room temp for 5 hours. Unbound was collected following standard 5×1 ml PBS washes. Beads were removed from the magnet, 1 ml DMEM supplemented with 2.5% was added, and the beads were transferred to fresh tube ("Bound"). "Unbound" and "Bound" were titered.

100 µg CD100-His was conjugated to tosylactivated magnetic beads in PBS for the CD100 antibody selection assay with 2368-A56R (1 ml virus (5×10^5 pfu)) and 2408-A56R (1 ml virus (5×10^5 pfu)) using the same methods described above for the C35 antibody selection assay.

The results using the Protein G bead selection are shown in in Table 2 and the results using tosylactivated bead selection are shown in Tables 3 and 4.

TABLE 2

Selection of CD100-specific mAb using CD100-Fc and Protein G beads

| Virus/Binding time | Sample | Titer | % Bound |
|---|---|---|---|
| MAb 2408 - 2 hours | Unbound | 100,000 | |
| MAb 2408 - 2 hours | Bound | 360 | 0.36% |
| MAb 2368 - 2 hours | Unbound | 64,000 | |
| MAb 2368 - 2 hours | Bound | 88,000 | 58% |
| MAb 2368 - overnight | Unbound | 130,000 | |
| MAb 2368 - overnight | Bound | 90,000 | 41% |
| MAb 2408 - overnight | Unbound | 320,000 | |
| MAb 2408 - overnight | Bound | 160 | 0.05% |

TABLE 3

Selection of C35-specific mAb using C35 Tosylactivated beads

| Virus | Sample | Titer | % Bound |
|---|---|---|---|
| MAb 2408 | Unbound | 96,000 | |
| MAb 2408 | Bound | 160,000 | 61% |
| MAb 2368 | Unbound | 240,000 | |
| MAb 2368 | Bound | 1,600 | 0.6% |
| MAb 2408 | Unbound | 97,000 | |
| MAb 2408 | Bound | 140,000 | 59% |

TABLE 4

Selection of CD100-specific mAb using CD100-His Tosylactivated beads

| Virus | Sample | Titer | % Bound |
|---|---|---|---|
| MAb 2408 | Unbound | 384,000 | |
| MAb 2408 | Bound | 480 | 0.1% |
| MAb 2368 | Unbound | 264,000 | |
| MAb 2368 | Bound | 232,000 | 46.7% |

Example 4: CH1-A56R Fusion Protein Library Creation

A library of polynucleotides encoding immunoglobulin segments was produced as follows. A recombinant vaccinia library referred to as "naïve heavy, A56R fusion" was created using bone marrow RNA that was purchased from a commercial supplier (Life Technologies) representing more than 100 donors. Reverse transcription was performed using antisense primers specific for the constant region of either human immunoglobulin gamma or mu. The resulting cDNA was used as template for PCR with one of two sense primers that bound to the beginning of human variable heavy framework region 1 and introduced a BssHII restriction site in combination with a pool of antisense primers that bound to the various germline human J segments and introduced a BstEII restriction site. The sequences of these primers were as follows:

```
Sense VH 3:
                                    (SEQ ID NO: 12)
AATATGCGCGCACTCCGAGGTGCAGCTGGTGGAGTCTGG Sense VH 3a:
                                    (SEQ ID NO: 13)
AATATGCGCGCACTCCGAGGTGCAGCTGTTGGAGTCTGG Antisense JH 1:
                                    (SEQ ID NO: 14)
GAGACGGTGACCAGGGTGCCCTGGCCCCA Antisense JH 2:
                                    (SEQ ID NO: 15)
GAGACGGTGACCAGGGTGCCACGGCCCCA Antisense JH 3:
                                    (SEQ ID NO: 16)
GAGACGGTGACCATTGTCCCTTGGCCCCA Antisense JH 4/5:
                                    (SEQ ID NO: 17)
GAGACGGTGACCAGGGTTCCCTGGCCCCA Antisense JH 6:
                                    (SEQ ID NO: 18)
GAGACGGTGACCGTGGTCCCTTGGCCCCA
```

The resulting PCR products were cloned into the pJEM1 plasmid disclosed above for the purpose of creating recombinant vaccinia virus. In particular, the human immunoglobulin variable heavy expression cassette described herein was cloned in frame with human immunoglobulin constant domain region CH1 and vaccinia virus integral membrane protein A56R cDNA. The resulting proteins created from expression of the library were fusion proteins containing an immunoglobulin heavy chain variable segment, the heavy chain CH1, and a portion of the A56R protein expressed on the surface of vaccinia EEV.

The naïve heavy, A56R fusion library was used along with vaccinia expressing known Ig-L or a vaccinia virus expressed Ig-L library (as previously disclosed in U.S. Pat. No. 7,858,559, which is incorporated herein by reference in its entirety) for vaccinia panning as illustrated in FIG. 2.

Example 5: CH1-A56R Fusion Protein Library Screening for CD100 Antibody Selection Selection for new CD100 antibodies using the ~1,200,000 clones from the naïve heavy, A56R fusion library (also referred to as "library 3") described in the previous Example+light chain clones (L48, L116 and L9021) was performed.

T-175 Hela cells were infected with EEV expressing the fusion library+Light chains described above for 2 days after which the supernatant was harvested, pelleted with low speed spins 2×, and the EEV pelleted at 15,000 RPM for 1 hour. EEV was resuspended in 3 ml DMEM supplemented with 10% FBS.

Round 1 Selection. EEV expressing 2368-A56R (1 ml virus (~5×10^5 pfu)) and EEV expressing 2408-A56R (1 ml virus (5×10^5 pfu)) were used as controls and library 3 (1 ml virus (~10^8 pfu)) was used for the selection assay. First, 300 µl Protein G beads (2× standard amount/sample) were pulled down with a magnet, and 600 µl PBS+18 µl CD100-Fc (=36 µg) was added to the beads. The solution was incubated at room temp for 20 minutes (on rotator) to allow CD100-Fc to bind to Protein G beads. Beads were pulled down with magnet, washed 1× with 1 ml PBS, and resuspended in 300 µl DMEM supplemented with 10%.

Next, 100 µl of the CD100-Fc/Pro G per sample (about 12 µg/ml CD100-Fc) was added to the EEV (2408 and 2368 controls, and library 3) and incubated for 2 hours at room temperature. 550 µl (about 50%) of the beads were removed and unbound virus was collected following standard 5×1 ml PBS washes. Beads were removed from the magnet and 1 ml DMEM supplemented with 2.5% was added, and the solution was transferred to a fresh tube ("Bound"). "Unbound" and "Bound" were titered. These "2 hour incubation" samples were titered with methyl cellulose added after 45 minutes. Beads recovered from the bound library were amplified on BSC1 in T75 (This Round 1 2 hour selection was termed "CD100 3.1A"). The other 550 µl (about 50%) of the beads was allowed to continue incubating at room temp for another 1.5 hours (3.5 hours total) and then for 18 hours at 4° C. degrees ("overnight"). The unbound virus was collected following standard 5×1 ml PBS washes. Beads were removed from the magnet, 1 ml DMEM supplemented with 2.5% was added and the solution was transferred to a fresh tube ("Bound"). "Unbound" and "Bound" were titered. Bound library was amplified on BSC1 in T75 (This Round 1 overnight selection was termed "CD100 3.1B"). The results are shown in Table 5.

TABLE 5

Round 1 Selection of CD100 Ab

| Virus/Binding time | Sample | Titer | % Bound |
|---|---|---|---|
| 2408-2 hours | Unbound | 100,000 | |
| 2408-2 hours | Bound | 360 | 0.36% |
| 2368-2 hours | Unbound | 64,000 | |
| 2368-2 hours | Bound | 88,000 | 58% |
| Library 3.1A-2 hours | Unbound | 22,000,000 | |
| Library 3.1A-2 hours | Bound | 20,000 | ~0.1% |
| 2408-Overnight | Unbound | 130,000 | |
| 2408-Overnight | Bound | 90,000 | 41% |
| 2368-Overnight | Unbound | 320,000 | |
| 2368-Overnight | Bound | 160 | 0.05% |
| Library 3.1B-Overnight | Unbound | 56,000,000 | |
| Library 3.1B-Overnight | Bound | 17,000 | 0.03% |

Library 3.1A and 3.1B gave good amplification on BSC1, harvest and titer (~2×10^7/ml each).

Round 2 Selection. EEV produced in small scale infections of Hela in 6 well plates (titer ~5×10^5/ml) were used. Library 3.1A and 3.1B were pooled together into one sample. EEV expressing 2368-A56R (1 ml virus (~5×10^5 pfu)), EEV expressing 2408-A56R (1 ml virus (5×10^5 pfu)) and 3.1A/B library (1 ml virus (~5×10^5 pfu)) were each combined with 300 µl Protein G beads (2× standard amount/sample). 600 µl PBS+18 µl CD100-Fc (=36 µg) was added to the beads. The solution was incubated at room temp for 20 minutes (on rotator) to allow CD100-Fc to bind to Protein G beads. The beads were washed and resuspended as described above for Round 1. 100 µl CD100-Fc/Pro G per sample (~12 µg/ml CD100-Fc) was added to the virus samples and incubated for 4.5 hours at room temperature. The "Unbound" and "Bound" were collected and titered. Bound library was amplified on BSC1 in T75 (Round 2 selection was termed "CD100 3.2"). The results of the Round 2 selection are shown in Table 6.

TABLE 6

Round 2 Selection for CD100 Ab

| Virus-Antigen | Sample | Titer | % Bound |
|---|---|---|---|
| 2408-CD100-Fc | Unbound | 384,000 | |
| 2408- CD100-Fc | Bound | 780 | 0.2% |
| 2368- CD100-Fc | Unbound | 264,000 | |
| 2368- CD100-Fc | Bound | 224,000 | 46% |
| Library 3.2-CD100-Fc | Unbound | 780,000 | |
| Library 3.2-CD100-Fc | Bound | 5,000 | 0.6% |

Library 3.2 gave good amplification on BSC1, harvest and titer (~3×10^7/ml), and resulted in a small population of positive cells. A third round of selection was performed.

Round 3 Selection. A third round of selection was performed using the same methods described above using "library 3.2A" (Rounds 1 and 2=CD100-Fc/Pro G). Bound library was amplified on BSC1 in T75 (Round 3 selection was termed "CD100 3.3A"). The results of the Round 3A selection were tested by flow cytometry. A second Round 3 selection was performed with 100 µg CD100-His conjugated to tosylactivated magnetic beads in PBS using the methods disclosed above. 50 µl per sample was added for selection using the same lot of virus that was used for CD100 3.3A (2368-A56R (1 ml virus (~5×10^5 pfu)), 2408-A56R (1 ml virus (5×10^5 pfu)) and 3.2A (1 ml virus (~5×10^5 pfu)). The solutions were incubated at room temperature for 4 hours. The "Unbound" and "Bound" were collected and titered. Bound library was amplified on BSC1 in T75 (Round 3 tosylactivated selection was termed "CD100 3.3B"). The results of the round 3B selection were tested by flow cytometry. A diagram summarizing the CD100 antibody selection strategy is illustrated in FIG. 6.

Flow cytometry staining suggested that there was probably a positive population in CD100 3.3A/B when paired with L116. Plaques from 3.3A (n=27) and 3.3B (n=30) were picked and amplified for 3 days on BSC1 in 24-well plate (1 plaque per well). Hela cells were infected in 24-well plates with ⅓ of each amplified plaque. The cells were co-infected with L116 at moi=1 (controls: 2368, 2408 and uninfected Hela supernatant). EEV was produced for 2 days, harvested, and inactivated with psoralen and irradiation with long-wave UV light (PLWUV). The virus was bound to CD100 (2 µg/ml) and C35 (2 µg/ml) coated plates O/N using 50 µl EEV+50 µL ELISA blocking buffer per well.

Antibody binding was detected by adding anti-Fab-HRP. Two clones (3.3.C20 and 3.3C27) had good binding to CD100 and were sequenced. These clones were further characterized by flow cytometry for specificity and affinity. The clones were amplified on BSC1 in T75, and titered. The 3.3A/B (with L116) infected cells were CD100 sorted. The virus from sorted cells (150 cells) was amplified, titered and tested by flow (100 µg/ml CD100-His: 30 minutes on ice, washed with 5 ml, followed by anti-HIS-APC+anti-Fab-FITC: 30 minutes on ice). Both Clones 20 and 27 bound to CD100 as determined by flow cytometry.

The sequences for two high affinity CD100 VH clones (3.3.C20 and 3.3C27) when paired with L116 were identical. The sequence alignment of the two clones is shown in FIG. 7. The amino acid sequence for the variable heavy chain is as follows (VH CDR1-3 are underlined):

(SEQ ID NO: 19)
EVQLVESGGGLVKPGGSLRLSCAASG<u>FIFTDYYLS</u>WIRQAPGKGPEWLS<u>Y</u>

<u>ISSYSRYTNYADSVKG</u>RFTISRDNTRNSIYLQMNNLRVEDTAVYYCAR<u>AG</u>

<u>SYYGY</u>WGQGTLVT.

Example 6: CH1-A56R Fusion Protein Library Screening for Her2 Antibody Selection Selection for new Her2 antibodies using 1,200,000 clones from the naïve heavy, A56R fusion library (also referred to as "library 3")+light chain clones (L48, L116 and L9021) was performed. The library is the same that was used for the CD100 selections discussed above.

Round 1 Selection. Library 3 (1 ml virus (~10^8 pfu)) was used for this selection. First, 100 µl PBS+100 µl Her2-Fc (R&D Systems) (=10 µg) was added to the Protein G beads. The solution was incubated at room temp for 25 minutes (on rotator) to allow Her2-Fc to bind to Protein G beads. Beads were pulled down with magnet, washed 1× with 1 ml PBS, and resuspended in 100 µl DMEM supplemented with 10%.

Next, 100 µl Her2-Fc/Pro G (~10 µg/ml Her2-Fc) was added to 1 ml of Library 3 and incubated for 4 hours at room temperature. Beads were removed and unbound virus was collected following standard 5×1 ml PBS washes. Beads were removed from the magnet and 1 ml DMEM supplemented with 2.5% was added, and the solution was transferred to fresh tube ("Bound"). "Unbound" and "Bound" were titered. Beads recovered from the bound library were amplified on BSC1 in T75 (Round 1 selection was termed "Her2.3.1").

Round 2 Selection. Amplified Her2.3.1 was titered and amplified in 6 well plate format (co-infected with L48, L116 and L9021) and an additional cycle of Her2-Fc/ProG selection was performed using the methods described above. Bound library was amplified on BSC1 in T75 (Round 2 selection was termed "Her2.3.2").

Round 3 Selection. Amplified Her2.3.2 was titered and reamplified in 6 well plate format (co-infected with L48, L116 and L9021) and an additional cycle of Her2-Fc/ProG selection was performed using the methods described above. Bound library was amplified on BSC1 in T75 (Round 3 selection was termed "Her2.3.3"). The results of the Her2.3.2 and Her2.3.3 selection were tested by flow cytometry. In this experiment, 3 µg/ml C35-His or 10 µg/ml Her2-His were incubated with anti-His-APC MAB for 30 minutes on ice to form complexes. Anti-Fab-FITC as then added and the Antigen-anti-His complexes were added to the cells for 30 minutes on ice. The cells were then washed with 2 ml PBS, 0.5% BSA, 2 nM EDTA. Anti-his-APC and anti-Fab-FITC were then added for 30 minutes on ice, the cells were then washed, fixed, and flow cytometry assay was run. As shown in FIG. 8, all three light chains enriched for Her2 specific antibodies.

Round 4 Selection. Hela cells in 6 well plate format were co-infected with Her2.3.3 and L116 only, EEV was isolated as described above and an additional cycle of Her2-Fc/ProG selection was performed using the methods described above. Bound library was amplified on BSC1 in T75 (Round 4 selection was termed "Her2.3.4"). A diagram summarizing the Her2 antibody selection strategy is illustrated in FIG. 9.

The results of the Her2.3.3 and Her2.3.4 selection were tested by flow cytometry using the staining method described above. Control H8000-A56R+L8000 was used (8000=chimeric 4D5; the mouse parent of trastuzumab).

The flow cytometry results showed 2 populations in the 3.3 and 3.4 samples. The Her2 3.4 sample was co-infected into Hela cells and the sample stained for Her2 binding and positive cells sorted. Clones were picked from the sorted sample and screened 30 plaques were picked from Her2.3.4/sort and amplified for 2 days on BSC1 in 24-well plate (1 plaque per well). Hela cells were infected in 24-well plates with ⅓ of each amplified plaque The cells were co-infected with L116 at moi=1 (controls: 8000, 2368, 2408 and uninfected Hela supernatant). EEV was produced for 3 days, harvested, and inactivated with PLWUV. The virus was bound to CD100 (2 µg/ml) and Her2 (2 µg/ml) coated plates O/N using 50 µL EEV+50 µL ELISA blocking buffer per well. The results are shown in FIG. 10.

Antibody binding was detected by adding anti-Fab-HRP. Five positive clones were identified with good binding to Her2 and were sequenced. All 5 clones had the same sequence (see FIG. 11). The VH sequence of clone B10 is shown below.

Her2 B10 clone Sequence:

(SEQ ID NO: 20)
EVQLLESGGGFVQPGGSLRLSCAASGFAFNNYALSWVRQAPGRGLKWVSA

ISPDGDYIYYADSVKGRFIFSRDNSRNMLSLQMTSLGAEDTALYYCARQN

NVRDGAVAGPLDHWGQGTLVT.

Example 7: CH1-A56R Fusion Protein Library Screening for C35 Antibody Selection Selection for new C35 antibodies using ~1,200,000 clones from the naïve heavy, A56R fusion library (also referred to as "library 3")+light chain clones (L48, L116 and L9021) was performed. The library is the same that was used for the CD100 and Her2 selections discussed above.

Round 1 Selection.

100 µg C35 was conjugated to tosylactivated magnetic beads in PBS or ELISA coating buffer (CB). The solution was incubated at 37° C. overnight, and blocked for 1 hour at 37° C. with PBS, 10% FBS, 0.5% BSA. The beads were washed 1×, resuspended in 160 µl DMEM supplemented with 10%. 50 µl of each bead sample was added to each virus sample and incubated at room temp for 3.5 hours. Unbound was collected following standard 5×1 ml PBS washes. Beads were removed from the magnet, 1 ml DMEM supplemented with 2.5% was added, and the beads were transferred to fresh tube ("Bound"). "Unbound" and "Bound" were titered.

Bound library was amplified on Hela in T75 (Round 1 selection was termed "C35 3.1"). The results of the round C35 3.1 were tested by flow cytometry. C35 3.1 bound, but was low (data not shown).

Round 2 Selection. Amplified C35 3.1 was titered and used to produce recombinant EEV in 6 well plate format by co-infection of C35 3.1 with L48, L116 and L9021 (titer ~5×10^5/ml) and an additional cycle of tosylactivated C35 selection was performed using the methods described above. Solutions were incubated at room temp for 3.0 hours instead of 3.5 as in Round 1. The titers of bound and unbound virus are shown in Table 7. Bound library was amplified on Hela in T75 (Round 2 selection was termed "C35 3.2") and binding was tested by flow cytometry as described above.

TABLE 7

Round 2 C35-His/Tosylactivated Selection for C35 Ab

| Virus | Sample | Titer | % Bound |
|---|---|---|---|
| 2368 | Unbound | 684,000 | |
| 2368 | Bound | 1600 | 0.2% |
| 2408 | Unbound | 600,000 | |
| 2408 | Bound | 168,000 | 28% |
| Library C35 3.2 | Unbound | 972,000 | |
| Library C35 3.2 | Bound | 10,400 | 1% |

Round 3 Selection. Amplified C35 3.2 was titered and used to produce recombinant EEV in 6 well plate format by co-infecting with L48, L116 and L9021 (titer ~5×10^5/ml) and an additional cycle of tosylactivated C35 selection was performed using the methods described above for Round 2. The titers of bound and unbound virus are shown in Table 8. Bound library was amplified on Hela in T75 and tested for C35 binding by flow cytometry as above (Round 3 selection was termed "C35 3.3").

TABLE 8

Round 3 C35-His/Tosylactivated Selection for C35 Ab

| Virus | Sample | Titer | % Bound |
|---|---|---|---|
| 2368 | Unbound | 400,000 | |
| 2368 | Bound | 480 | 0.1% |
| 2408 | Unbound | 228,000 | |

TABLE 8-continued

Round 3 C35-His/Tosylactivated Selection for C35 Ab

| Virus | Sample | Titer | % Bound |
|---|---|---|---|
| 2408 | Bound | 108,000 | 47% |
| Library C35 3.3 | Unbound | 540,000 | |
| Library C35 3.3 | Bound | 2600 | 0.5% |

Clones will be screened from C35 3.3 as well a possible fourth round selection. Positive clones will be characterized by flow cytometry and tested for specificity, affinity, and function.

Example 8: Selective Amplification of Vaccinia Virus Expressing Heavy or Light Chains Combinatorial infection with separate recombinant vaccinia viruses harboring either heavy or light chain immunoglobulin is an effective way to express antibodies for selection. However, post-selection, during amplification and harvest, there is currently no mechanism for separating heavy and light chain-containing viruses. Therefore, it would be advantageous to be able to amplify heavy and light-containing vaccinia viruses separately as in the instance where both heavy and light chain infections are conducted at complexities of greater than one and where deconvolution post-selection is required. For this reason, recombinant vaccinia viruses expressing either heavy or light chain coupled to a drug selectable marker (heavy chain with neomycin resistance and light chain with hygromycin resistance) have been produced. The following experiment demonstrates utility in selectively amplifying heavy or light chain-containing recombinant vaccinia viruses independently.

BSC1 cells were seeded out into 15 wells of 6-well plates at $1.25 \times 10^6$ cells per well and at 2.5 ml per well. The next day, a series of dilutions of hygromycin or G418 for selection was created according to Table 9. DMEM-2.5 represents DMEM containing 2.5% FBS.

TABLE 9A

Preparation of hygromycin dilutions
Hygromycin Dilutions
[stock] = 50 mg/ml

| | 1<br>0.2<br>mg/ml | 2<br>0.1<br>mg/ml | 3<br>0.08<br>mg/ml | 4<br>0.04<br>mg/ml | 5<br>0.02<br>mg/ml | 6<br>0.01<br>mg/ml |
|---|---|---|---|---|---|---|
| Culture vol. (ml) needed: | 6 | 6 | 12 | 0.5 X serial | 0.5 X serial | 0.5 X serial |
| Add Hygro (µl): | 24 | 12 | 19.2 | 6 ml of 3 into 6 ml DMEM-2.5 | 6 ml of 4 into 6 ml DMEM-2.5 | 6 ml of 5 into 6 ml DMEM-2.5 |
| To DMEM-2.5 (ml): | 5.976 | 5.988 | 5.9808 | | | |

TABLE 9B

Preparation of G418 dilutions
G418 Dilutions
[stock] = 100 mg/ml

| | 1<br>2.0<br>mg/ml | 2<br>1.0<br>mg/ml | 3<br>0.5<br>mg/ml | 4<br>0.25<br>mg/ml | 5<br>0.125<br>mg/ml | 6<br>0<br>mg/ml |
|---|---|---|---|---|---|---|
| Culture vol. (ml) needed: | 5 | 5 | 5 | 5 | 5 | 5 |
| Add G418 (µl): | 200 | 5 ml of 1 | 5 ml of 2 | 5 ml of 3 | 5 ml of 4 | 5 ml of |

TABLE 9B-continued

Preparation of G418 dilutions
G418 Dilutions
[stock] = 100 mg/ml

|  | 1<br>2.0<br>mg/ml | 2<br>1.0<br>mg/ml | 3<br>0.5<br>mg/ml | 4<br>0.25<br>mg/ml | 5<br>0.125<br>mg/ml | 6<br>0<br>mg/ml |
|---|---|---|---|---|---|---|
| To DMEM-2.5 (ml): | 10 | into 5 ml<br>DMEM-2.5 | into 5 ml<br>DMEM-2.5 | into 5 ml<br>DMEM-2.5 | into 5 ml<br>DMEM-2.5 | DMEM-2.5 |

On the third day, the BSC1 cells were infected with MOI=3 of either wild-type vaccinia virus or vaccinia virus containing the respective selectable markers (VHE H5 LX-IRES-HYGRO or VHE H5 HX-A56R NEO). Hygromycin and G418 dilutions were then applied to the plate wells at the same time. DMEM-2.5 containing no antibiotics was added to the control wells. The infection was carried out in a volume of 0.65 ml per well and the cells were incubated at 37° C. After 2 hours, the media volumes were brought up to 2.65 ml per well and additional hygromycin or G418 was supplemented to maintain intended concentrations in the drug-containing wells. Meanwhile, new BSC1 cells were seeded into 12-well plates at $2 \times 10^5$ cells per well for post-infection titer determination.

24 hours post infection, all samples were harvested into 15 ml conical centrifuge tubes, freeze-thawed three times, vortexed, and resuspended by gentle vortexing into 1.8 ml DMEM-2.5. Samples were sonicated for 2 minutes at the maximum intensity and then transferred to a 2.0 ml Sarstedt tube. A series of dilutions was prepared for each sample in 7.5 ml polypropylene tubes. First, 30 μl of the original was withdrawn from each sample and combined with antibiotics-free DMEM-2.5 to a final volume of 3000 μl ($1:10^2$ dilution). Next, 30 μl of the $1:10^2$ dilution was added to a second final volume of 3000 μl to prepare a $1:10^4$ dilution. A series of 1:10 dilutions was then carried out to prepare the $1:10^5$ to $1:10^9$ dilutions. All the dilutions were vortexed in a biosafety cabinet using 5 ml tubes.

The BSC1 cells in the titer plates were subsequently infected using six dilutions ($1:10^4$ to $1:10^9$) from each sample by dispensing 0.333 ml of each titer dilution per assay well in duplicates. Therefore, the factor to calculate titer is equal to the total plaque number in 2 duplicate wells divided by 0.66 ml. The infection was incubated for at least 2 hours at 37° C. An additional 1.0 ml of DMEM-2.5 was added to each well after the initial 2 hours of adsorption and infection.

48 hours post infection, Crystal Violet was added to the 12-well titer plates. Only plaques greater than 1 mm diameter were counted. Daughter plaques were excluded from counting.

The results are shown in Table 10. In hygromycin resistance experiments, 0.01 to 0.08 mg/ml of hygromycin significantly inhibited the amplification of vaccinia virus expressing heavy chain linked to a neomycin resistance marker, but had little or no inhibition effect (except for the 0.04 mg/ml data point) on the amplification of vaccinia virus expressing light chain linked to a hygromycin resistance marker until the hygromycin concentration was increased to 0.1 to 0.2 mg/ml. Similarly, in neomycin resistance experiments, 0.125 to 2 mg/ml of G418 significantly inhibited the amplification of wild-type vaccinia virus, but had no inhibition effect on the amplification of vaccinia virus expressing heavy chain linked to a neomycin resistance marker.

TABLE 10A

Results of hygromycin resistance experiments
HYGRO RESISTANCE

| Sample ID | Titer | % Inhibition |
|---|---|---|
| Hygro 0.2 mg/ml VKE H5 LX-IRES-HYGRO | 2.20E+07 | 53.0 |
| Hygro 0.1 mg/ml VKE H5 LX-IRES-HYGRO | 1.70E+07 | 63.6 |
| Hygro 0.08 mg/ml VKE H5 LX-IRES-HYGRO | 4.47E+07 | 4.5 |
| Hygro 0.04 mg/ml VKE H5 LX-IRES-HYGRO | 2.77E+07 | 40.9 |
| Hygro 0.02 mg/ml VKE H5 LX-IRES-HYGRO | 4.66E+07 | 0.4 |
| Hygro 0.01 mg/ml VKE H5 LX-IRES-HYGRO | 5.98E+07 | −27.9 |
| Hygro 0.08 mg/ml VHE H5 HX-A56R NEO | 2.43E+06 | 89.1 |
| Hygro 0.04 mg/ml VHE H5 HX-A56R NEO | 2.66E+06 | 88.1 |
| Hygro 0.02 mg/ml VHE H5 HX-A56R NEO | 2.70E+06 | 87.9 |
| Hygro 0.01 mg/ml VHE H5 HX-A56R NEO | 6.86E+06 | 69.3 |
| [no antibiotic] VKE H5 LX-IRES-HYGRO | 3.86E+07 | Hygro control #1 |
| [no antibiotic] VKE H5 LX-IRES-HYGRO | 5.49E+07 | Hygro control #2 |
| [no antibiotic] VHE H5 HX-A56R NEO | 2.23E+07 | Neo control |

TABLE 10B

Results of neomycin resistance experiments
NEO RESISTANCE

| Sample ID | Titer | % Inhibition |
|---|---|---|
| G418 0.125 mg/ml WT | 1.58E+07 | 60.8 |
| G418 0.25 mg/ml WT | 8.26E+06 | 79.4 |
| G418 0.5 mg/ml WT | 2.54E+06 | 93.7 |
| G418 1 mg/ml WT | 1.36E+06 | 96.6 |
| G418 2 mg/ml WT | 1.59E+05 | 99.6 |
| G418 0.125 mg/ml VHE H5 HX-A56R NEO | 2.88E+07 | −26.7 |
| G418 0.25 mg/ml VHE H5 HX-A56R NEO | 3.11E+07 | −36.7 |
| G418 0.5 mg/ml VHE H5 HX-A56R NEO | 3.41E+07 | −50.0 |
| G418 1 mg/ml VHE H5 HX-A56R NEO | 3.18E+07 | −40.0 |
| G418 2 mg/ml VHE H5 HX-A56R NEO | 3.03E+07 | −33.3 |
| G418 0 mg/ml WT | 4.02E+07 | Neo control #1 |
| G418 0 mg/ml VHE H5 HX-A56R NEO | 2.27E+07 | Neo control #2 |

Therefore, recombinant vaccinia viruses expressing immunoglobulin and drug resistance markers linked via an Internal Ribosome Entry Site (IRES) provide for protection against death of the host cells under treatment with that drug. This allows for chain-specific propagation in virus as well as selection against wild-type vaccinia virus during recombination.

Example 9: Expression of A56R Fusion Protein on Surface of Hela Cells

HeLa cells were co-infected with recombinant EEV vaccinia virus expressing immunoglobulin fusion constructs, Variable Heavy (H8000) CH1-A56R with L8000 Ig-K which together encode an Fab fragment of antibody ("Fab"), Variable Heavy (H8000) FL-A56R with L8000 Ig-K which together encode full length ("FL") IgG, Variable Heavy (H8000) FL-truncated-A56R with L8000 Ig-K which together encode full length IgG with a shorter A56R ("TR"), Variable Heavy (H2124) FL-A56R with L517 Ig-K (2408 "FL"), and Variable Heavy (H2124) FL-truncated-A56R with L517 Ig-K (2408 "TR") in 12-well plates. A diagram showing the "Fab", "TR" and "IgG" constructs is shown in FIG. 12. Fluorescence Activated Cell Sorting (FACS) analysis for C35 staining and Her2 staining of cells infected with recombinant vaccinia virus was performed. After ~18 hours cells were stained with C35-His/His-APC and Her2-His/His-APC, and anti-Fab-FITC; and detected by FLOW analysis on Canto. Briefly, cells were trypsinized and divided into two per samples; washed with 2 mL wash buffer; 10 μg/ml Her2-His or 4 μg/ml C35-His were added to one of the two samples and incubated for 30 minutes on ice. The cells were then washed and anti-His APC was added and the samples were incubated for 30 minutes on ice, stained with secondary detection reagent anti-Fab-FITC, and then the samples were washed, fixed (0.5% Paraformaldehyde with 1:100PI for 20 min on ice) and analyzed by FLOW by Canto. The FACS data is shown in FIG. 13-15. These results show that the A56R fusion proteins, either expressing an Fab or Full Length IgG were expressed on the cell surface, and that only the transmembrane and intracellular domains of A56R are necessary for surface expression of IgG.

Example 10: Solution Based Vac-Ig Selection

Tosylactivated bead selection. EEV expressing the C35-specific (H2124) "Fab", "FL" and "TR" VH were co-infected along with L517 into Hela cells in 6 well plates, and EEV harvested from supernatant by spinning 1200 rpm and collecting supernatant (EEV) after approximately 48 hours of infection. As a control Her2 specific H8000-Fab+L8000 was produced the same way. For bead selection, 100 μg C35-His was conjugated to tosylactivated magnetic beads in PBS. The solution was incubated at 37° C. overnight, and blocked for 1 hour at 37° C. with PBS, 10% FBS, 0.5% BSA. The beads were washed 1×, resuspended in 160 μl DMEM supplemented with 10%. 50 μl of each bead sample was added to each virus sample and incubated at room temperature for 2 hours. Unbound EEV was collected in standard 5×1 ml PBS washes. Beads were removed from the magnet, 1 ml DMEM supplemented with 2.5% was added, and the beads were transferred to fresh tube ("Bound"). "Unbound" and "Bound" were titered.

As shown in Table 11, Vaccinia virus expressing C35-specific constructs of both the Fab and FL fusion proteins were selected, while the construct with the TR fusion protein was not. This data suggests that some extracellular A56R sequence is needed for incorporation into EEV.

TABLE 11

Results of Tosylactivated bead selection

| Virus | % Bound |
|---|---|
| MAb 2408-Fab | 24% |
| Mab 2408-FL | 18% |
| Mab 2408-TR | 2.3% |
| Mab 8000-Fab | 0.8% |

Example 11: CH1-A56R Fusion Protein Library Screening for CD100 Antibody Selection Selection for new CD100 antibodies using a heavy chain library comprised of ~7,000,000 clones containing a combination of naïve VH and synthetic VH sequences was produced in the A56R-Fab vector. To produce vaccinia expressing the library of Ig on the surface of EEV, the A56R fusion library (also referred to as "library 10") was co-infected into 1×10^9 Hela cells along with a cocktail of 9 light chain clones (Kappa Chains: L48, L116, L122, L7110, and L9021; and Lambda Chains: L3-1, L151, L214, and L223). The total moi of heavy chain virus was 1, and the total moi of light chain virus was 1, with each light chain comprising approximately 1/9th of the total light chain virus added.

Hela-S cells growing in suspension were infected for 2 days, after which the supernatant was harvested, pelleted with low speed spins 2×, and the EEV pelleted at 13,000 RPM for 1 hour in an F16/F250 rotor. EEV were resuspended in 3 ml DMEM supplemented with 10% FBS, and 1 ml was used to select CD100 specific antibodies.

Round 1 Selection.

EEV expressing 2368-A56R (1 ml virus with approximately ~5×10^5 pfu)) and EEV expressing 2408-A56R (1 ml virus with approximately 5×10^5 pfu) were used as controls and library 10 (1 ml virus with approximately ~10^8 pfu) was used for the selection assay. First, 300 μl Protein G beads (2× standard amount/sample) were pulled down with a magnet, and 600 μl PBS+18 μl CD100-Fc (=36 μg) was added to the beads. The solution was incubated at room temp for 20 minutes (on a rotator) to allow CD100-Fc to bind to Protein G beads. Beads were pulled down with magnet, washed 1× with 1 ml PBS, and resuspended in 300 μl DMEM supplemented with 10% FBS.

Next, 100 μl of the CD100-Fc/Pro G per sample (about 12 μg/ml CD100-Fc) was added to the EEV (2408 and 2368 controls, and library 10) and incubated for 2 hours at room temperature. Unbound virus was removed following standard 5×1 ml PBS washes. Beads were removed from the magnet and 1 ml DMEM supplemented with 2.5% was added, and the solution was transferred to a fresh tube ("Bound"). "Unbound" and "Bound" were titered. The results are shown in Table 12. Bound virus was amplified on BSC1 cells in T175 flasks for 3 days.

TABLE 12

Results of Tosylactivated bead selection

| Virus | Selection | Titer Unbound | Titer Bound | Percent Bound |
|---|---|---|---|---|
| Library_10 | CD100-Fc | 1.5 × 10^8 | 2.2 × 10^6 | 0.15 |
| 2368 | CD100-Fc | 72,000 | 37,000 | 34 |
| 2408 | CD100-Fc | 338,400 | 80 | 0.12 |

These results show that Library 10.1 gave good amplification on BSC1, harvest and titer.

Round 2 Selection.

EEV from 10.1+a fresh aliquot of the 9 Light chains was produced by infecting Hela cells in a cell stacker at moi=1 each for 2 days, and harvesting as described above. The harvested virus was split in half, with 50% being selected on ProG beads, and 50% being selected on CD100 coated Tosyl activated bead.

Round 2 Employing ProG Bead Selection.

EEV expressing 2368-A56R (1 ml virus (~5×10^5 pfu)), EEV expressing 2408-A56R (1 ml virus (5×10^5 pfu)) and 10.1 library (1 ml virus (5×10^5 pfu)) were used for selection. 600 μl PBS+18 μl CD100-Fc (=36 μg) was added to the Pro-G beads. The solution was incubated at room temperature for 20 minutes (on a rotator) to allow CD100-Fc to bind to Protein G beads. The beads were washed and resuspended as described above for Round 1. 100 µl CD100-Fc/Pro G per sample (~12 µg/ml CD100-Fc) was added to the virus samples and incubated for 2 hours at room temperature. The "Unbound" and "Bound" were collected and titered. Bound library was amplified on BSC1 in T75 (Round 2 selection was termed "CD100 10.2/ProG"). The results of the Round 2 selection are shown in Table 13A. Bound virus was amplified on BSC1 in a T175 flask for 3 days.

Round 2 Employing Tosylactivated Bead Selection.

EEV expressing the same 2408 (C35-specific), 2368 (CD100-specific) and Library 10 antibodies used in the Protein G bead selection experiments above were used for the tosylactivated magnetic bead selection. 100 µg CD100-His was conjugated to tosylactivated magnetic beads in PBS. The solution was incubated at 37° C. overnight, and blocked for 1 hour at 37 with PBS, 10% FBS, 0.5% BSA. The beads were washed 1× with DMEM, 10% FBS, resuspended in 160 µl DMEM supplemented with 10% FBS. 50 µl of each bead sample was added to each virus sample and incubated at room temperature for 2 hours. Unbound virus was collected in standard 5×1 ml PBS washes. Beads were removed from the magnet, 1 ml DMEM supplemented with 2.5% was added, and the beads were transferred to a fresh tube ("Bound"). "Unbound" and "Bound" were titered. Bound virus was amplified on BSC1 in a T175 flask for 3 days. The results of the Round 2 selection are shown in Table 13B.

TABLE 13A

Round 2 Selection for CD100 Ab (Protein G Bead Selection)

| Virus | Selection | Titer Unbound | Titer Bound | Percent Bound |
|---|---|---|---|---|
| Library_10.1 Protein G | CD100-Fc | 4.4 × 10^7 | 67,000 | 0.15 |
| 2368 | CD100-Fc | 104,400 | 66,000 | 38.7 |
| 2408 | CD100-Fc | 240,000 | 80 | 0.03 |

TABLE 13B

Round 2 Selection for CD100 Ab (Tosylactivated Bead Selection)

| Virus | Selection | Titer Unbound | Titer Bound | Percent Bound |
|---|---|---|---|---|
| Library_10.1 Tosyl | CD100-His | 2.4 × 10^7 | 113,000 | 0.47 |
| 2368 | CD100-His | 56,400 | 106,000 | 34.4 |
| 2408 | CD100-His | 354,000 | 0 | 0 |

These second round results show that Library 10.2/ProG and 10.2/Tosyl both gave good amplification on BSC1.

Round 3 Selections.

A third round of selection was performed using the same methods described above. 10.2/ProG was selected with CD100-Fc/ProG for the third round, and 10.2/Tosyl was selected with CD100-His/Tosyl for the third round. EEV from 10.2/ProG+a fresh aliquot of the 9 Light chains was produced by infecting Hela cells in a T175 at moi=1 each for total heavy chain and total light chain recombinant virus for 2 days, and harvesting as described above. EEV from 10.2/Tosyl+a fresh aliquot of the 9 Light chains was produced by infecting Hela cells in a T175 flask at moi=1 each for total heavy chain and total light chain recombinant virus for 2 days, and harvesting as described above. Titers are shown in Table 14A-B.

TABLE 14A

Round 3 Selection for CD100 Ab (Protein G Bead Selection)

| Virus | Selection | Titer Unbound | Titer Bound | Percent Bound |
|---|---|---|---|---|
| Library_10.2 Protein G | CD100-Fc | 2.5 × 10^7 | 364,000 | 1.44 |
| 2368 | CD100-Fc | 84,000 | 58,000 | 48.5 |
| 2408 | CD100-Fc | 99,600 | 0 | 0 |

TABLE 14B

Round 3 Selection for CD100 Ab (Tosylactivated Bead Selection)

| Virus | Selection | Titer Unbound | Titer Bound | Percent Bound |
|---|---|---|---|---|
| Library_10.2 Tosyl | CD100-His | 8.2 × 10^6 | 6,100 | 0.074 |
| 2368 | CD100-His | 69,600 | 108,000 | 60.8 |
| 2408 | CD100-His | 121,000 | 0 | 0 |

Bound library was amplified on BSC1 in T75 (Round 3 selection was termed "CD100 10.3ProG and CD100 10.3/Tosyl"). The results of the Round 3 selection were tested by flow cytometry.

In this experiment, an aliquot of the 10.3 selections were co-infected individually with each Light chain and then tested for binding to CD100 and Her2. Hela cells were infected at moi=1. After an overnight infection cells were harvested and stained for CD100 binding and Her2 binding as control. Cells were trypsinized, washed with ice cold Flow Buffer (FB 1×PBS, 0.5% BSA, 2 mM EDTA) and detected with each of three different detection methods. In the first detection method (2 step) cells were incubated for 30 min with 10 ug/mL huCD100-His in FB on ice, then washed with 2 mL of FB and incubated with 1:50 (2 ug/mL) of Mouse anti 6×His-APC mixed with 1:500 (2 ug/mL) FITC labeled Goat-Fab anti-human-Fab on ice for 30 min. In the second and third detection method (Pre-complexed) either 10 ug/mL of hu CD100-His or 10 ug/mL huHer2-His were preincubated with 1:50 (2 ug/mL) of Mouse anti 6×His-APC in FB on ice for 30 min, then the mix was added to cells with 1:500 (2 ug/mL) GtFab anti huFab-FITC and incubated for 30 min on ice. After the incubation with detection reagents cells were washed 1× with 2 mL FB, reconstituted in 0.5% paraformaldehyde and incubated on ice for 20 min. 20,000 events were read on FACS Canto. Results are shown in FIGS. 16-22.

Flow cytometry staining showed that there was a positive population of CD100 binding cells in CD100 10.3/ProG and Tosyl when paired with most of the light chains. In particular, a strongly positive population was observed when co-infected with L3-1.

In order to isolate the specific VH, Hela cells were separately infected with 10.3/ProG or 10.3/tosyl, and co-infected with L3-1. After an overnight infection the cells were harvested and stained for CD100 binding with a precomplexed method as described above. Then the antigen binding cells were isolated by cell sorting. After sorting the virus was released from the cells by freeze/thaw, and then the virus was amplified on BSC1 cells. The amplified sample of isolated EEV-VH chains was tested for enrichment by analytical flow assay. In this assay an aliquot of the amplified sorted CD100 10.3 sample was co-infected with L3-1 Light chain and then with the 2-step and precomplexed method described above. Results are shown in FIGS. 23-25.

Following amplification the virus was harvested and DNA extracted from an aliquot of the virus using Qiagen DNA blood mini kit (cat #51104). The purified DNA was PCR amplified with Heavy chain specific primers 428; 5'-GATATATTAAAGTCGAATAAAGTG-3' (SEQ ID NO:31) and 430; 5'-GACATCACATAGTTTAGTTGC-3' (SEQ ID NO:32). The resulting PCR product was cloned into plasmid vector containing secreted full length human IgG1 (EFVH) and then the V gene contained in the resulting colonies was sequenced. A summary of the sequencing results is shown in Table 15. After sequencing 188 clones from 10.3/ProG, 44 unique clones were identified, and after sequencing 188 clones from 10.3/toysl, 46 unique clones were identified.

TABLE 15

Summary of Unique Clones

| Screen | Clones sequenced | unique sequences | bound by ELISA |
|---|---|---|---|
| 10.3/ProG | 188 | 44 | 56.8% |
| 10.3/tosyl | 188 | 46 | 60.9% |

Plasmid DNA for each unique heavy chain was co-transfected along with a plasmid vector encoding VL3-1 into CHO cells using Lipofectamine 2000 for 3 days, and then the antibody contained in the media was tested for specificity for CD100 by flow cytometry on CD100+Jurkat cells and by ELISA (FIGS. 26 and 27A-B, respectively). For the flow cytometry assay, the experimental antibody was pre-incubated at 1 ug/mL with 1:400 or [2.5 ug/mL] Gt anti Hu Fc-Dylight 649 secondary in Flow Buffer (1×PBS, 0.5% BSA, 2 mM EDTA). Jurkat cells were seeded at 250,000/well in 96 well plate and incubated with preformed Ab complex for 30 min on ice. The cells were then washed 2× with 200 uL Flow Buffer and incubated for 20 min with 0.5% Paraformaldehyde with 1× Propidium Iodide (PI). Cells were detected on FACS Canto reading 10,000 events gated on live cell population. In total, at least 75 unique antibodies were shown to be specific for CD100 by ELISA or Flow Cytometry.

Example 12: CH1-A56R Fusion Protein Library Screening for Her2 Antibody Selection A heavy chain library comprised of ~3,000,000 clones containing a combination of naïve VH and synthetic VH sequences was produced in the A56R-Fab vector as a fusion with IRES-Neomycin. To produce vaccinia expressing the library of Ig on the surface of EEV, the A56R fusion library (also referred to as "library 9") was co-infected along with a library of 1,000 Kappa Light chain clones containing a hygromycin resistance gene into 5×10^9 Hela cells. The Light chain library was comprised of VK sequences isolated from human bone marrow (naïve). The total moi of heavy chain virus was 1, and the total moi of light chain virus was 1.

Hela-S cells growing in suspension were infected for 2 days, after which the supernatant was harvested, pelleted with low speed spins 2×, and the EEV pelleted at 13,000 RPM for 1 hour in a F16/F250 rotor. EEV was resuspended in 3 ml DMEM supplemented with 10% FBS, and 1 ml was used to select Her2/neu specific antibodies.

Round 1 Selection.

Library 9 was used for this selection. First, 100 µl PBS+24 ug Her2-Fc was added to 600 ul the Protein G beads. The solution was incubated at room temperature for 20 minutes (on rotator) to allow Her2-Fc to bind to Protein G beads. Beads were pulled down with magnet, washed 1× with 1 ml PBS, and resuspended in 400 µl DMEM supplemented with 10% FBS.

Next, 100 µl Her2-Fc/Pro G (~6 µg/ml Her2-Fc) was added to 1 ml of Library 9 and incubated for 2 hours at room temperature. A similar amount of beads were added to positive control MAb 8000 EEV and negative control MAb 2408 EEV. Beads were removed and unbound virus was collected in standard 5×1 ml PBS washes. Beads were removed from the magnet and 1 ml DMEM supplemented with 2.5% FBS was added, and the solution was transferred to fresh tube ("Bound"). "Unbound" and "Bound" were titered (See Table 16). Beads recovered from the bound library were amplified on BSC1 in three T175 flaks in the presence of 1 mg/ml G418. This amplification selected for Heavy chain recombinant virus. (Round 1 selection was termed "Her.9.1").

TABLE 16

Round 1 Selection for Her2 Ab

| Virus | Selection | Titer Unbound | Titer Bound | Percent Bound |
|---|---|---|---|---|
| Library 9 | Her2-Fc | $1.4 \times 10^9$ | $4.610^6$ | 0.32 |
| 2408 | Her2-Fc | $1.2 \times 10^5$ | 180 | 0.14 |
| 8000 | Her2-Fc | $3 \times 10^5$ | $7.2 \times 10^4$ | 19.3 |

Round 2 Selection.

Amplified Her.9.1 was titered and a second round of selection was performed by co-infecting the Her.9.1 VH and a fresh aliquot of the VK1000 Library into Hela cells in 2 CellStackers for 2 days. Virus was harvested as described above and an additional cycle of Her2-Fc/ProG selection was performed using the methods described above. 50% of the bound virus was amplified on BSC1 in two T175 flasks with 1 mg/ml G418 (to select for Heavy chains) and 50% of the bound virus was amplified on BSC1 in two T175 flasks with 0.030 mg/ml Hygro (to select for Light chains). The titer results are shown in Table 17. The amplified viruses were named Her.9.2/VH and Her 9.2/VK.

TABLE 17

Round 2 Selection for Her2 Ab

| Virus | Selection | Titer Unbound | Titer Bound | Percent Bound |
|---|---|---|---|---|
| Her2 9.Rd1 + VK | Her2-Fc | $1.76 \times 10^8$ | $1.910^5$ | 0.1 |
| 2408 | Her2-Fc | $1.4 \times 10^5$ | 80 | 0.1 |
| 8000 | Her2-Fc | $3.3 \times 10^5$ | $6.2 \times 10^4$ | 16 |

Round 3 Selection.

Amplified Her.9.2/VH and Her 9.2/VK were titered, co-infected into Hela cells in a CellStacker for 2 days, EEV purified as described above, and an additional cycle of Her2-Fc/ProG selection was performed using the methods described above.

50% of the bound virus was amplified on BSC1 in a T175 flask with 1 mg/ml G418 (to select for Heavy chains) and 50% of the bound virus was amplified on BSC1 in a T175 flask with 0.030 mg/ml Hygro (to select for Light chains). The amplified viruses were named Her.9.3/VH and Her 9.3/VK.

The selection for Her2 specific antibodies in Her.9.3/VH and Her 9.3/VK was tested by flow cytometry. Hela cells were co-infected at moi=1 with Her9.3/VH and Her9.3/VK overnight, and then stained for binding to Her2, with the absence of binding to a control antigen (C35). In this experiment, 3 µg/ml C35-His or 6 µg/ml Her2-His were incubated with anti-His-APC antibody for 30 minutes on ice to form complexes. Anti-Fab-FITC as then added and the Antigen-anti-His complexes were added to the cells for 30 minutes on ice. The cells were then washed with 2 ml PBS, 0.5% BSA, 2 nM EDTA. The cells were fixed and flow cytometry assay was run. The data showed enrichment of both VH and VK.

To further enrich, fresh Hela cells were infected with the 9.3VH and VK at moi=1 each, the cells were stained as above, and then the antigen binding cells were sorted. Virus was released from the sorted cells by three cycles of freeze/thaw and then 50% of the virus was amplified on BSC1 in a T75 flask with 1 mg/ml G418 (to select for Heavy chains) and 50% of the virus was amplified on BSC1 in a T75 flask with 0.030 mg/ml Hygro (To select for Light chains). The amplified viruses were titered and named Her.9.3/VH/Sort and Her 9.3/VK/sort.

The selection for Her2 specific antibodies in Her.9.3/VH/sort and Her 9.3/VK/sort was tested by flow cytometry. Hela cells were co-infected at moi=1 with Her9.3/VH/sort and Her9.3/VK/sort overnight, and then stained for binding to Her2, with the absence of binding to a control antigen (C35). In this experiment, 3 µg/ml C35-His or 6 µg/ml Her2-His were incubated with anti-His-APC antibody for 30 minutes on ice to form complexes. Anti-Fab-FITC was then added and the Antigen-anti-His complexes were added to the cells for 30 minutes on ice. The cells were then washed with 2 ml PBS, 0.5% BSA, 2 nM EDTA. The cells were then fixed and flow cytometry assay was run. The data in showed enrichment of both VH and VK.

In order to fix the antigen specific pairing of VH and VK, Her.9.3/VH/sort and Her 9.3/VK/sort were co-infected into Hela cells at moi=0.1 each, and then stained as described for binding Her2 above. The cells were again sorted, but this time individual infected cells were sorted into individual wells of a 96 well plate. Each antigen binding sorted cell should contain a fixed antigen specific pairing of specific VH with specific VK. After sorting, the cells were subjected to freeze/thaw, and then the virus was amplified on BSC1 in a 96 well plate, with virus from one cell being amplified in one recipient well. After 5 days the plates were subjected to freeze/thaw, and then an aliquot of virus in each well was infected into Hela cells in 96 well plate. The virus in each well should contain a mix of VH and VK, and the infection of Hela cells should result in expression of surface IgG and antigen binding. After an overnight binding the cells were harvested and stained for Her2 binding as described above (FIG. 28).

From screening 1 plate, 26 specific clones were identified. Repeat testing of these clones demonstrated that they bind to Her2, but not C35 by flow cytometry. Three representative clones (D5, D8, and H2) are show in FIG. 29A-C. DNA was then extracted from the viruses, and the VH and VK genes contained in these viruses was PCR amplified with VH and VK specific primers and cloned into mammalian expression vectors so that they would be expressed as full length IgG1 and full length Kappa. The sequences of the VH and VK genes were then determined. By sequencing, these 26 clones contained 15 unique antibodies. These antibodies were then expressed in CHO cells by co-transfection of the IgG and Kappa expression plasmids, and antibody was harvested from the cell supernatant after 3 days. Antibody was quantitated by ELISA, and then tested for specificity by ELISA and flow cytometry on SKBR3 cells (Her2+++). Representative data for antibodies shown to have specificity by ELISA and flow cytometry is shown in FIGS. 30 and 31, respectively.

Repeating the single cell sorting and screening additional clones according to the methods herein resulted in the identification of additional novel anti-Her2 antibodies.

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference. The disclosure and claims of U.S. application Ser. No. 08/935,377, filed Sep. 22, 1997 and U.S. Application No. 60/192,586, filed Mar. 28, 2000 are herein incorporated by reference.

What is claimed is:

1. A recombinant vaccinia library comprising a library of polynucleotides constructed in a vaccinia virus vector encoding a plurality of immunoglobulin fusion polypeptides, wherein the vaccinia virus vector comprises
   (a) a first polynucleotide encoding a first polypeptide segment comprising a heavy chain CH1 domain,
   (b) a second polynucleotide encoding a second polypeptide segment comprising the the stalk region, the transmembrane domain, and the intracellular domain of the vaccinia virus EEV-specific A56R protein situated downstream of the CH1 domain, wherein the second polypeptide segment comprises amino acids 215 to 421 of SEQ ID NO: 11 or amino acids 447 to 653 of SEQ ID NO: 30, and
   (c) a third polynucleotide encoding an immunoglobulin heavy chain variable region or fragment thereof situated upstream of the CH1 domain.

2. The recombinant vaccinia library of claim 1, wherein each immunoglobulin fusion polypeptide further comprises a signal peptide for facilitating expression of the plurality of immunoglobulin fusion polypeptides on the surface of EEV.

3. The recombinant vaccinia library of claim 1, wherein the first polypeptide segment further comprises a heavy chain CH2 domain, a heavy chain CH3 domain, or a combination thereof.

4. The recombinant vaccinia library of claim 3, wherein the first polypeptide segment comprises a human IgG constant region, or portion thereof.

* * * * *

UNITED STATES PATENT AND TRADEMARK OFFICE
CERTIFICATE OF CORRECTION

PATENT NO. : 10,662,422 B2
APPLICATION NO. : 15/619790
DATED : May 26, 2020
INVENTOR(S) : Ernest S. Smith et al.

Page 1 of 1

It is certified that error appears in the above-identified patent and that said Letters Patent is hereby corrected as shown below:

In the Claims

In Column 75, Line 9, remove the second instance of "the"

Signed and Sealed this
Tenth Day of November, 2020

Andrei Iancu
*Director of the United States Patent and Trademark Office*